US011786554B2

(12) United States Patent
Smith et al.

(10) Patent No.: US 11,786,554 B2
(45) Date of Patent: Oct. 17, 2023

(54) OPTIMIZED ENGINEERED NUCLEASES HAVING SPECIFICITY FOR THE HUMAN T CELL RECEPTOR ALPHA CONSTANT REGION GENE

(71) Applicant: Precision BioSciences, Inc., Durham, NC (US)

(72) Inventors: James Jefferson Smith, Morrisville, NC (US); Janel Lape, Wake Forest, NC (US); Hui Li, Apex, NC (US); Jochen Genschel, Raleigh, NC (US)

(73) Assignee: Precision BioSciences, Inc., Durham, NC (US)

( * ) Notice: Subject to any disclaimer, the term of this patent is extended or adjusted under 35 U.S.C. 154(b) by 545 days.

(21) Appl. No.: 17/046,761

(22) PCT Filed: Apr. 11, 2019

(86) PCT No.: PCT/US2019/027019
§ 371 (c)(1),
(2) Date: Oct. 9, 2020

(87) PCT Pub. No.: WO2019/200122
PCT Pub. Date: Oct. 17, 2019

(65) Prior Publication Data
US 2021/0113616 A1 Apr. 22, 2021

Related U.S. Application Data

(60) Provisional application No. 62/656,809, filed on Apr. 12, 2018.

(51) Int. Cl.
*C12N 9/22* (2006.01)
*C12N 15/86* (2006.01)
(Continued)

(52) U.S. Cl.
CPC .......... *A61K 35/17* (2013.01); *C07K 14/7051* (2013.01); *C12N 9/22* (2013.01); *C12N 15/86* (2013.01); *C12N 2750/14143* (2013.01)

(58) Field of Classification Search
CPC . C12N 9/22; C12N 15/86; C12N 2750/14143
See application file for complete search history.

(56) References Cited

U.S. PATENT DOCUMENTS 4,873,192 A 10/1989 Kunkel
6,015,832 A 1/2000 Baker, Jr. et al.
(Continued)

FOREIGN PATENT DOCUMENTS

EP 3 004 337 B1 8/2017
JP 2009-511085 A 3/2009
(Continued)

OTHER PUBLICATIONS

Extended European Search Report dated Jun. 15, 2020 in connection with Application No. EP 19212310.7.
(Continued)

*Primary Examiner* — Gary B Nickol
*Assistant Examiner* — Amelia Nicole Dickens
(74) *Attorney, Agent, or Firm* — Womble Bond Dickinson (US) LLP

(57) ABSTRACT

The present invention encompasses engineered nucleases which recognize and cleave a recognition sequence within the first exon of the human T cell receptor (TCR) alpha constant region gene. The engineered meganucleases can exhibit at least one optimized characteristic, such as enhanced (i.e., increased) specificity or efficiency of cleavage, when compared to the first-generation meganuclease TRC 1-2x.87EE. The present invention also encompasses methods of using such engineered nucleases to make genetically-modified cells, and the use of such cells in a pharma-
(Continued)

ceutical composition and in methods for treating diseases, such as cancer.

5 Claims, 25 Drawing Sheets

Specification includes a Sequence Listing.

(51) Int. Cl.
*A61K 35/17* (2015.01)
*C07K 14/725* (2006.01)

(56) References Cited

U.S. PATENT DOCUMENTS

| | | | |
|---|---|---|---|
| 6,506,803 | B1 | 1/2003 | Baker, Jr. et al. |
| 6,559,189 | B2 | 5/2003 | Baker, Jr. et al. |
| 6,635,676 | B2 | 10/2003 | Baker, Jr. et al. |
| 8,021,867 | B2 | 9/2011 | Smith et al. |
| 8,445,251 | B2 | 5/2013 | Smith et al. |
| 8,697,359 | B1 | 4/2014 | Zhang |
| 8,822,647 | B2 | 9/2014 | Jensen et al. |
| 8,956,828 | B2 | 2/2015 | Bonini et al. |
| 9,434,931 | B2 | 9/2016 | Smith et al. |
| 9,889,160 | B2 | 2/2018 | Jantz et al. |
| 9,889,161 | B2 | 2/2018 | Jantz et al. |
| 9,950,010 | B1 | 4/2018 | Jantz et al. |
| 9,950,011 | B1 | 4/2018 | Jantz et al. |
| 9,969,975 | B1 | 5/2018 | Jantz et al. |
| 9,993,501 | B2 | 6/2018 | Jantz et al. |
| 9,993,502 | B1 | 6/2018 | Jantz et al. |
| 10,093,899 | B1 | 10/2018 | Jantz et al. |
| 10,093,900 | B2 | 10/2018 | Jantz et al. |
| 10,799,535 | B2 | 10/2020 | Nicholson et al. |
| 11,053,484 | B2 | 7/2021 | Jantz et al. |
| 2002/0045667 | A1 | 4/2002 | Baker et al. |
| 2004/0043041 | A1 | 3/2004 | Baker et al. |
| 2012/0321667 | A1 | 12/2012 | Sentman |
| 2013/0315884 | A1 | 11/2013 | Galetto et al. |
| 2014/0034902 | A1 | 2/2014 | Hwang et al. |
| 2014/0301990 | A1 | 10/2014 | Gregory et al. |
| 2014/0349402 | A1 | 11/2014 | Cooper et al. |
| 2015/0376650 | A1 | 12/2015 | Auerbach et al. |
| 2016/0081314 | A1 | 3/2016 | Thurston et al. |
| 2016/0120906 | A1 | 5/2016 | Galetto et al. |
| 2016/0208243 | A1 | 7/2016 | Zhang et al. |
| 2017/0016027 | A1 | 1/2017 | Lee et al. |
| 2017/0333481 | A1 | 11/2017 | Jantz et al. |
| 2017/0335010 | A1 | 11/2017 | Jantz et al. |
| 2018/0289741 | A1 | 10/2018 | Nicholson et al. |
| 2018/0360883 | A1 | 12/2018 | Galetto et al. |
| 2019/0017075 | A1 | 1/2019 | Bartsevich et al. |
| 2019/0194616 | A1 | 6/2019 | Jantz et al. |
| 2020/0123516 | A1 | 4/2020 | Jantz et al. |
| 2021/0052650 | A1 | 2/2021 | Nicholson et al. |
| 2021/0207093 | A1 | 7/2021 | Jantz et al. |

FOREIGN PATENT DOCUMENTS

| | | |
|---|---|---|
| JP | 2011-501971 A | 1/2011 |
| JP | 2013-538562 A | 10/2013 |
| WO | WO 2002/012514 A2 | 2/2002 |
| WO | WO 2007/047859 A2 | 4/2007 |
| WO | WO 2008/102199 A1 | 8/2008 |
| WO | WO 2008/102274 A2 | 8/2008 |
| WO | WO 2009/059195 A2 | 5/2009 |
| WO | WO 2010/015899 A2 | 2/2010 |
| WO | WO 2012/012667 A1 | 1/2012 |
| WO | WO 2012/167192 A2 | 12/2012 |
| WO | WO 2013/074916 A1 | 5/2013 |
| WO | WO 2013/153391 A1 | 10/2013 |
| WO | WO 2013/176915 A1 | 11/2013 |
| WO | WO 2014/153470 A2 | 9/2014 |
| WO | WO 2014/191128 A1 | 12/2014 |
| WO | WO 2014/191525 A1 | 12/2014 |
| WO | WO 2014/191527 A1 | 12/2014 |
| WO | WO 2015/057980 A1 | 4/2015 |
| WO | WO 2015/121454 A1 | 8/2015 |
| WO | WO 2015/136001 A1 | 9/2015 |
| WO | WO 2015/138739 A2 | 9/2015 |
| WO | WO 2015/167766 A1 | 11/2015 |
| WO | WO 2016/069282 A1 | 5/2016 |
| WO | WO 2016/069283 A1 | 5/2016 |
| WO | WO 2016/160721 A1 | 10/2016 |
| WO | WO 2017/011519 A1 | 1/2017 |
| WO | WO 2017/023801 A1 | 2/2017 |
| WO | WO 2017/062439 A1 | 4/2017 |
| WO | WO 2017/062451 A1 | 4/2017 |
| WO | WO 2017/070429 A1 | 4/2017 |
| WO | WO 2017/112859 A1 | 6/2017 |
| WO | WO 2017/156484 A1 | 9/2017 |
| WO | WO 2017/180989 A2 | 10/2017 |

OTHER PUBLICATIONS

International Search Report and Written Opinion dated Dec. 19, 2016 for Application No. PCT/US2016/055472.
International Preliminary Report on Patentability dated Apr. 19, 2018 for Application No. PCT/US2016/055472.
International Search Report and Written Opinion for Application No. PCT/US2016/055492 dated Feb. 3, 2017.
International Preliminary Report on Patentability dated Apr. 19, 2018 for Application No. PCT/US2016/055492.
International Search Report and Written Opinion for Application No. PCT/US2016/068289 dated Jun. 8, 2017.
International Preliminary Report on Patentability for Application No. PCT/US2016/068289 dated Jul. 5, 2018.
Extended European Search Report dated Nov. 26, 2020 in connection with Application No. EP 20172471.3.
International Search Report and Written Opinion for Application No. PCT/US2018/039740 dated Sep. 24, 2018.
International Preliminary Report on Patentability for Application No. PCT/US2018/039740 dated Jan. 9, 2020.
International Search Report and Written Opinion for Application No. PCT/US2019/027019 dated Jun. 27, 2019.
International Preliminary Report on Patentability for Application No. PCT/US2019/027019 dated Oct. 22, 2020.
EPO Communication for Application No. EP 16782371.5 dated Nov. 8, 2019. 6 pages.
[No Author Listed], Genbank Accession No. BDV42890. TRC 1-2x.87 EE meganuclease, Seq Id 8. Jun. 1, 2017; 1 page.
[No Author Listed], Genbank Accession No. BDV42894. TRC 1-2x.6 meganuclease, Seq Id 12. Jun. 1, 2017; 1 page.
[No Author Listed], Genbank Accession No. BDV42944. TRC 1-2x.6 meganuclease 7-153, Seq Id 62. Jun. 1, 2017; 1 page.
[No Author Listed], Genbank Accession No. BDV43178. Chlamydomonas reinhardtii CreI meganuclease, Seq Id 8. Jun. 15, 2017; 1 page.
[No Author Listed], Genbank Accession No. BDV43182. Chlamydomonas reinhardtii CreI meganuclease, Seq Id 12. Jun. 15, 2017; 1 page.
[No Author Listed], Genbank Accession No. BDV43232. Chlamydomonas reinhardtii CreI meganuclease, Seq Id 62. Jun. 15, 2017; 1 page.
[No Author Listed], Genbank Accession No. BEA51599. TRC 1-2x.87 EE meganuclease, Seq Id 131. Aug. 10, 2017; 1 page.
[No Author Listed], Genbank M94081.1. Human TCR-c-DELTA Genem Exons 1-4; Tcr-V-delta gene, exons 1-2; T-cell receptor alpha (Tcr-alpha) gene, J1-J61 segments; and Tcr-C-alpha gene, exons 1-4.. Jul. 24, 2016; Last Accessed Apr. 27, 2021; 27 pages.
Airenne et al., "Baculovirus: an insect-derived vector for diverse gene transfer applications," Mol. Ther. 21(4), 739-749 (2013).
Altschul et al., "Basic local alignment search tool," J. Mol. Biol. 215, pp. 403-410 (1990).
Altschul et al., "Gapped BLAST and PSI-BLAST: a new generation of protein database search programs," Nucleic Acids Res. 25, pp. 3389-3402 (1997).

(56) References Cited

OTHER PUBLICATIONS

Arnould et al., "Engineering of large numbers of highly specific homing endonucleases that induce recombination on novel DNA targets," J. Mol. Biol. 355, pp. 443-458 (2006).
Baxter et al., "Engineering domain fusion chimeras from I-OnuI family LAGLIDADG homing endonucleases," Nucleic Acids Research, 40(16), pp. 7985-8000 (2012).
Benoist et al., "In vivo sequence requirements of the SV40 early promotor region," Nature 290(5804), pp. 304-310 (1981).
Beurdeley et al., "Compact designer TALENs for efficient genome engineering," Nat. Commun. 4, p. 1762 (2013).
Boissel et al., "megaTALs: a rare-cleaving nuclease architecture for therapeutic genome engineering," Nucleic Acid Research 42(4), pp. 2591-2601 (2014).
Brickman et al., A wider context for gene trap mutagenesis. Methods Enzymol. 2010;477:271-95. doi: 10.1016/S0076-6879(10)77014-2.
Cahill et al., "Mechanisms of eukaryotic DNA double strand break repair," Front. Biosci. 11, pp. 1958-1976 (2006).
Cartellieri et al., Chimeric antigen receptor-engineered T cells for immunotherapy of cancer. J Biomed Biotechnol. 2010;2010:956304. doi: 10.1155/2010/956304. Epub May 5, 2010.
Chames et al., "In vivo selection of engineered homing endonucleases using double-strand break induced homologous recombination," Nucleic Acids Res. 33, p. e178 (2005).
Chang et al., "Inducible retroviral vectors regulated by lac repressor in mammalian cells," Gene 183, pp. 137-142 (1996).
Chen et al., "A novel adenoviral vector carrying an all-in-one Tet-On system with an autoregulatory loop for tight, inducible transgene expression," BMC Biotechnol. 15, 8 pages (2015).
Chen, "Exploiting the Intron-splicing Mechanism of Insect Cells to Produce Viral Vectors Harboring Toxic Genes for Suicide Gene Therapy," Mol. Ther. Nucleic Acids 1, e57; pp. 1-10 (2012).
Cheng et al., "Dendrimers as drug carriers: applications in different routes of drug administration," J. Pharm. Sci. 97(1): 123-143 (2008).
Chevalier and Stoddard, "Homing endonucleases: structural and functional insight into the catalysts of intron/intein mobility," Nucleic Acids Res. 29(18), pp. 3757-3774 (2001).
Cots et al., "Helper dependent adenovirus vectors: progress and future prospects," Curr. Gene Ther. 13(5) pp. 370-381 (2013).
Declaration of Interference filed Aug. 19, 2019 before the USPTO Patent Trial and Appeal Board on behalf of Derek Jantz (U.S. Pat. Nos. 10,093,899; 9,993,501; 9,950,010) against Roman Galetto (U.S. Appl. No. 16/027,629). Patent Interference No. 106,118. 8 pages.
Declaration of Interference filed Aug. 19, 2019 before the USPTO Patent Trial and Appeal Board on behalf of Derek Jantz (U.S. Pat. Nos. 10,093,900; 9,993,502; 9,969,975; 9,950,011; 9,889,161; 9,889,160) against Roman Galetto (U.S. Appl. No. 16/027,629). Patent Interference No. 106,117. 10 pages.
Deshayes et al., "Cell-penetrating peptides: tools for intracellular delivery of therapeutics," Cell Mol. Life Sci. 62, pp. 1839-1849 (2005).
Deshayes et al., "Primary amphipathic cell-penetrating peptides: structural requirements and interactions with model membranes," Biochemistry 43, pp. 7698-7706 (2004).
Dinda et al., "Nanobiotechnology-based drug delivery in brain targeting," Curr. Pharm. Biotechnol. 14, pp. 1264-1274 (2013).
Dingermann et al., "Establishment of a system for conditional gene expression using an inducible tRNA suppressor gene," Mol. Cell Biol. 12(9), pp. 4038-4045 (1992).
Durai et al., "Zinc finger nucleases: custom-designed molecular scissors for genome engineering of plant and mammalian cells," Nucleic Acids Res. 33, pp. 5978-5990 (2005).
Ellebrecht et al., "Reengineering chimeric antigen receptor T cells for targeted therapy of autoimmune disease," Science. Jul. 8, 2016;353(6295):179-84. doi: 10.1126/science.aaf6756. Epub Jun. 30, 2016. Author manuscript.
Eyquem et al., Targeting a CAR to theTRAC locus with CRISPR/CAS9 enhances tumour rejection. Nature. Mar. 2, 2017;543(7643):113-117. doi: 10.1038/nature21405. Epub Feb. 22, 2017.
Fu et al., "High-frequency off-target mutagenesis induced by CRISPR-Cas nucleases in human cells," Nat. Biotechnol. 31, pp. 822-826 (2013).
Galetto et al., Targeted approaches for gene therapy and the emergence of engineered meganucleases. Expert Opin Biol Ther. Oct. 2009;9(10):1289-303. doi: 10.1517/14712590903213669.
Gao et al., "Efficient gene delivery into mammalian cells mediated by a recombinant baculovirus containing a whispovirus ie1 promoter, a novel shuttle promoter between insect cells and mammalian cells," J. Biotechnol. 131(2), pp. 138-143 (2007).
Gish et al., "Identification of protein coding regions by database similarity search," Nature Genet. 3, pp. 266-272 (1993).
Grizot et al., "Efficient targeting of a SCID gene by an engineered single-chain homing endonuclease," Nucleic Acids Res. 37, pp. 5405-5419 (2009).
Haase, et al., "Generation of a tumor- and tissue-specific episomal non-viral vector system," BMC Biotechnol. 13, pp. 49-54 (2013).
Hale et al., "Homology-Directed Recombination for Enhanced Engineering of Chimeric Antigen Receptor T Cells," Molecular Therapy 4, pp. 192-203 (2017).
Handel et al., Versatile and efficient genome editing in human cells by combining zinc-finger nucleases with adeno-associated viral vectors. Hum Gene Ther. Mar. 2012;23(3):321-9. doi: 10.1089/hum.2011.140. Epub Dec. 14, 2011.
Hegde et al., "Current status of chimeric antigen receptor engineered T cell-based and immune checkpoint blockade-based cancer immunotherapies," Cancer Immunol Immunother 66, pp. 1113-1121 (2017).
Hudecz et al., "Medium-sized peptides as built in carriers for biologically active compounds," Med. Res. Rev. 25, pp. 679-736 (2005).
Ibarra et al., "Efficient Targeted Gene Modification in Primary Human Hematopoietic Cells Using Co-Delivery of Nuclease mRNA and AAV Donors," Mol. Ther., 23(suppl. 1), p. S273 (2015).
Imai et al., Chimeric receptors with 4-1BB signaling capacity provoke potent cytotoxicity against acute lymphoblastic leukemia. Leukemia. Apr. 2004;18(4):676-84.
Jacox et al., "Tissue-specific and ubiquitous expression patterns from alternative promoters of human genes," PLoS One 5(8), p. e12274 (2010).
Jearawiriyapaisam et al., "Sustained dystrophin expression induced by peptide-conjugated morpholino oligomers in the muscles of mdx mice," Mol. Ther. 16, pp. 1624-1629 (2008).
Jiang et al., "Cationic core-shell liponanoparticles for ocular gene delivery," Biomaterials. 33(30), pp. 7621-7630 (2012).
Kang et al., "Harnessing the capacity of cell-penetrating peptides for drug delivery to the central nervous system," Curr. Pharm. Biotechnol. 15(3), pp. 220-230 (2014).
Karlin et al., "Applications and statistics for multiple high-scoring segments in molecular sequences," Proc Natl Acad Sci U S A. Jun. 15, 1993;90(12):5873-7.
Koonin et al., Diversity, classification and evolution of CRISPR-Cas systems. Curr Opin Microbiol. Jun. 2017;37:67-78. doi: 10.1016/j.mib.2017.05.008. Epub Jun. 9, 2017.
Kramer et al., "In vitro and in vivo comparative study of chimeric liver-specific promoters," Mol. Ther. 7, pp. 375-385 (2003).
Kunkel et al., Rapid and efficient site-specific mutagenesis without phenotypic selection. Methods Enzymol. 1987;154:367-82. doi: 10.1016/0076-6879(87)54085-x.
Kunkel, "Rapid and efficient site-specific mutagenesis without phenotypic selection," Proc Natl Acad Sci U S A. Jan. 1985;82(2):488-92.
Lange et al., Classical nuclear localization signals: definition, function, and interaction with importin alpha. J Biol Chem. Feb. 23, 2007;282(8):5101-5. doi: 10.1074/jbc.R600026200. Epub Dec. 14, 2006.
Lee et al., "Efficient Generation of CART Cells by Homology Directed Transgene Integration into the TCR-Alpha Locus," Molecular Therapy, vol. 24, Supplement 1, S130 (May 2016).

(56) References Cited

OTHER PUBLICATIONS

Lentz, et al., "Viral vectors for gene delivery to the central nervous system," Neurobiol. Dis. 48, pp. 179-188 (2012).
Li et al., "Generation of single-chain LAGLIDADG homing endonucleases from native homodimeric precursor proteins," Nucleic Acids Res. 37, pp. 1650-1662 (2009).
Liu et al., "Therapeutic levels of factor IX expression using a muscle-specific promoter and adeno-associated virus serotype 1 vector," Hum. Gene Ther. 15, pp. 783-792 (2004).
Macleod et al., Generation of a Novel Allogeneic CAR T Cell Platform Utilizing an Engineered Meganuclease and AAV Donor Template to Achieve Efficient Disruption of T Cell Receptor Expression and Simultaneous Homology-Directed Insertion of a CD19 CAR. Mol Ther. May 1, 2016;24(S1):S156. Abstract.
Macleod et al., Integration of a CD19 CAR into the TCR Alpha Chain Locus Streamlines Production of Allogeneic Gene-Edited CAR T Cells. Molecular Therapy. Apr. 2017;25(4):949-961.
Madden et al., "Applications of network BLAST server," Meth. Enzymol. 266, pp. 131-141 (1996).
Mak et al., "TAL effectors: function, structure, engineering and applications," Curr. Opin. Struct. Biol. 23, pp. 93-99 (2013).
Mali et al., "Cas9 as a versatile tool for engineering biology," Nat. Methods 10, pp. 957-963 (2013).
Mao et al., "Comparison of nonhomologous end joining and homologous recombination in human cells," DNA Repair 7(10), pp. 1765-1771 (2008). Author's manuscript.
Martin et al., "Gene delivery to the eye using adeno-associated viral vectors," Methods 28, pp. 267-275 (2002).
Mastorakos et al., "Hydroxyl PAMAM dendrimer-based gene vectors for transgene delivery to human retinal pigment epithelial cells," Nanoscale 7(9), pp. 3845-3856 (2015).
McCall et al., "Pathogen-inspired drug delivery to the central nervous system," Tissue Barriers. 2(4), e944449; 12 pages (2014).
McCarty et al., "Self-complementary recombinant adeno-associated virus (scAAV) vectors promote efficient transduction independently of DNA synthesis," Gene Ther. 8, pp. 1248-1254 (2001).
Mishra et al., "Recent applications of liposomes in ophthalmic drug delivery," J. Drug Deliv. 2011, pp. 1-14 (2011).
Mombaerts et al., Mutations in T-cell antigen receptor genes alpha and beta block thymocyte development at different stages. Nature. Nov. 19, 1992;360(6401):225-31. Erratum in Nature Dec. 3, 1992;360(6403):491.
Morgan et al., "Genetic Modification of T Cells," Biomedicines 4, pp. 1-14 (2016).
Osborn et al., Evaluation of TCR Gene Editing Achieved by TALENs, CRISPR/Cas9, and megaTAL Nucleases. Mol Ther. Mar. 2016;24(3):570-81. doi: 10.1038/mt.2015.197. Epub Oct. 27, 2015.
Papapetrou et al., "Gene Insertion Into Genomic Safe Harbors for Human Gene Therapy," Molecular Therapy 24(4), pp. 678-684 (2016).
Pham et al., "Generation of CAR-T Cells Lacking T Cell Receptor and Human Leukocyte Antigen Using Engineered Meganucleases" Molecular Therapy, 24(suppl. 1), p. S78 (2016).
Poirot et al., "Multiplex Genome-Edited T-cell Manufacturing Platform for "Off-the-Shelf" Adoptive T-cell Immunotherapies," Cancer Research, 75(18), pp. 3853-3864 (2015).
Provasi et al., Editing T cell specificity towards leukemia by zinc finger nucleases and lentiviral gene transfer. Nat Med. May 2012;18(5):807-815. doi: 10.1038/nm.2700.
Qasim et al., "First Clinical Application of Talen Engineered Universal CAR19 T Cells in B-ALL," Blood 126(2046), pp. 1-3 (2015). Abstract only.
Qian et al., "Improved brain uptake of peptide-based CNS drugs via alternative routes of administrations of its nanocarrier delivery systems: a promising strategy for CNS targeting delivery of peptides," Expert Opin. Drug Metab. Toxicol. 10(11), (2014) 1491-1508.
Ran et al., "Genome engineering using the CRISPR-Cas9 system," Nat. Protoc. 8, pp. 2281-2308 (2013).
Reyon et al., "FLASH assembly of TALENs for high-throughput genome editing," Nat Biotechnol. May 2012;30(5):460-5. doi: 10.1038/nbt.2170. Author manuscript.
Rosenberg et al., Gene transfer into humans—immunotherapy of patients with advanced melanoma, using tumor-infiltrating lymphocytes modified by retroviral gene transduction. N Engl J Med. Aug. 30, 1990;323(9):570-8. doi: 10.1056/NEJM199008303230904.
Sadowski et al., The sequence-structure relationship and protein function prediction. Curr Opin Struct Biol. Jun. 2009;19(3):357-62. doi: 10.1016/j.sbi.2009.03.008. Epub May 4, 2009.
Sather et al., "Efficient modification of CCR5 in primary human hematopoietic cells using a megaTAL nuclease and AAV donor template," Science Translation Medicine. 7(307), pp. 1-14 (2015).
Seffernick et al., Melamine deaminase and atrazine chlorohydrolase: 98 percent identical but functionally different. J Bacteriol. Apr. 2001;183(8):2405-10.
Seligman et al., "Mutations altering the cleavage specificity of a homing endonuclease," Nucleic Acids Res. 30, pp. 3870-3879 (2002).
Sha et al., "Chimaeric antigen receptor T-cell therapy for tumour immunotherapy," Bioscience Reports 37, pp. 1-12 (2017).
Shao et al., Mechanisms for U2AF to define 3' splice sites and regulate alternative splicing in the human genome. Nat Struct Mol Biol. Nov. 2014;21(11):997-1005. doi: 10.1038/nsmb.2906. Epub Oct. 19, 2014.
Sharma et al., "Formulation and optimization of polymeric nanoparticles for intranasal delivery of lorazepam using Box-Behnken design: in vitro and in vivo evaluation," Biomed Res Int. 2014;2014:156010. doi: 10.1155/2014/156010. Epub Jul. 14, 2014.
Sharma et al., "Next generation delivery system for proteins and genes of therapeutic purpose: why and how?" Biomed Res Int. 2014;2014:327950. doi: 10.1155/2014/327950. Epub Jul. 15, 2014.
Simeoni et al., "Insight into the mechanism of the peptide-based gene delivery system MPG: implications for delivery of siRNA into mammalian cells," Nucleic Acids Res. 31, pp. 2717-2724 (2003).
Smith et al., A combinatorial approach to create artificial homing endonucleases cleaving chosen sequences. Nucleic Acids Res. 2006;34(22):e149. Epub Nov. 27, 2006.
Sowa et al., "In vitro and in vivo testing of a novel regulatory system for gene therapy for intervertebral disc degeneration," Spine, 36(10), pp. E623-E628 (2011).
Spear et al., "Strategies to genetically engineer T cells for cancer immunotherapy," Cancer Immunol Immunother. Jun. 2016;65(6):631-49. doi: 10.1007/s00262-016-1842-5. Epub May 2, 2016. Author manuscript.
Stoddard, Homing endonuclease structure and function. Q Rev Biophys. Feb. 2005;38(1):49-95. Epub Dec. 9, 2005.
Sussman et al., "Isolation and characterization of new homing endonuclease specificities at individual target site positions," J. Mol. Biol. 342, pp. 31-41 (2004).
Tamboli et al. Polymeric vectors for ocular gene delivery. Ther Deliv. Apr. 2011;2(4):523-36. doi: 10.4155/tde.11.20. Author manuscript.
Tammana et al., 4-1BB and CD28 signaling plays a synergistic role in redirecting umbilical cord blood T cells against B-cell malignancies. Hum Gene Ther. Jan. 2010;21(1):75-86. doi: 10.1089/hum.2009.122.
Tang et al., Identification of Dehalobacter reductive dehalogenases that catalyse dechlorination of chloroform, 1,1,1-trichloroethane and 1,1-dichloroethane. Philos Trans R Soc Lond B Biol Sci. Mar. 11, 2013;368(1616):20120318. doi: 10.1098/rstb.2012.0318.
Taylor et al., Apoptosis: controlled demolition at the cellular level. Nat Rev Mol Cell Biol. Mar. 2008;9(3):231-41. doi: 10.1038/nrm2312.
Thomsen et al., "Promoter-regulatory region of the major immediate early gene of human cytomegalovirus," Proc. Natl. Acad. Sci. USA 81(3), pp. 659-663 (1984).
Tong et al., "Eye drop delivery of nano-polymeric micelle formulated genes with cornea-specific promoters," J. Gene Med. 9(11), pp. 956-966 (2007).

(56) References Cited

OTHER PUBLICATIONS

Torikai et al., "A foundation for universal T-cell based immunotherapy: T cells engineered to express a CD19-specific chimeric-antigen-receptor and eliminate expression of endogenous TCR," Blood 119(24), pp. 5697-5705 (2012).

Torikai et al., Toward eliminating HLA class I expression to generate universal cells from allogeneic donors. Blood. Aug. 22, 2013;122(8):1341-9. doi: 10.1182/blood-2013-03-478255. Epub Jun. 5, 2013.

Van De Loo et al., An oleate 12-hydroxylase from *Ricinus communis* L. is a fatty acyl desaturase homolog. Proc Natl Acad Sci U S A. Jul. 18, 1995;92(15):6743-7. doi: 10.1073/pnas.92.15.6743.

Vannucci et al., "Viral vectors: a look back and ahead on gene transfer technology," New Microbiol. 36, pp. 1-22 (2013).

Witkowski et al., Conversion of a beta-ketoacyl synthase to a malonyl decarboxylase by replacement of the active-site cysteine with glutamine. Biochemistry. Sep. 7, 1999;38(36):11643-50.

Yoshikai et al., "Organization and sequences of the variable joining and constant region genes of the human t cell receptor alpha-chain," Nature, 316(6031), pp. 837-840 (1985).

Yuasa et al., "Adeno-associated virus vector-mediated gene transfer into dystrophin-deficient skeletal muscles evokes enhanced immune response against the transgene product," Gene Ther. 9, pp. 1576-1588 (2002).

Zhang et al., "A greedy algorithm for aligning DNA sequences," J. Comput. Biol. 7(1-2), pp. 203-214 (2000).

Zhang et al., "Engineering CAR-T cells," Biomarker Research 5(22), pp. 1-6 (2017).

Zuris et al., "Efficient Delivery of Genome-Editing Proteins In Vitro and In Vivo," Nat. Biotechnol. 33, pp. 73-80 (2015). Author's manuscript. Published online Oct. 30, 2014. doi: 10.1038/nbt.3081.

|                      | TRC1<br>Half-Site | TRC2<br>Half-Site |              |
|----------------------|-------------------|-------------------|--------------|
| TRC 1-2              | TGGCCTGGAGCAA | CAAATCTGA | SEQ ID NO:5 |
| Recognition Sequence | ACCGGACCT | CGTTGTTTAGACT | SEQ ID NO:6 |

FIGURE 1

A.
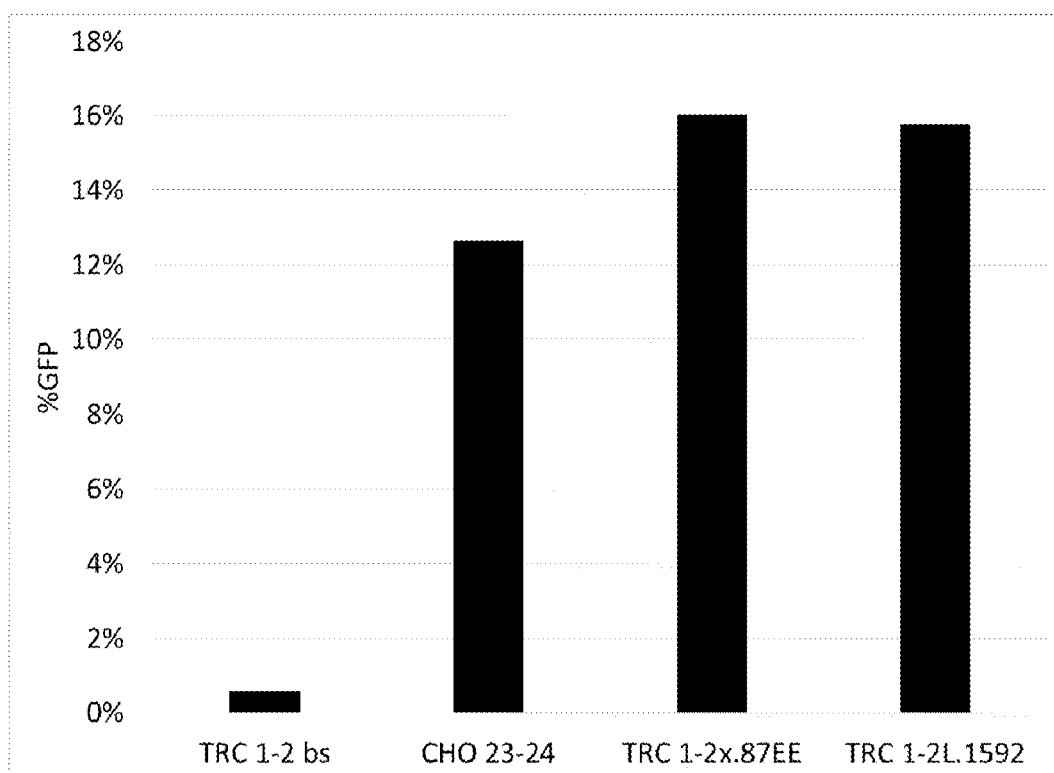
B.
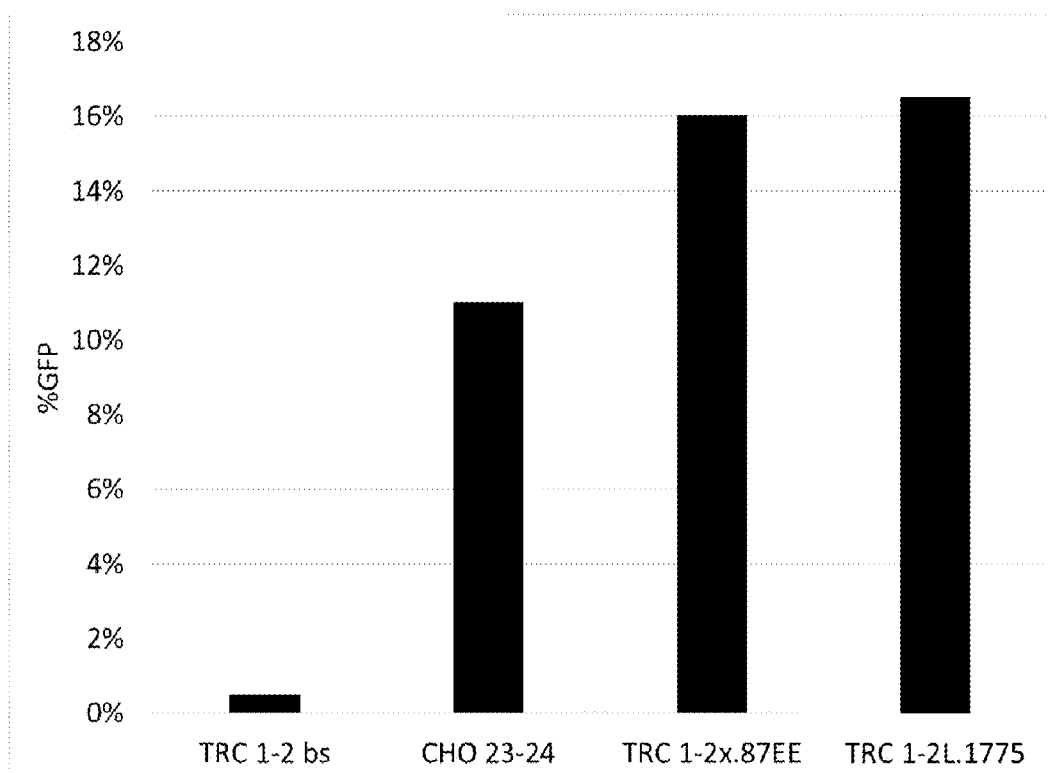
FIGURE 4

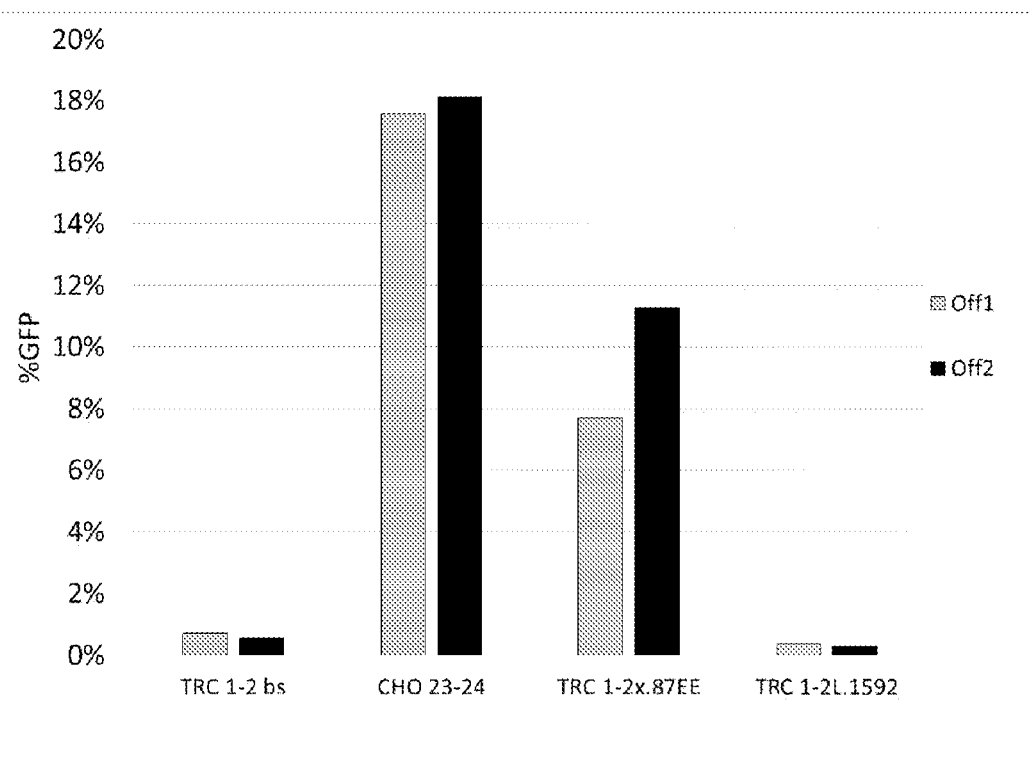
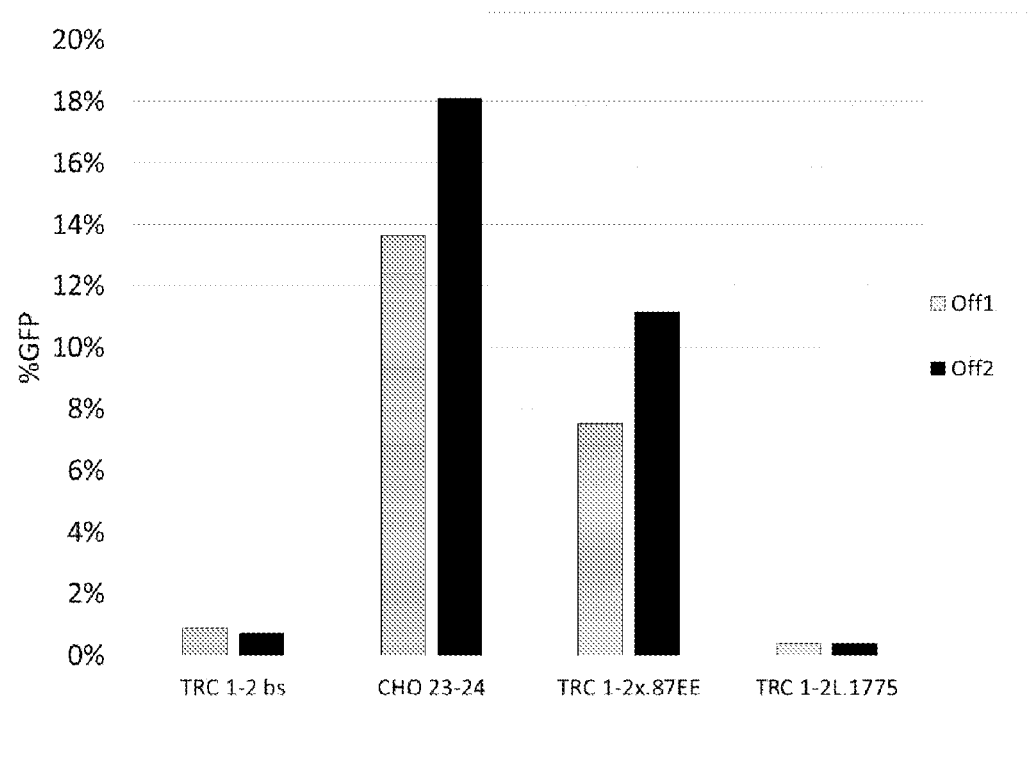
FIGURE 5

C.

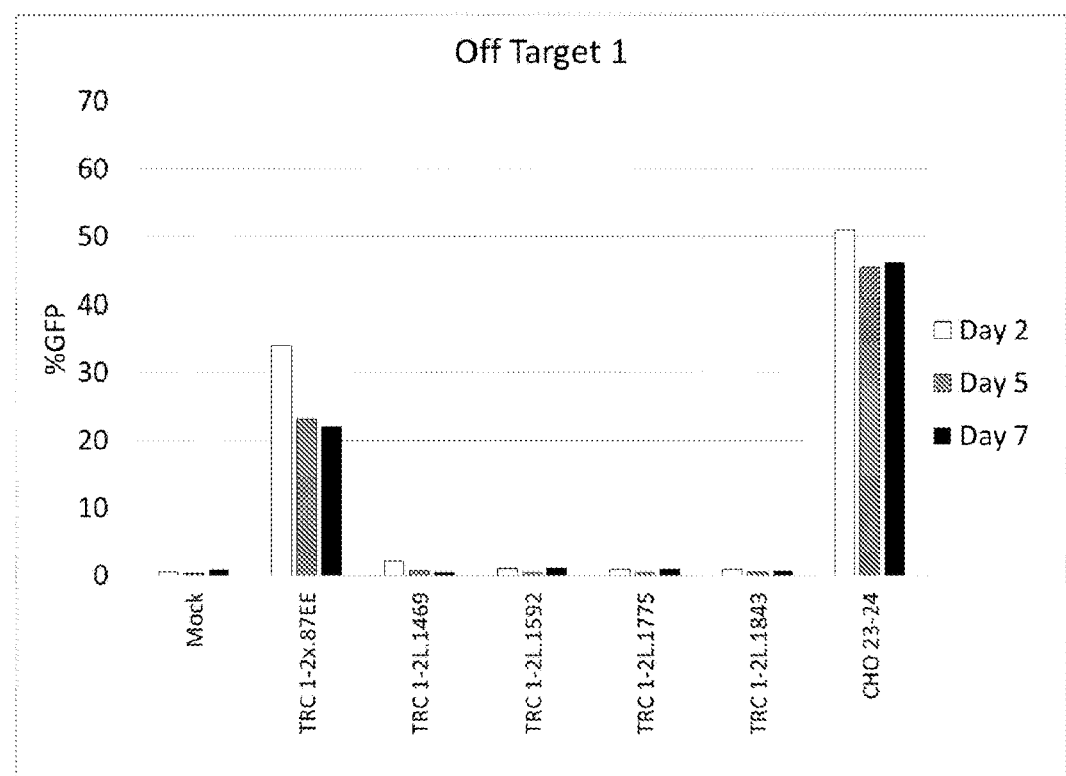
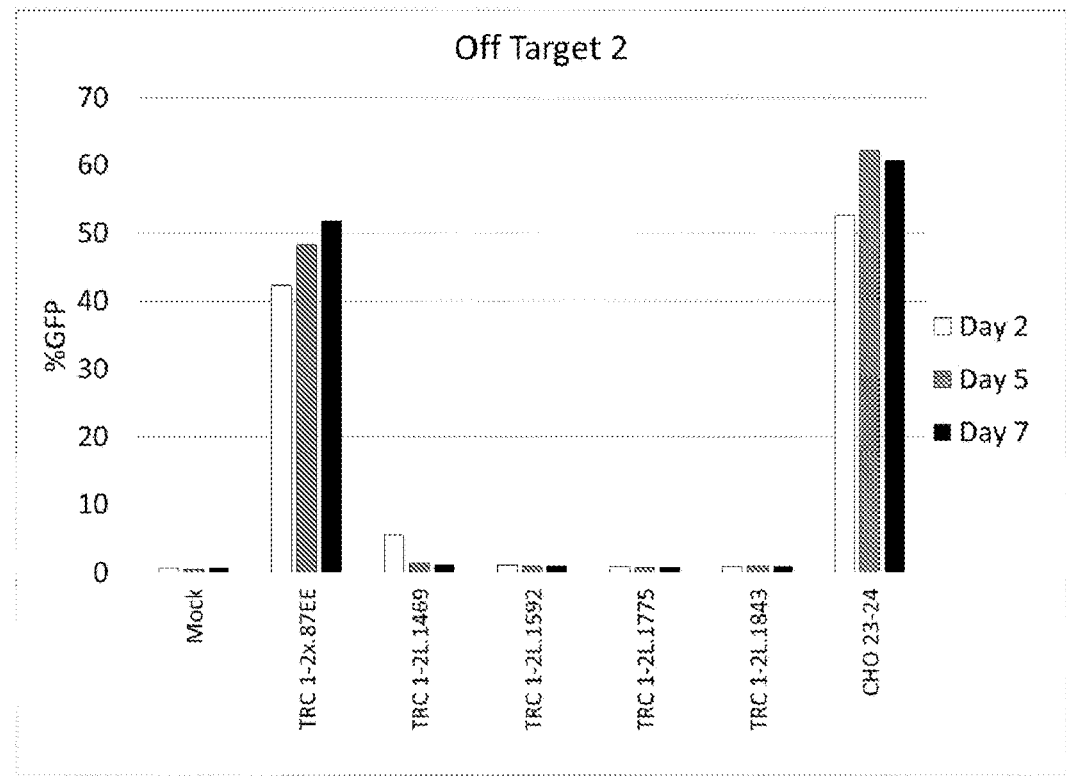
FIGURE 8

| Donor | Measurement | | Nuclease | | | | | Mock |
|---|---|---|---|---|---|---|---|---|
| | | | x.87EE | L.1469 | L.1592 | L.1775 | L.1843 | |
| K708 | CD3 knock out | | 65.60% | 40.10% | 63.90% | 66.40% | 45.10% | |
| | CD19 CAR knock in | | 41.50% | 21.50% | 42.20% | 44.40% | 28.10% | |
| | %CAR T | | 63.26% | 53.62% | 66.04% | 66.87% | 62.31% | |
| | Fold expansion | | 9.1 | 4.4 | 9.9 | 13.97 | 13.83 | |
| | Memory phenotype | Central | 82.91% | 80.51% | 91.82% | 90.72% | 91.05% | |
| | | Transitional | 13.73% | 12.67% | 6.13% | 6.87% | 6.86% | |
| | | Effector | 1.61% | 2.62% | 0.73% | 0.85% | 0.88% | |
| | CD4+:CD8+ ratio | CD4+ | 16.46% | 16.35% | 23.14% | 19.34% | 23.40% | |
| | | CD8+ | 81.05% | 79.97% | 74.41% | 78.05% | 73.97% | |
| K799 | CD3 knock out | | 59.90% | 40.50% | 60.40% | 64.10% | 37.90% | 0.30% |
| | CD19 CAR knock in | | 33.30% | 20.50% | 39.40% | 41.20% | 23.10% | 0.03% |
| | %CAR T | | 55.59% | 50.62% | 65.23% | 64.27% | 60.95% | |
| | Fold expansion | | 3.61 | 1.3 | 5.21 | 4.03 | 4.72 | |
| | Memory phenotype | Central | 90.04% | 60.75% | 92.62% | 90.85% | 91.48% | |
| | | Transitional | 5.75% | 24.93% | 4.87% | 6.05% | 6.00% | |
| | | Effector | 2.28% | 4.94% | 1.41% | 1.66% | 1.34% | |
| | CD4+:CD8+ ratio | CD4+ | 43.61% | 37.52% | 49.10% | 50.16% | 52.03% | |
| | | CD8+ | 54.68% | 59.13% | 49.52% | 48.35% | 46.42% | |
| K6784 | CD3 knock out | | 48.90% | 26.90% | 50.60% | 51.20% | 32.30% | |
| | CD19 CAR knock in | | 21.30% | 10.70% | 23.90% | 23.10% | 13.30% | |
| | %CAR T | | 43.56% | 39.78% | 47.23% | 45.12% | 41.18% | |
| | Fold expansion | | 4.87 | 1.6 | 9 | 8.6 | 15.7 | |
| | Memory phenotype | Central | 64.35% | 39.07% | 71.17% | 65.00% | 71.90% | |
| | | Transitional | 21.72% | 43.68% | 19.22% | 22.57% | 17.21% | |
| | | Effector | 8.70% | 9.38% | 5.89% | 7.61% | 6.45% | |
| | CD4+:CD8+ ratio | CD4+ | 48.89% | 51.47% | 51.75% | 42.52% | 42.26% | |
| | | CD8+ | 46.68% | 39.67% | 43.68% | 48.88% | 50.54% | |

FIGURE 11

A.
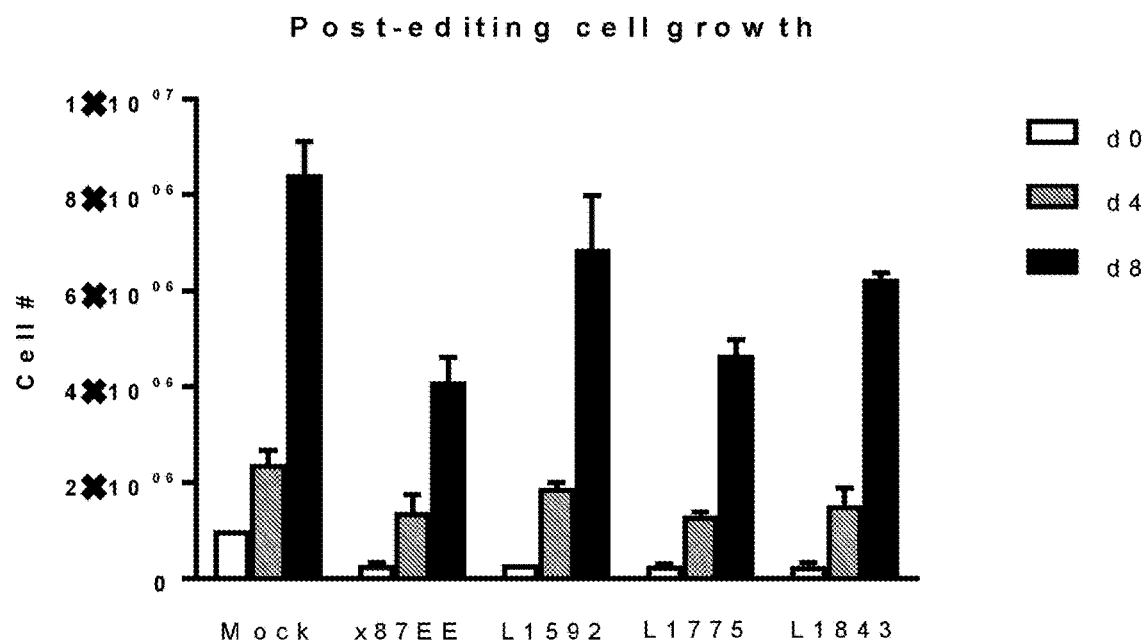
B.
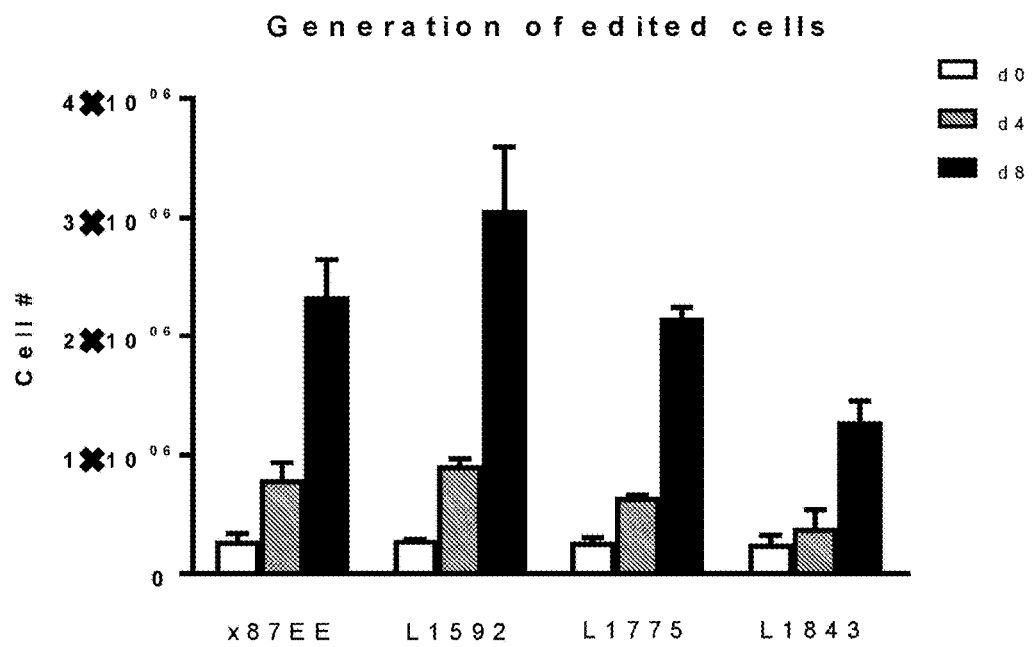
FIGURE 13

C.

A.
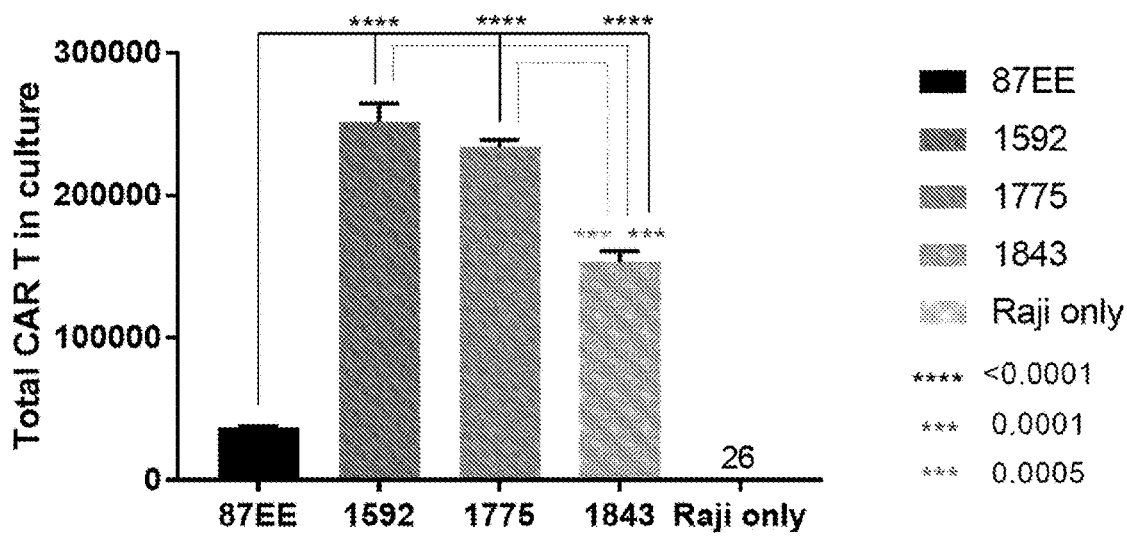
B.
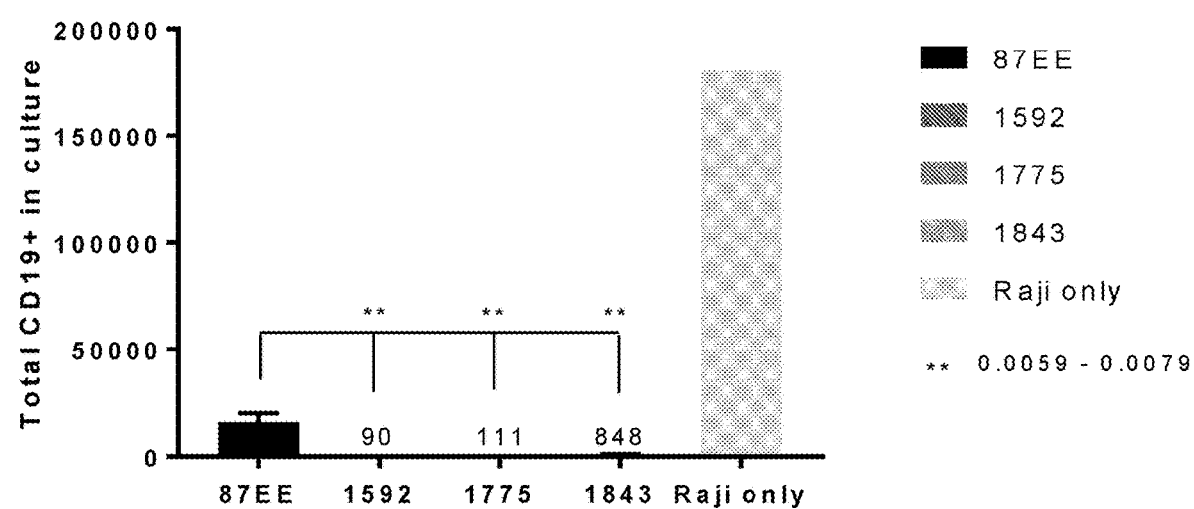
FIGURE 15

A.
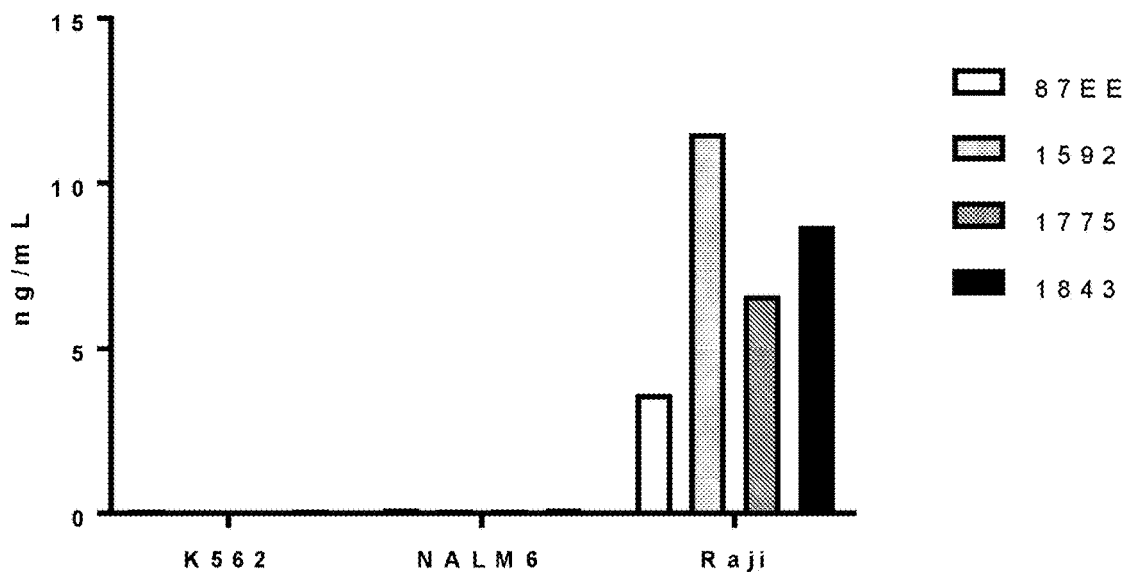
B.
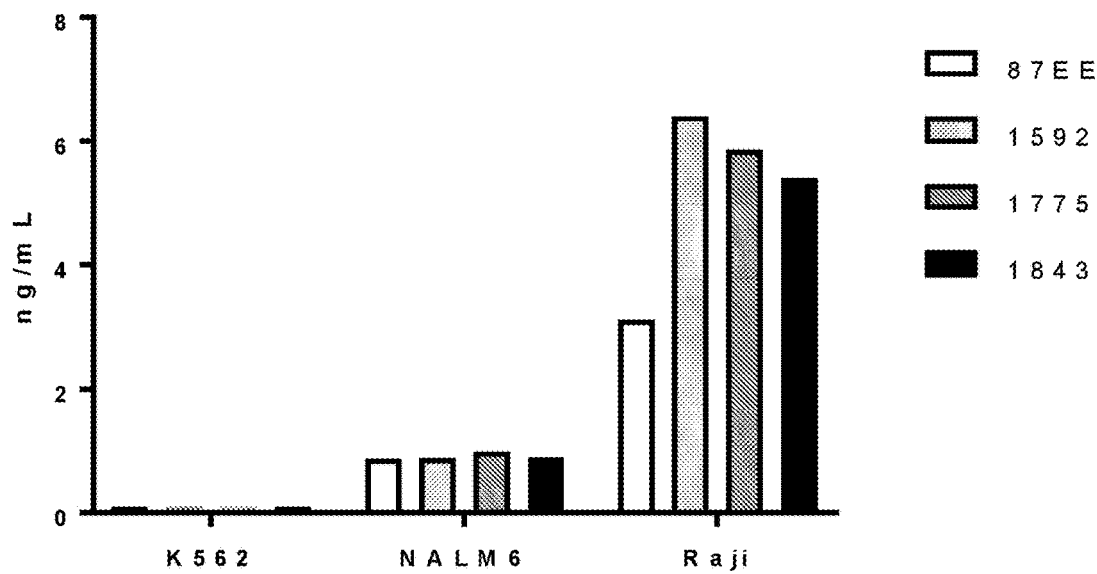
FIGURE 16

C.
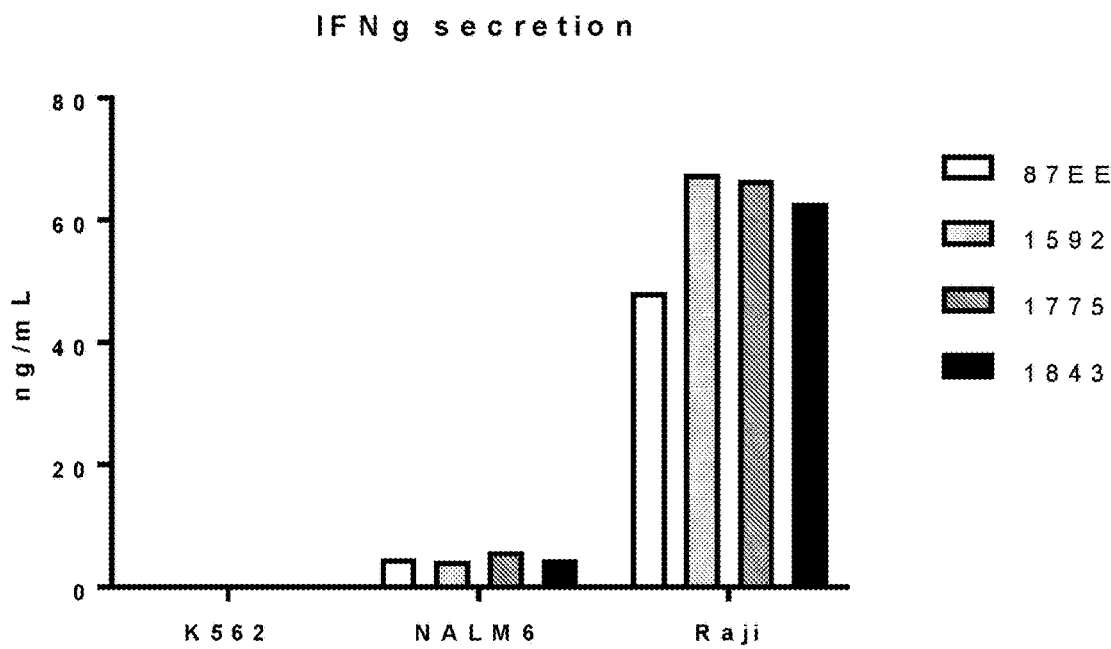
D.
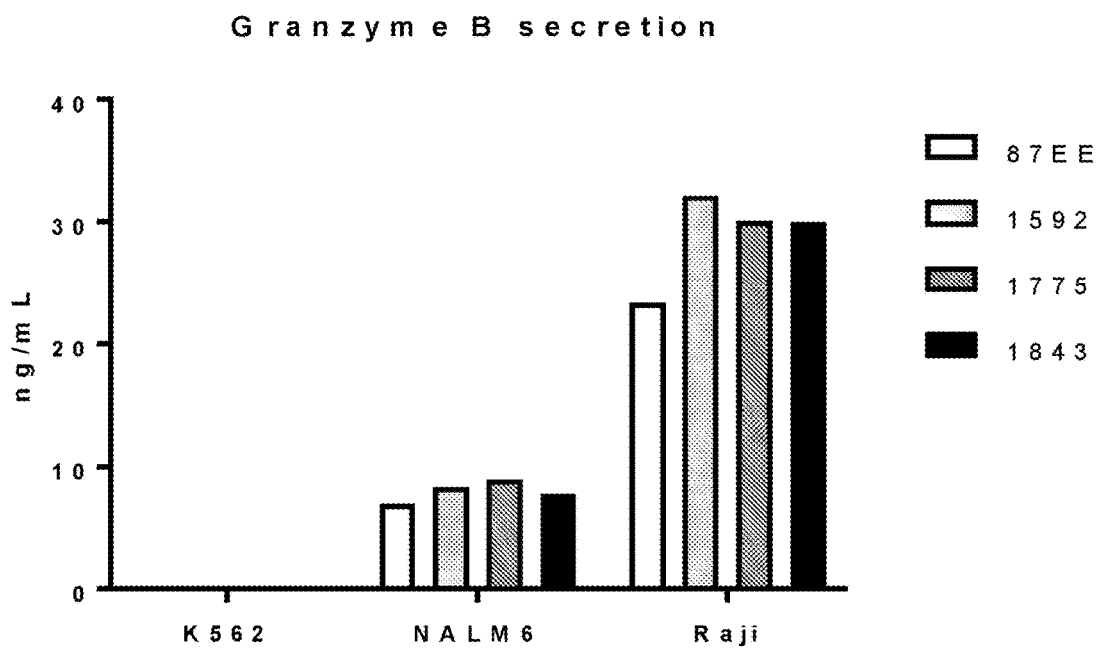
FIGURE 16 (cont.)

E.

SEQUENCE LISTING

```
<160> NUMBER OF SEQ ID NOS: 18

<210> SEQ ID NO 1
<211> LENGTH: 163
<212> TYPE: PRT
<213> ORGANISM: Chlamydomonas reinhardtii

<400> SEQUENCE: 1

Met Asn Thr Lys Tyr Asn Lys Glu Phe Leu Leu Tyr Leu Ala Gly Phe
1               5                   10                  15

Val Asp Gly Asp Gly Ser Ile Ile Ala Gln Ile Lys Pro Asn Gln Ser
            20                  25                  30

Tyr Lys Phe Lys His Gln Leu Ser Leu Ala Phe Gln Val Thr Gln Lys
        35                  40                  45

Thr Gln Arg Arg Trp Phe Leu Asp Lys Leu Val Asp Glu Ile Gly Val
    50                  55                  60

Gly Tyr Val Arg Asp Arg Gly Ser Val Ser Asp Tyr Ile Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Trp Arg Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Lys Thr Arg Lys Thr Thr
    130                 135                 140

Ser Glu Thr Val Arg Ala Val Leu Asp Ser Leu Ser Glu Lys Lys Lys
```

145            150            155            160

Ser Ser Pro

<210> SEQ ID NO 2
<211> LENGTH: 9
<212> TYPE: PRT
<213> ORGANISM: Chlamydomonas reinhardtii

<400> SEQUENCE: 2

Leu Ala Gly Leu Ile Asp Ala Asp Gly
1               5

<210> SEQ ID NO 3
<211> LENGTH: 4627
<212> TYPE: DNA
<213> ORGANISM: Homo sapiens

<400> SEQUENCE: 3

```
atatccagaa ccctgaccct gccgtgtacc agctgagaga ctctaaatcc agtgacaagt      60
ctgtctgcct attcaccgat tttgattctc aaacaaatgt gtcacaaagt aaggattctg     120
atgtgtatat cacagacaaa actgtgctag acatgaggtc tatggacttc aagagcaaca     180
gtgctgtggc ctggagcaac aaatctgact tgcatgtgc aaacgccttc aacaacagca      240
ttattccaga agacaccttc ttccccagcc aggtaagggg cagctttggt gccttcgcag     300
gctgttcct tgcttcagga atggccaggt tctgcccaga gctctggtca atgatgtcta      360
aaactcctct gattggtggt ctcggcctta tccattgcca ccaaaaccct cttttacta      420
agaaacagtg agccttgttc tggcagtcca gagaatgaca cgggaaaaaa gcagatgaag     480
agaaggtggc aggagagggc acgtggccca gcctcagtct ctccaactga gttcctgcct     540
gcctgccttt gctcagactg tttgcccctt actgctcttc taggcctcat tctaagcccc     600
ttctccaagt tgcctctcct tatttctccc tgtctgccaa aaaatctttc ccagctcact     660
aagtcagtct cacgcagtca ctcattaacc accaatcac tgattgtgcc ggcacatgaa      720
tgcaccaggt gttgaagtgg aggaattaaa aagtcagatg aggggtgtgc cagaggaag      780
caccattcta gttgggggag cccatctgtc agctgggaaa agtccaaata acttcagatt     840
ggaatgtgtt ttaactcagg gttgagaaaa cagctaccctt caggacaaaa gtcagggaag     900
ggctctctga agaaatgcta cttgaagata ccagccctac caagggcagg agaggaccc      960
tatagaggcc tgggacagga gctcaatgag aaaggagaag agcagcaggc atgagttgaa    1020
tgaaggaggc agggccgggt cacagggcct tctaggccat gagagggtag acagtattct    1080
aaggacgcca gaaagctgtt gatcggcttc aagcagggga gggacaccta atttgctttt    1140
cttttttttt ttttttttt tttttttttt tgagatggag ttttgctctt gttgcccagg    1200
ctggagtgca atggtgcatc ttggctcact gcaacctccg cctcccaggt tcaagtgatt    1260
ctcctgcctc agcctcccga gtagctgaga ttacaggcac cgccaccat gcctggctaa    1320
tttttttgtat ttttagtaga cagggtttt cactatgttg gccaggctgg tctcgaactc    1380
ctgacctcag gtgatccacc cgcttcagcc tcccaaagtg ctgggattac aggcgtgagc    1440
caccacaccc ggcctgcttt tcttaaagat caatctgagt gctgtacgga gagtgggttg    1500
taagccaaga gtagaagcag aaagggagca gttgcagcag agagatgatg gaggcctggg    1560
cagggtggtg gcagggaggt aaccaacacc attcaggttt caaaggtaga accatgcagg    1620
gatgagaaag caaagagggg atcaaggaag gcagctggat tttggcctga gcagctgagt    1680
```

```
caatgatagt gccgtttact aagaagaaac caaggaaaaa atttggggtg cagggatcaa    1740 aacttttttgg aacatatgaa agtacgtgtt tatactcttt atggcccttg tcactatgta    1800
tgcctcgctg cctccattgg actctagaat gaagccaggc aagagcaggg tctatgtgtg    1860
atggcacatg tggccagggt catgcaacat gtactttgta caaacagtgt atattgagta    1920
aatagaaatg gtgtccagga gccgaggtat cggtcctgcc agggccaggg gctctcccta    1980
gcaggtgctc atatgctgta agttccctcc agatctctcc acaaggaggc atggaaaggc    2040
tgtagttgtt cacctgccca agaactagga ggtctggggt gggagagtca gcctgctctg    2100
gatgctgaaa gaatgtctgt ttttccttttt agaaagttcc tgtgatgtca agctggtcga    2160
gaaaagcttt gaaacaggta agacaggggt ctagcctggg tttgcacagg attgcggaag    2220
tgatgaaccc gcaataaccc tgcctggatg agggagtggg aagaaattag tagatgtggg    2280
aatgaatgat gaggaatgga aacagcggtt caagacctgc ccagagctgg gtggggtctc    2340
tcctgaatcc ctctcaccat ctctgacttt ccattctaag cactttgagg atgagtttct    2400
agcttcaata gaccaaggac tctctcctag gcctctgtat tcctttcaac agctccactg    2460
tcaagagagc cagagagagc ttctgggtgg cccagctgtg aaatttctga gtcccttagg    2520
gatagcccta aacgaaccag atcatcctga ggacagccaa gaggttttgc cttctttcaa    2580
gacaagcaac agtactcaca taggctgtgg gcaatggtcc tgtctctcaa gaatcccctg    2640
ccactcctca cacccaccct gggcccatat tcatttccat ttgagttgtt cttattgagt    2700
catccttcct gtggtagcgg aactcactaa ggggcccatc tggacccgag gtattgtgat    2760
gataaattct gagcacctac cccatcccca aagggctcag aaataaaat aagagccaag    2820 tctagtcggt gtttcctgtc ttgaaacaca atactgttgg ccctggaaga atgcacagaa    2880
tctgtttgta aggggatatg cacagaagct gcaaggggaca ggaggtgcag gagctgcagg    2940
cctcccccac ccagcctgct ctgccttggg gaaaaccgtg ggtgtgtcct gcaggccatg    3000
caggcctggg acatgcaagc ccataaccgc tgtggcctct tggttttaca gatacgaacc    3060
taaactttca aaacctgtca gtgattgggt tccgaatcct cctcctgaaa gtggccgggt    3120
ttaatctgct catgacgctg cggctgtggt ccagctgagg tgaggggcct tgaagctggg    3180
agtggggttt agggacgcgg gtctctgggt gcatcctaag ctctgagagc aaacctccct    3240
gcagggtctt gcttttaagt ccaaagcctg agcccaccaa actctcctac ttcttcctgt    3300
tacaaattcc tcttgtgcaa taataatggc ctgaaacgct gtaaaatatc ctcatttcag    3360
ccgcctcagt tgcacttctc ccctatgagg taggaagaac agttgtttag aaacgaagaa    3420
actgaggccc cacagctaat gagtggagga agagagacac ttgtgtacac cacatgcctt    3480
gtgttgtact tctctcaccg tgtaacctcc tcatgtcctc tctccccagt acggctctct    3540
tagctcagta gaaagaagac attacactca tattacaccc caatcctggc tagagtctcc    3600
gcaccctcct cccccagggt ccccagtcgt cttgctgaca actgcatcct gttccatcac    3660
catcaaaaaa aaactccagg ctgggtgcgg ggctcacac ctgtaatccc agcactttgg    3720
gaggcagagg caggaggagc acaggagctg gagaccagcc tgggcaacac agggagaccc    3780
cgcctctaca aaaagtgaaa aaattaacca ggtgtggtgc tgcacacctg tagtcccagc    3840
tacttaagag gctgagatgg gaggatcgct tgagccctgg aatgttgagg ctacaatgag    3900
ctgtgattgc gtcactgcac tccagcctgg aagacaaagc aagatcctgt ctcaaataat    3960
aaaaaaaata gaactccag ggtacatttg ctcctgaaac tctaccacat agccccaaac    4020
agagccatca ccatcacatc cctaacagtc ctgggtcttc ctcagtgtcc agcctgactt    4080
```

```
ctgttcttcc tcattccaga tctgcaagat tgtaagacag cctgtgctcc ctcgctcctt    4140
cctctgcatt gccctcttc tccctctcca aacagaggga actctcctac ccccaaggag     4200
```

```
ctgttcttcc tcattccaga tctgcaagat tgtaagacag cctgtgctcc ctcgctcctt    4140
cctctgcatt gccctctt c tccctctcca aacagaggga actctcctac ccccaaggag    4200
gtgaaagctg ctaccacctc tgtgccccc  cggcaatgcc accaactgga tcctacccga    4260
atttatgatt aagattgctg aagagctgcc aaacactgct gccaccccct ctgttccctt    4320
attgctgctt gtcactgcct gacattcacg gcagaggcaa ggctgctgca gcctcccctg    4380
gctgtgcaca ttccctcctg ctccccagag actgcctccg ccatcccaca gatgatggat    4440
cttcagtggg ttctcttggg ctctaggtcc tgcagaatgt tgtgaggggt ttatttttt     4500 ttaatagtgt tcataaagaa atacatagta ttcttcttct caagacgtgg ggggaaatta    4560
tctcattatc gaggccctgc tatgctgtgt atctgggcgt gttgtatgtc ctgctgccga    4620
tgccttc                                                              4627
```

<210> SEQ ID NO 4
<211> LENGTH: 142
<212> TYPE: PRT
<213> ORGANISM: Homo sapiens

<400> SEQUENCE: 4

Pro Asn Ile Gln Asn Pro Asp Pro Ala Val Tyr Gln Leu Arg Asp Ser
1               5                   10                  15
Lys Ser Ser Asp Lys Ser Val Cys Leu Phe Thr Asp Phe Asp Ser Gln
            20                  25                  30
Thr Asn Val Ser Gln Ser Lys Asp Ser Asp Val Tyr Ile Thr Asp Lys
        35                  40                  45
Thr Val Leu Asp Met Arg Ser Met Asp Phe Lys Ser Asn Ser Ala Val
    50                  55                  60
Ala Trp Ser Asn Lys Ser Asp Phe Ala Cys Ala Asn Ala Phe Asn Asn
65                  70                  75                  80
Ser Ile Ile Pro Glu Asp Thr Phe Phe Pro Ser Pro Glu Ser Ser Cys
                85                  90                  95
Asp Val Lys Leu Val Glu Lys Ser Phe Glu Thr Asp Thr Asn Leu Asn
            100                 105                 110
Phe Gln Asn Leu Ser Val Ile Gly Phe Arg Ile Leu Leu Leu Lys Val
        115                 120                 125
Ala Gly Phe Asn Leu Leu Met Thr Leu Arg Leu Trp Ser Ser
    130                 135                 140

<210> SEQ ID NO 5
<211> LENGTH: 22
<212> TYPE: DNA
<213> ORGANISM: Homo sapiens

<400> SEQUENCE: 5
tggcctggag caacaaatct ga                                              22

<210> SEQ ID NO 6
<211> LENGTH: 22
<212> TYPE: DNA
<213> ORGANISM: Homo sapiens

<400> SEQUENCE: 6
accggacctc gttgtttaga ct                                              22

<210> SEQ ID NO 7
<211> LENGTH: 354

<212> TYPE: PRT
<213> ORGANISM: Artificial Sequence
<220> FEATURE:
<223> OTHER INFORMATION: Synthesized

<400> SEQUENCE: 7

Met Asn Thr Lys Tyr Asn Lys Glu Phe Leu Leu Tyr Leu Ala Gly Phe
1               5                   10                  15

Val Asp Gly Asp Gly Ser Ile Tyr Ala Val Ile Tyr Pro His Gln Arg
            20                  25                  30

Ala Lys Phe Lys His Phe Leu Lys Leu Leu Phe Thr Val Ser Gln Ser
        35                  40                  45

Thr Lys Arg Arg Trp Phe Leu Asp Lys Leu Val Asp Glu Ile Gly Val
50                  55                  60

Gly Tyr Val Tyr Asp Leu Pro Arg Thr Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Arg Pro Arg Gln Gly Ser
210                 215                 220

Lys Phe Lys His Arg Leu Thr Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 8
<211> LENGTH: 354
<212> TYPE: PRT

<213> ORGANISM: Artificial Sequence
<220> FEATURE:
<223> OTHER INFORMATION: Synthesized

<400> SEQUENCE: 8

```
Met Asn Thr Lys Tyr Asn Lys Glu Phe Leu Leu Tyr Leu Ala Gly Phe
1               5                   10                  15

Val Asp Gly Asp Gly Ser Ile Tyr Ala Cys Ile Tyr Pro His Gln Arg
            20                  25                  30

Ala Lys Phe Lys His Leu Leu Lys Leu Val Phe Ala Val His Gln Arg
        35                  40                  45

Thr Thr Arg Arg Trp Phe Leu Asp Lys Leu Val Asp Glu Ile Gly Val
    50                  55                  60

Gly Tyr Val Tyr Asp Ile Gly Ser Val Ser Glu Tyr Arg Leu Ser Gln
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
    130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Ser
            340                 345                 350

Ser Pro
```

<210> SEQ ID NO 9
<211> LENGTH: 354
<212> TYPE: PRT
<213> ORGANISM: Artificial Sequence
<220> FEATURE:
<223> OTHER INFORMATION: Synthesized

<400> SEQUENCE: 9

Met Asn Thr Lys Tyr Asn Lys Glu Phe Leu Leu Tyr Leu Ala Gly Phe
1               5                   10                  15

Val Asp Gly Asp Gly Ser Ile Phe Ala Ser Ile Tyr Pro His Gln Arg
            20                  25                  30

Ala Lys Phe Lys His Phe Leu Lys Leu Thr Phe Ala Val Tyr Gln Lys
        35                  40                  45

Thr Gln Arg Arg Trp Phe Leu Asp Lys Leu Val Asp Glu Ile Gly Val
    50                  55                  60

Gly Tyr Val Tyr Asp Ser Gly Ser Val Ser Glu Tyr Arg Leu Ser Glu
65                  70                  75                  80

Ile Lys Pro Leu His Asn Phe Leu Thr Gln Leu Gln Pro Phe Leu Lys
                85                  90                  95

Leu Lys Gln Lys Gln Ala Asn Leu Val Leu Lys Ile Ile Glu Gln Leu
            100                 105                 110

Pro Ser Ala Lys Glu Ser Pro Asp Lys Phe Leu Glu Val Cys Thr Trp
        115                 120                 125

Val Asp Gln Ile Ala Ala Leu Asn Asp Ser Arg Thr Arg Lys Thr Thr
130                 135                 140

Ser Glu Thr Val Arg Ala Val Leu Asp Ser Leu Pro Gly Ser Val Gly
145                 150                 155                 160

Gly Leu Ser Pro Ser Gln Ala Ser Ser Ala Ala Ser Ser Ala Ser Ser
                165                 170                 175

Ser Pro Gly Ser Gly Ile Ser Glu Ala Leu Arg Ala Gly Ala Gly Ser
            180                 185                 190

Gly Thr Gly Tyr Asn Lys Glu Phe Leu Leu Tyr Leu Ala Gly Phe Val
        195                 200                 205

Asp Gly Asp Gly Ser Ile Tyr Ala Cys Ile Ala Pro Arg Gln Gly Ser
    210                 215                 220

Lys Phe Lys His Arg Leu Lys Leu Gly Phe Ala Val Gly Gln Lys Thr
225                 230                 235                 240

Gln Arg Arg Trp Phe Leu Asp Lys Leu Val Asp Glu Ile Gly Val Gly
                245                 250                 255

Tyr Val Tyr Asp Arg Gly Ser Val Ser Glu Tyr Val Leu Ser Glu Ile
            260                 265                 270

Lys Pro Leu His Asn Phe Leu Thr Gln Leu Gln Pro Phe Leu Lys Leu
        275                 280                 285

Lys Gln Lys Gln Ala Asn Leu Val Leu Lys Ile Ile Glu Gln Leu Pro
    290                 295                 300

Ser Ala Lys Glu Ser Pro Asp Lys Phe Leu Glu Val Cys Thr Trp Val
305                 310                 315                 320

Asp Gln Ile Ala Ala Leu Asn Asp Ser Lys Thr Arg Lys Thr Thr Ser
                325                 330                 335

Glu Thr Val Arg Ala Val Leu Asp Ser Leu Ser Glu Lys Lys Lys Ser
            340                 345                 350

Ser Pro

<210> SEQ ID NO 10
<211> LENGTH: 147
<212> TYPE: PRT
<213> ORGANISM: Artificial Sequence
<220> FEATURE:

<223> OTHER INFORMATION: Synthesized

<400> SEQUENCE: 10

Lys Glu Phe Leu Leu Tyr Leu Ala Gly Phe Val Asp Gly Asp Gly Ser
1               5                   10                  15

Ile Tyr Ala Cys Ile Arg Pro Arg Gln Gly Ser Lys Phe Lys His Arg
            20                  25                  30

Leu Thr Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 11
<211> LENGTH: 147
<212> TYPE: PRT
<213> ORGANISM: Artificial Sequence
<220> FEATURE:
<223> OTHER INFORMATION: Synthesized

<400> SEQUENCE: 11

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
            85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
            115                 120                 125

Leu Asn Asp Ser Lys Thr Arg Lys Thr Thr Ser Glu Thr Val Arg Ala
    130                 135                 140

Val Leu Asp
145

<210> SEQ ID NO 12
<211> LENGTH: 147
<212> TYPE: PRT
<213> ORGANISM: Artificial Sequence
<220> FEATURE:
<223> OTHER INFORMATION: Synthesized

<400> SEQUENCE: 12

Lys Glu Phe Leu Leu Tyr Leu Ala Gly Phe Val Asp Gly Asp Gly Ser
1               5                   10                  15

Ile Tyr Ala Cys Ile Ala Pro Arg Gln Gly Ser Lys Phe Lys His Arg
            20                  25                  30

Leu Lys Leu Gly Phe Ala Val Gly Gln Lys Thr Gln Arg Arg Trp Phe
        35                  40                  45

Leu Asp Lys Leu Val Asp Glu Ile Gly Val Gly Tyr Val Tyr Asp Arg
    50                  55                  60

Gly Ser Val Ser Glu Tyr Val Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Lys Thr Arg Lys Thr Thr Ser Glu Thr Val Arg Ala
    130                 135                 140

Val Leu Asp
145

<210> SEQ ID NO 13
<211> LENGTH: 147
<212> TYPE: PRT
<213> ORGANISM: Artificial Sequence
<220> FEATURE:
<223> OTHER INFORMATION: Synthesized

<400> SEQUENCE: 13

Lys Glu Phe Leu Leu Tyr Leu Ala Gly Phe Val Asp Gly Asp Gly Ser
1               5                   10                  15

Ile Tyr Ala Val Ile Tyr Pro His Gln Arg Ala Lys Phe Lys His Phe
            20                  25                  30

Leu Lys Leu Leu Phe Thr Val Ser Gln Ser Thr Lys Arg Arg Trp Phe
        35                  40                  45

Leu Asp Lys Leu Val Asp Glu Ile Gly Val Gly Tyr Val Tyr Asp Leu
    50                  55                  60

Pro Arg Thr Ser Glu Tyr Arg Leu Ser Glu Ile Lys Pro Leu His Asn
65                  70                  75                  80

Phe Leu Thr Gln Leu Gln Pro Phe Leu Lys Leu Lys Gln Lys Gln Ala
                85                  90                  95

Asn Leu Val Leu Lys Ile Ile Glu Gln Leu Pro Ser Ala Lys Glu Ser
            100                 105                 110

Pro Asp Lys Phe Leu Glu Val Cys Thr Trp Val Asp Gln Ile Ala Ala
        115                 120                 125

Leu Asn Asp Ser Arg Thr Arg Lys Thr Thr Ser Glu Thr Val Arg Ala
    130                 135                 140

Val Leu Asp
145

<210> SEQ ID NO 14
<211> LENGTH: 147
<212> TYPE: PRT

<213> ORGANISM: Artificial Sequence
<220> FEATURE:
<223> OTHER INFORMATION: Synthesized

<400> SEQUENCE: 14

```
Lys Glu Phe Leu Leu Tyr Leu Ala Gly Phe Val Asp Gly Asp Gly Ser
1               5                   10                  15
Ile Tyr Ala Cys Ile Tyr Pro His Gln Arg Ala Lys Phe Lys His Leu
            20                  25                  30
Leu Lys Leu Val Phe Ala Val His Gln Arg Thr Thr Arg Arg Trp Phe
        35                  40                  45
Leu Asp Lys Leu Val Asp Glu Ile Gly Val Gly Tyr Val Tyr Asp Ile
    50                  55                  60
Gly Ser Val Ser Glu Tyr Arg Leu Ser Gln Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Arg Thr Arg Lys Thr Thr Ser Glu Thr Val Arg Ala
    130                 135                 140
Val Leu Asp
145
```

<210> SEQ ID NO 15
<211> LENGTH: 147
<212> TYPE: PRT
<213> ORGANISM: Artificial Sequence
<220> FEATURE:
<223> OTHER INFORMATION: Synthesized

<400> SEQUENCE: 15

```
Lys Glu Phe Leu Leu Tyr Leu Ala Gly Phe Val Asp Gly Asp Gly Ser
1               5                   10                  15
Ile Phe Ala Ser Ile Tyr Pro His Gln Arg Ala Lys Phe Lys His Phe
            20                  25                  30
Leu Lys Leu Thr Phe Ala Val Tyr Gln Lys Thr Gln Arg Arg Trp Phe
        35                  40                  45
Leu Asp Lys Leu Val Asp Glu Ile Gly Val Gly Tyr Val Tyr Asp Ser
    50                  55                  60
Gly Ser Val Ser Glu Tyr Arg Leu Ser Glu Ile Lys Pro Leu His Asn
65                  70                  75                  80
Phe Leu Thr Gln Leu Gln Pro Phe Leu Lys Leu Lys Gln Lys Gln Ala
                85                  90                  95
Asn Leu Val Leu Lys Ile Ile Glu Gln Leu Pro Ser Ala Lys Glu Ser
            100                 105                 110
Pro Asp Lys Phe Leu Glu Val Cys Thr Trp Val Asp Gln Ile Ala Ala
        115                 120                 125
Leu Asn Asp Ser Arg Thr Arg Lys Thr Thr Ser Glu Thr Val Arg Ala
    130                 135                 140
Val Leu Asp
145
```

<210> SEQ ID NO 16
<211> LENGTH: 22

```
<212> TYPE: DNA
<213> ORGANISM: Homo sapiens

<400> SEQUENCE: 16
tggcctggag aaacagtgta aa                                              22

<210> SEQ ID NO 17
<211> LENGTH: 22
<212> TYPE: DNA
<213> ORGANISM: Homo sapiens

<400> SEQUENCE: 17
cggcctgtag tacaggacct ga                                              22

<210> SEQ ID NO 18
<211> LENGTH: 42
<212> TYPE: PRT
<213> ORGANISM: Artificial Sequence
<220> FEATURE:
<223> OTHER INFORMATION: Synthesized

<400> SEQUENCE: 18

Ser Leu Pro Gly Ser Val Gly Gly Leu Ser Pro Ser Gln Ala Ser Ser
1               5                   10                  15

Ala Ala Ser Ser Ala Ser Ser Ser Pro Gly Ser Gly Ile Ser Glu Ala
            20                  25                  30

Leu Arg Ala Gly Ala Gly Ser Gly Thr Gly
        35                  40
```

OPTIMIZED ENGINEERED NUCLEASES HAVING SPECIFICITY FOR THE HUMAN T CELL RECEPTOR ALPHA CONSTANT REGION GENE

RELATED APPLICATIONS

This application is a national stage filing under 35 U.S.C. § 371 of international application number PCT/US2019/027019, filed Apr. 11, 2019, which claims the benefit of U.S. provisional application No. 62/656,809, filed Apr. 12, 2018, each of which is herein incorporated by reference in its entirety.

FIELD OF THE INVENTION

The invention relates to the field of oncology, cancer immunotherapy, molecular biology and recombinant nucleic acid technology. In particular, the invention relates to optimized engineered nucleases having specificity for a recognition sequence in the human T cell receptor alpha constant region gene. The invention further relates to the use of such recombinant meganucleases in methods for producing genetically-modified T cells as well as methods of using such cells for treating a disease, including cancer, in a subject.

REFERENCE TO A SEQUENCE LISTING SUBMITTED AS A TEXT FILE VIA EFS-WEB

The instant application contains a Sequence Listing which has been submitted in ASCII format via EFS-Web and is hereby incorporated by reference in its entirety. Said ASCII copy, created on Oct. 9, 2020, is named P109070028US01-SEQ-MJT, and is 27 kilobytes in size.

BACKGROUND OF THE INVENTION

T cell adoptive immunotherapy is a promising approach for cancer treatment. This strategy utilizes isolated human T cells that have been genetically-modified to enhance their specificity for a specific tumor associated antigen. Genetic modification may involve the expression of a chimeric antigen receptor or an exogenous T cell receptor to graft antigen specificity onto the T cell. By contrast to exogenous T cell receptors, chimeric antigen receptors derive their specificity from the variable domains of a monoclonal antibody. Thus, T cells expressing chimeric antigen receptors (CAR T cells) induce tumor immunoreactivity in a major histocompatibility complex non-restricted manner. T cell adoptive immunotherapy has been utilized as a clinical therapy for a number of cancers, including B cell malignancies (e.g., acute lymphoblastic leukemia, B cell non-Hodgkin lymphoma, acute myeloid leukemia, and chronic lymphocytic leukemia), multiple myeloma, neuroblastoma, glioblastoma, advanced gliomas, ovarian cancer, mesothelioma, melanoma, prostate cancer, pancreatic cancer, and others.

Despite its potential usefulness as a cancer treatment, adoptive immunotherapy with CAR T cells has been limited, in part, by expression of the endogenous T cell receptor on the cell surface. CAR T cells expressing an endogenous T cell receptor may recognize major and minor histocompatibility antigens following administration to an allogeneic patient, which can lead to the development of graft-versus-host-disease (GVHD). As a result, clinical trials have largely focused on the use of autologous CAR T cells, wherein a patient's T cells are isolated, genetically-modified to incorporate a chimeric antigen receptor, and then re-infused into the same patient. An autologous approach provides immune tolerance to the administered CAR T cells; however, this approach is constrained by both the time and expense necessary to produce patient-specific CAR T cells after a patient's cancer has been diagnosed.

Thus, it would be advantageous to develop "off the shelf" CAR T cells, prepared using T cells from a third party, healthy donor, that have reduced expression of the endogenous T cell receptor and do not initiate GVHD upon administration. Such products could be generated and validated in advance of diagnosis, and could be made available to patients as soon as necessary. Therefore, a need exists for the development of allogeneic CAR T cells that lack an endogenous T cell receptor in order to prevent the occurrence of GVHD.

Genetic modification of genomic DNA can be performed using site-specific, rare-cutting endonucleases that are engineered to recognize DNA sequences in the locus of interest. Homing endonucleases are a group of naturally-occurring nucleases that recognize 15-40 base-pair cleavage sites commonly found in the genomes of plants and fungi. They are frequently associated with parasitic DNA elements, such as group 1 self-splicing introns and inteins. They naturally promote homologous recombination or gene insertion at specific locations in the host genome by producing a double-stranded break in the chromosome, which recruits the cellular DNA-repair machinery (Stoddard (2006), Q. Rev. Biophys. 38: 49-95). Homing endonucleases are commonly grouped into four families: the LAGLIDADG (SEQ ID NO: 2) family, the GIY-YIG family, the His-Cys box family and the HNH family. These families are characterized by structural motifs, which affect catalytic activity and recognition sequence. For instance, members of the LAGLIDADG (SEQ ID NO: 2) family are characterized by having either one or two copies of the conserved LAGLIDADG (SEQ ID NO: 2) motif (see Chevalier et al. (2001), Nucleic Acids Res. 29(18): 3757-3774). The LAGLIDADG (SEQ ID NO: 2) homing endonucleases with a single copy of the LAGLIDADG (SEQ ID NO: 2) motif form homodimers, whereas members with two copies of the LAGLIDADG (SEQ ID NO: 2) motif are found as monomers.

I-CreI (SEQ ID NO: 1) is a member of the LAGLIDADG (SEQ ID NO: 2) family of homing endonucleases that recognizes and cuts a 22 basepair recognition sequence in the chloroplast chromosome of the algae Chlamydomonas reinhardtii. Genetic selection techniques have been used to modify the wild-type I-CreI cleavage site preference (Sussman et al. (2004), J. Mol. Biol. 342: 31-41; Chames et al. (2005), Nucleic Acids Res. 33: e178; Seligman et al. (2002), Nucleic Acids Res. 30: 3870-9, Arnould et al. (2006), J. Mol. Biol. 355: 443-58). More recently, a method of rationally-designing mono-LAGLIDADG (SEQ ID NO: 2) homing endonucleases was described that is capable of comprehensively redesigning I-CreI and other homing endonucleases to target widely-divergent DNA sites, including sites in mammalian, yeast, plant, bacterial, and viral genomes (WO 2007/047859).

As first described in WO 2009/059195, I-CreI and its engineered derivatives are normally dimeric but can be fused into a single polypeptide using a short peptide linker that joins the C-terminus of a first subunit to the N-terminus of a second subunit (Li et al. (2009), Nucleic Acids Res. 37:1650-62; Grizot et al. (2009), Nucleic Acids Res. 37:5405-19). Thus, a functional "single-chain" meganuclease can be expressed from a single transcript.

The use of nucleases for disrupting expression of the endogenous TCR has been disclosed, including the use of small-hairpin RNAs, zinc finger nucleases (ZFNs), transcription activator-like effector nucleases (TALENs), megaTALs, and CRISPR systems (e.g., Osborn et al. (2016), Molecular Therapy 24(3): 570-581; Eyquem et al. (2017), Nature 543: 113-117; U.S. Pat. No. 8,956,828; U.S. Publication No. US2014/0301990; U.S. Publication No. US2012/0321667).

The specific use of engineered meganucleases for cleaving DNA targets in the human TCR alpha constant region gene has also been previously disclosed. For example, International Publication No. WO 2014/191527 disclosed variants of the I-OnuI meganuclease that were also engineered to target a recognition sequence (SEQ ID NO: 3 of the '527 publication) within exon 1 of the TCR alpha constant region gene. Although the '527 publication discusses that a chimeric antigen receptor can be expressed in TCR knockout cells, the authors did not disclose the insertion of the CAR coding sequence into the meganuclease cleavage site.

Moreover, in International Publication Nos. WO 2017/062439 and WO 2017/062451, Applicants disclosed engineered meganucleases which have specificity for recognition sequences in exon 1 of the TCR alpha constant region gene. These included "TRC 1-2 meganucleases" which have specificity for the TRC 1-2 recognition sequence (SEQ ID NO: 5) in exon 1. The '439 and '451 publications also disclosed methods for targeted insertion of a CAR coding sequence or an exogenous TCR coding sequence into the TRC 1-2 meganuclease cleavage site.

In the present invention, Applicants have improved upon the nucleases and methods taught in the prior art. Through extensive experimentation, Applicants have generated novel, second-generation TRC 1-2 meganucleases which comprise unique, unpredictable combinations of residues and are unexpectedly superior to the first-generation TRC 1-2 meganucleases taught in the '439 and '451 applications. For example, the second-generation TRC 1-2 meganucleases of the invention possess improved (i.e., increased) specificity and reduced off-target cutting, exhibit reduced persistence time in cells following expression from mRNA, are functionally superior in vitro when used to generate CAR T cells (e.g., enhanced/increased TCR knock out, enhanced/increased CAR knock in, enhanced/increased CAR T expansion, improved CAR T cell phenotype, etc.), and produce improved CAR T cell populations when used in a full-scale CAR T cell manufacturing process.

SUMMARY OF THE INVENTION

The present invention provides engineered meganucleases that recognize and cleave recognition sequences within the first exon of the human T cell receptor (TCR) alpha constant region gene (SEQ ID NO: 3). Such meganucleases are useful for disrupting the TCR alpha constant region gene and, consequently, disrupting the expression and/or function of the cell surface TCR. Meganuclease cleavage can disrupt gene function either by the mutagenic action of non-homologous end joining or by promoting the introduction of an exogenous polynucleotide into the gene via homologous recombination. In some embodiments, the introduced exogenous polynucleotide comprises a nucleic acid sequence encoding a chimeric antigen receptor (CAR), such that the meganuclease is useful in generating an allogeneic CAR T cell that lacks an endogenous TCR. In some embodiments, the presently disclosed engineered meganucleases exhibit at least one optimized characteristic in comparison to the first-generation meganuclease TRC 1-2x.87EE. Such optimized characteristics include improved (i.e., increased) specificity resulting in reduced off-target cutting, reduced persistence time in cells (e.g., following expression from mRNA), and/or enhanced (i.e., increased) efficiency of modification of the TCR alpha constant region gene. Further, cells that have been genetically-modified with the presently disclosed engineered meganucleases exhibit improved characteristics, including reduced off-target cutting and effects thereof, reduced persistence time of the meganuclease in the cell, enhanced (i.e., increased) CAR T expansion, and are less differentiated as compared to cells that have been genetically-modified with the TRC1-2x.87EE meganuclease. In addition, populations of cells in which the presently disclosed meganucleases (or a nucleic acid encoding the same) have been introduced have a greater percentage of modified cells and a larger percentage of less differentiated cells when compared to those populations of cells in which the TRC 1-2x.87EE meganuclease (or a nucleic acid encoding the same) has been introduced.

The present invention further provides methods comprising the delivery of the engineered meganuclease protein, or genes encoding the engineered meganuclease, to a eukaryotic cell in order to produce a genetically-modified eukaryotic cell. Thus, genetically-modified eukaryotic cells and populations thereof, as well as pharmaceutical compositions comprising the genetically-modified eukaryotic cells and populations thereof, are further provided. Methods of immunotherapy for treating cancer by administering a genetically-modified T cell or populations thereof, wherein the T cell expresses a receptor for a tumor-specific antigen (e.g., a CAR or exogenous TCR) are also provided.

Thus, in one aspect, the invention provides an engineered meganuclease that recognizes and cleaves the TRC 1-2 recognition sequence (SEQ ID NO: 5) in exon 1 of the human TCR alpha constant region gene (SEQ ID NO: 3). The engineered meganuclease comprises a first subunit and a second subunit, wherein the first subunit binds to a first recognition half-site of the recognition sequence and comprises a first hypervariable (HVR1) region, and wherein the second subunit binds to a second recognition half site of the recognition sequence and comprises a second hypervariable (HVR2) region that has at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 of the presently disclosed TRC 1-2L.1592 (the amino acid sequence of which is set forth as SEQ ID NO: 7), or at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 of the presently disclosed TRC 1-2L.1775 meganuclease (the amino acid sequence of which is set forth as SEQ ID NO: 8).

In certain embodiments, HVR2 region comprises an amino acid sequence corresponding to residues 24-79 of SEQ ID NOs: 7 or 8 with up to 1, 2, 3, 4, 5, 6, 7, 8, 9, 10, or 11 amino acid substitutions.

In some embodiments, the HVR2 region comprises residues corresponding to residues 24, 26, 42, 44, 46, 48, 50, 70, 71, 72, and 73 of SEQ ID NO: 7.

In some embodiments, the HVR2 region comprises residues corresponding to residues 24, 26, 38, 42, 46, 48, 50, and 70 of SEQ ID NO: 8.

In some embodiments, the HVR2 region comprises residues corresponding to residues 24, 26, 28, 30, 32, 33, 38, 40, 42, 44, 46, 68, 70, 75, and 77 of SEQ ID NO: 7 or SEQ ID NO: 8.

In some embodiments, the HVR2 region comprises residues corresponding to residues 48, 50, 71, 72, and 73 of SEQ ID NO: 7.

In some embodiments, the HVR2 region comprises residues corresponding to residues 48 and 50 of SEQ ID NO: 8.

In some embodiments, the HVR2 region comprises residues corresponding to residues 24, 26, 28, 30, 32, 33, 38, 40, 42, 44, 46, 48, 50, 68, 70, 71, 72, 73, 75, and 77 of SEQ ID NO: 7 or SEQ ID NO: 8.

In some embodiments, the HVR2 region comprises Y, R, K, or D at a residue corresponding to residue 66 of SEQ ID NO: 7 or 8.

In certain embodiments, the HVR2 region comprises residues 24-79 of SEQ ID NO: 7 or 8.

In particular embodiments, the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of SEQ ID NO: 7 or 8. In some embodiments, the second subunit comprises an amino acid sequence having at least 93% sequence identity to an amino acid sequence corresponding to residues 7-153 of SEQ ID NO: 7. In some embodiments, the second subunit comprises an amino acid sequence having at least 94% sequence identity to an amino acid sequence corresponding to residues 7-153 of SEQ ID NO: 8.

In some embodiments, the second subunit comprises an amino acid sequence corresponding to residues 7-153 of SEQ ID NO: 7 or 8 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the second subunit comprises G, S, or A at a residue corresponding to residue 19 of SEQ ID NO: 7 or 8.

In certain embodiments, the second subunit comprises E, Q, or K at a residue corresponding to residue 80 of SEQ ID NO: 7 or 8.

In some embodiments, the second subunit comprises a residue corresponding to residue 80 of SEQ ID NO: 7 or 8.

In certain embodiments, the second subunit comprises a residue corresponding to residue 139 of SEQ ID NO: 7 or 8.

In particular embodiments, the second subunit comprises residues 7-153 of SEQ ID NO: 7 or 8.

In some such embodiments, the HVR1 region comprises an amino acid sequence having at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more, sequence identity to an amino acid sequence corresponding to residues 215-270 of SEQ ID NO: 7 or 8. In certain embodiments, the HVR1 region comprises an amino acid sequence corresponding to residues 215-270 of SEQ ID NO: 7 or 8 with up to 1, 2, 3, 4, 5, 6, 7, 8, 9, 10, or 11 amino acid substitutions.

In some embodiments, the HVR1 region comprises residues corresponding to residues 219 and 231 of SEQ ID NO: 7.

In certain embodiments, the HVR1 region comprises residues corresponding to residues 215, 217, 219, 221, 223, 224, 229, 231, 233, 235, 237, 259, 261, 266, and 268 of SEQ ID NO: 7 or 8.

In some embodiments, the HVR1 region comprises Y, R, K, or D at a residue corresponding to residue 257 of SEQ ID NO: 7 or 8.

In particular embodiments, the HVR1 region comprises residues 215-270 of SEQ ID NO: 7 or 8.

In some embodiments, the first subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of SEQ ID NO: 7 or 8. In certain embodiments, the first subunit comprises an amino acid sequence having at least 99% sequence identity to an amino acid sequence corresponding to residues 198-344 of SEQ ID NO: 7 or 8. In particular embodiments, the first subunit comprises an amino acid sequence corresponding to residues 198-344 of SEQ ID NOs: 7 or 8 with up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions.

In certain embodiments, the first subunit comprises G, S, or A at a residue corresponding to residue 210 of SEQ ID NO: 7 or 8.

In certain embodiments, the first subunit comprises E, Q, or K at a residue corresponding to residue 271 of SEQ ID NO: 7 or 8.

In certain embodiments, the first subunit comprises a residue corresponding to residue 271 of SEQ ID NO: 7 or 8.

In particular embodiments, the first subunit comprises residues 198-344 of SEQ ID NO: 7 or 8.

In some embodiments, the first subunit of the engineered meganuclease has at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 198-344 of SEQ ID NO: 7 or 8 and the second subunit comprises an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 7-153 of SEQ ID NO: 7 or 8. In particular embodiments, the first subunit of the engineered meganuclease has at least 99% sequence identity to an amino acid sequence corresponding to residues 198-344 of SEQ ID NO: 7 or 8, and the second subunit comprises an amino acid sequence having at least 93% sequence identity to an amino acid sequence corresponding to residues 7-153 of SEQ ID NO: 7 or 8. In certain embodiments, the first subunit and/or the second subunit can comprise up to 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 amino acid substitutions relative to residues 198-344 and residues 7-153, respectively, of SEQ ID NO: 7 and 8.

In certain embodiments, the engineered meganuclease comprises a linker, wherein the linker covalently joins the first subunit and the second subunit.

In some embodiments, the engineered meganuclease comprises an amino acid sequence having at least about 90%, 91%, 92%, 93%, 94%, 95%, 96%, 97%, 98%, or 99% sequence identity to the amino acid sequence of SEQ ID NO: 7 or 8. In certain embodiments, the engineered meganuclease comprises an amino acid sequence having at least 97% sequence identity to the amino acid sequence of SEQ ID NO: 7. In certain embodiments, the engineered meganuclease comprises an amino acid sequence having at least 98% sequence identity to the amino acid sequence of SEQ ID NO: 8.

In particular embodiments, the engineered meganuclease comprises the amino acid sequence of SEQ ID NO: 7 or 8.

In certain embodiments, the engineered meganuclease exhibits at least one of the following optimized characteristics as compared to TRC 1-2x.87EE meganuclease set forth as SEQ ID NO: 9: improved (i.e., increased) specificity, reduced persistence time in cells, and enhanced (i.e., increased) efficiency of modification of the human TCR alpha constant region gene.

In particular embodiments, the engineered meganuclease that recognizes and cleaves a recognition sequence comprising SEQ ID NO: 5 within a human TCR alpha constant region gene comprises a first and a second subunit, wherein the first subunit comprises: (a) an amino acid sequence having at least 80%, at least 85%, at least 90%, at least 95%, or more, sequence identity to residues 198-344 of SEQ ID NO: 7 or 8; and (b) an HVR1 region having at least 80%, at least 85%, at least 90%, at least 95%, or more, sequence identity to an amino acid sequence corresponding to residues 215-270 of SEQ ID NO: 7 or 8; and wherein the second subunit comprises: (a) an amino acid sequence having at least 80%, at least 85%, at least 90%, at least 95%, or more, sequence identity to residues 7-153 of SEQ ID NO: 7 or 8; and (b) an HVR2 region having at least 80%, at least 85%, at least 90%, at least 95%, or more, sequence identity to an amino acid sequence corresponding to residues 24-79 of SEQ ID NO: 7 or 8.

In particular embodiments, the engineered meganuclease that recognizes and cleaves a recognition sequence comprising SEQ ID NO: 5 within a human TCR alpha constant region gene comprises a first and a second subunit, wherein the first subunit comprises: (a) an amino acid sequence having at least 80%, at least 85%, at least 90%, at least 95%, or more, sequence identity to residues 198-344 of SEQ ID NO: 7 or 8; and (b) an HVR1 region having at least 80%, at least 85%, at least 90%, at least 95%, or more, sequence identity to an amino acid sequence corresponding to residues 215-270 of SEQ ID NO: 7 or 8, and comprising residues corresponding to residues 215, 217, 219, 221, 223, 224, 229, 231, 233, 235, 237, 259, 261, 266, and 268 of SEQ ID NO: 7 or 8; and wherein the second subunit comprises: (a) an amino acid sequence having at least 80%, at least 85%, at least 90%, at least 95%, or more, sequence identity to residues 7-153 of SEQ ID NO: 7 or 8; and (b) an HVR2 region having at least 80%, at least 85%, at least 90%, at least 95%, or more, sequence identity to an amino acid sequence corresponding to residues 24-79 of SEQ ID NO: 7 or 8, and comprising residues corresponding to residues 24, 26, 28, 30, 32, 33, 38, 40, 42, 44, 46, 68, 70, 75, and 77 of SEQ ID NO: 7 or 8. In such embodiments, the HVR2 region can further comprise residues corresponding to residues 48, 50, 71, 72, and 73 of SEQ ID NO: 7 and/or residues corresponding to residues 48 and 50 of SEQ ID NO: 8.

In particular embodiments, the engineered meganuclease that recognizes and cleaves a recognition sequence comprising SEQ ID NO: 5 within a human TCR alpha constant region gene comprises a first and a second subunit, wherein the first subunit comprises: (a) an amino acid sequence having at least 80%, at least 85%, at least 90%, at least 95%, or more, sequence identity to residues 198-344 of SEQ ID NO: 7 or 8; and (b) an HVR1 region having at least 80%, at least 85%, at least 90%, at least 95%, or more, sequence identity to an amino acid sequence corresponding to residues 215-270 of SEQ ID NO: 7 or 8, and comprising residues corresponding to residues 215, 217, 219, 221, 223, 224, 229, 231, 233, 235, 237, 259, 261, 266, and 268 of SEQ ID NO: 7 or 8; and wherein the second subunit comprises: (a) an amino acid sequence having at least 80%, at least 85%, at least 90%, at least 95%, or more, sequence identity to residues 7-153 of SEQ ID NO: 7 or 8; and (b) an HVR2 region having at least 80%, at least 85%, at least 90%, at least 95%, or more, sequence identity to an amino acid sequence corresponding to residues 24-79 of SEQ ID NO: 7 or 8, and comprising residues corresponding to residues 24, 26, 28, 30, 32, 33, 38, 40, 42, 44, 46, 48, 50, 68, 70, 71, 72, 73, 75, and 77 of SEQ ID NO: 7 or 8.

In still other embodiments, the engineered meganuclease that recognizes and cleaves a recognition sequence comprising SEQ ID NO: 5 within a human TCR alpha constant region gene comprises a first and a second subunit, wherein the first subunit comprises: (a) an amino acid sequence having at least 80%, at least 85%, at least 90%, at least 95%, or more, sequence identity to residues 198-344 of SEQ ID NO: 7 or 8; and (b) an HVR1 region having an amino acid sequence corresponding to residues 215-270 of SEQ ID NO: 7 or 8; and wherein the second subunit comprises: (a) an amino acid sequence having at least 80%, at least 85%, at least 90%, at least 95%, or more, sequence identity to residues 7-153 of SEQ ID NO: 7 or 8; and (b) a HVR2 region having an amino acid sequence corresponding to residues 24-79 of SEQ ID NO: 7 or 8.

In another aspect, the invention provides a polynucleotide comprising a nucleic acid sequence encoding an engineered meganuclease described herein.

In certain embodiments, the polynucleotide is an mRNA.

In further embodiments, the mRNA is a polycistronic mRNA encoding an engineered meganuclease described herein and at least one additional polypeptide or nucleic acid.

In another aspect, the invention provides a recombinant DNA construct comprising the polynucleotide described herein.

In certain embodiments, the recombinant DNA construct encodes a viral vector. In particular embodiments, the viral vector is an adenoviral vector, a lentiviral vector, a retroviral vector, or an adeno-associated viral (AAV) vector. In specific embodiments, the viral vector is a recombinant AAV vector.

In another aspect, the invention provides a viral vector comprising the polynucleotide described herein.

In certain embodiments, the viral vector is an adenoviral vector, a lentiviral vector, a retroviral vector, or an AAV vector. In particular embodiments, the viral vector is a recombinant AAV vector.

In another aspect, the invention provides a method for producing a genetically-modified eukaryotic cell comprising an exogenous sequence of interest inserted into a chromosome of the eukaryotic cell. The method comprises introducing into a eukaryotic cell one or more nucleic acids including: (a) a first nucleic acid encoding an engineered meganuclease described herein, wherein the engineered meganuclease is expressed in the eukaryotic cell; and (b) a second nucleic acid including the sequence of interest; wherein the engineered meganuclease produces a cleavage site in the chromosome at a recognition sequence comprising SEQ ID NO: 5; and wherein the sequence of interest is inserted into the chromosome at the cleavage site.

In certain embodiments of the method, the second nucleic acid further comprises sequences homologous to sequences flanking the cleavage site and the sequence of interest is inserted at the cleavage site by homologous recombination.

In certain embodiments of the method, the second nucleic acid does not comprise sequences homologous to sequences flanking the cleavage site and the sequence of interest is inserted at the cleavage site by non-homologous insertion.

In certain embodiments of the method, cell surface expression of an endogenous T cell receptor (e.g., an alpha/beta T cell receptor) is reduced when compared to an unmodified control cell.

In some embodiments of the method, the eukaryotic cell is a human T cell, or a cell derived therefrom or a human NK cell, or a cell derived therefrom.

In some embodiments of the method, the sequence of interest comprises a coding sequence for a chimeric antigen receptor or an exogenous T cell receptor. In particular embodiments of the method, the chimeric antigen receptor or the exogenous T cell receptor comprises an extracellular ligand-binding domain having specificity for a tumor-specific antigen.

In some embodiments of the method, at least the first nucleic acid is introduced into the eukaryotic cell by an mRNA.

In certain embodiments of the method, at least the second nucleic acid is introduced into the eukaryotic cell by a viral vector. In particular embodiments of the method, the viral vector is an adenoviral vector, a lentiviral vector, a retroviral vector, or an AAV vector. In specific embodiments of the method, the viral vector is a recombinant AAV vector.

In another aspect, the invention provides a method for producing a genetically-modified eukaryotic cell comprising an exogenous sequence of interest inserted into a chromosome of the eukaryotic cell. The method comprises: (a) introducing an engineered meganuclease described herein into a eukaryotic cell; and (b) introducing a nucleic acid including the sequence of interest into the eukaryotic cell; wherein the engineered meganuclease produces a cleavage site in the chromosome at a recognition sequence comprising SEQ ID NO: 5; and wherein the sequence of interest is inserted into the chromosome at the cleavage site.

In certain embodiments of the method, the nucleic acid further comprises sequences homologous to sequences flanking the cleavage site and the sequence of interest is inserted at the cleavage site by homologous recombination.

In certain embodiments of the method, the nucleic acid does not comprise sequences homologous to sequences flanking the cleavage site and the sequence of interest is inserted at the cleavage site by non-homologous insertion.

In certain embodiments of the method, cell surface expression of an endogenous T cell receptor (e.g., an alpha/beta T cell receptor) is reduced when compared to an unmodified control cell.

In some embodiments of the method, the eukaryotic cell is a human T cell, or a cell derived therefrom, or a human NK cell, or a cell derived therefrom.

In some embodiments of the method, the sequence of interest comprises a coding sequence for a chimeric antigen receptor or an exogenous T cell receptor. In particular embodiments of the method, the chimeric antigen receptor or the exogenous T cell receptor comprises an extracellular ligand-binding domain having specificity for a tumor-specific antigen.

In certain embodiments of the method, the nucleic acid is introduced into the eukaryotic cell by a viral vector. In particular embodiments of the method, the viral vector is an adenoviral vector, a lentiviral vector, a retroviral vector, or an AAV vector. In specific embodiments of the method, the viral vector is a recombinant AAV vector.

In another aspect, the invention provides a method for producing a genetically-modified eukaryotic cell by disrupting a target sequence in a chromosome of the eukaryotic cell. The method comprises introducing into a eukaryotic cell a nucleic acid encoding an engineered meganuclease described herein, wherein the engineered meganuclease is expressed in the eukaryotic cell, and wherein the engineered meganuclease produces a cleavage site in the chromosome at a recognition sequence comprising SEQ ID NO: 5, and wherein the target sequence is disrupted by non-homologous end-joining at the cleavage site.

In certain embodiments of the method, cell surface expression of an endogenous T cell receptor (e.g., an alpha/beta T cell receptor) is reduced when compared to an unmodified control cell.

In some embodiments of the method, the eukaryotic cell is a human T cell, or a cell derived therefrom, or a human NK cell, or a cell derived therefrom.

In some embodiments of the method, the nucleic acid is introduced into the eukaryotic cell by an mRNA.

In another aspect, the invention provides a method for producing a genetically-modified eukaryotic cell by disrupting a target sequence in a chromosome of the eukaryotic cell. The method comprises introducing into a eukaryotic cell an engineered meganuclease described herein, wherein the engineered meganuclease produces a cleavage site in the chromosome at a recognition sequence comprising SEQ ID NO: 5, and wherein the target sequence is disrupted by non-homologous end-joining at the cleavage site.

In certain embodiments of the method, cell surface expression of an endogenous T cell receptor (e.g., an alpha/beta T cell receptor) is reduced when compared to an unmodified control cell.

In some embodiments of the method, the eukaryotic cell is a human T cell, or a cell derived therefrom, or a human NK cell, or a cell derived therefrom.

In another aspect, the invention provides a genetically-modified eukaryotic cell comprising in its genome a modified human T cell receptor alpha constant region gene, wherein the modified human T cell receptor alpha constant region gene comprises an exogenous sequence of interest inserted into exon 1 within SEQ ID NO: 5 within the T cell receptor alpha constant region, and wherein the genetically-modified eukaryotic cell is prepared by a method described herein using an engineered meganuclease described herein.

In certain embodiments, the genetically-modified eukaryotic cell is a genetically-modified human T cell, or a cell derived therefrom, or a human NK cell, or a cell derived therefrom.

In certain embodiments, the sequence of interest comprises a coding sequence for a chimeric antigen receptor or an exogenous T cell receptor. In particular embodiments, the chimeric antigen receptor or the exogenous T cell receptor comprises an extracellular ligand-binding domain having specificity for a tumor-specific antigen.

In particular embodiments, the cell surface expression of an endogenous T cell receptor (e.g., an alpha/beta T cell receptor) is reduced on the genetically-modified eukaryotic cell when compared to an unmodified control cell.

In particular embodiments, the genetically-modified eukaryotic cell comprises reduced off-target effects by the engineered meganuclease, and/or reduced persistence time of the engineered meganuclease in the cell as compared to TRC 1-2x.87EE meganuclease set forth as SEQ ID NO: 9.

In another aspect, the invention provides a genetically-modified eukaryotic cell comprising a chromosome with a disrupted target sequence at a recognition sequence comprising SEQ ID NO: 5, wherein the target sequence is disrupted by non-homologous end-joining at the cleavage site, and wherein the genetically-modified eukaryotic cell is prepared by a method described herein using an engineered meganuclease described herein.

In certain embodiments, the genetically-modified eukaryotic cell is a genetically-modified human T cell, or a cell derived therefrom, or a human NK cell, or a cell derived therefrom.

In particular embodiments, the cell surface expression of an endogenous T cell receptor (e.g., an alpha/beta T cell receptor) is reduced on the genetically-modified eukaryotic cell when compared to an unmodified control cell.

In particular embodiments, the genetically-modified eukaryotic cell comprises reduced off-target effects by the engineered meganuclease, and/or reduced persistence time in the cell as compared to TRC 1-2x.87EE meganuclease set forth as SEQ ID NO: 9.

In another aspect, the invention provides a population of genetically-modified eukaryotic cells comprising a plurality of a genetically-modified eukaryotic cell described herein.

In some embodiments, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified eukaryotic cell as described herein.

In particular embodiments, the genetically-modified eukaryotic cells of the population are genetically-modified human T cells, or cells derived therefrom, or genetically-modified NK cells, or cells derived therefrom.

In certain embodiments, the genetically-modified eukaryotic cells of the population comprise a cell surface chimeric antigen receptor or exogenous T cell receptor. In some of these embodiments, the chimeric antigen receptor or exogenous T cell receptor comprises an extracellular ligand-binding domain having specificity for a tumor-specific antigen.

In specific embodiments, the genetically-modified eukaryotic cells of the population have reduced cell surface expression of an endogenous T cell receptor (e.g., an alpha/beta T cell receptor) when compared to an unmodified control cell.

In another aspect, the invention provides a pharmaceutical composition useful for the treatment of a disease in a subject in need thereof, wherein the pharmaceutical composition comprises a pharmaceutically-acceptable carrier and a therapeutically-effective amount of the genetically-modified eukaryotic cell or population thereof as described herein.

In certain embodiments, the genetically-modified eukaryotic cell is or the population is comprised of a genetically-modified human T cell, or a cell derived therefrom, or a genetically-modified NK cell, or a cell derived therefrom.

In some embodiments, the exogenous sequence of interest present in the genetically-modified T cell or population thereof comprises a coding sequence for a chimeric antigen receptor or an exogenous T cell receptor. In certain particular embodiments, the chimeric antigen receptor or the exogenous T cell receptor comprises an extracellular ligand-binding domain having specificity for a tumor-specific antigen.

In some embodiments, cell surface expression of an endogenous T cell receptor (e.g., an alpha/beta T cell receptor) is reduced on the genetically-modified eukaryotic cell when compared to an unmodified control cell.

In another aspect, the invention provides a lipid nanoparticle, or a lipid nanoparticle formulation, comprising mRNA encoding at least one engineered meganuclease described herein. In some embodiments, the lipid nanoparticles have a composition which increases delivery and uptake by T cells.

In another aspect, the invention provides a method of treating a disease in a subject in need thereof, the method comprising administering to the subject a therapeutically-effective amount of the genetically-modified eukaryotic cell or population thereof as described herein.

In some embodiments, the method comprises administering to the subject a pharmaceutical composition described herein.

In certain embodiments, the method is an immunotherapy for the treatment of a cancer in a subject in need thereof. In some such embodiments, the genetically-modified eukaryotic cell is a genetically-modified human T cell, or a cell derived therefrom, or a genetically-modified human NK cell, or a cell derived therefrom, and the exogenous sequence of interest present in the genetically-modified eukaryotic cell comprises a coding sequence for a chimeric antigen receptor or an exogenous T cell receptor comprising an extracellular ligand-binding domain having specificity for a tumor-specific antigen, and cell surface expression of an endogenous T cell receptor (e.g., an alpha/beta T cell receptor) is reduced on the genetically-modified eukaryotic cell when compared to an unmodified control cell.

In some embodiments of the method, the cancer is selected from the group consisting of a cancer of carcinoma, lymphoma, sarcoma, blastomas, and leukemia.

In certain embodiments of the method, the cancer is selected from the group consisting of a cancer of B-cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma.

In particular embodiments of the method, the cancer of B-cell origin is selected from the group consisting of B-lineage acute lymphoblastic leukemia, B-cell chronic lymphocytic leukemia, B-cell non-Hodgkin's lymphoma, and multiple myeloma.

In particular embodiments of the methods, the subject can be a mammal, such as a human.

In another aspect, the invention provides a genetically-modified cell or a population thereof, as described herein, for use as a medicament. The invention further provides the use of a genetically-modified cell or a population thereof, as described herein, in the manufacture of a medicament for treating a disease in a subject in need thereof. In one such aspect, the medicament is useful in the treatment of a cancer.

In another aspect, the invention provides a genetically-modified cell or population thereof, as described herein, for use in treatment of a disease, and preferably in the treatment of a cancer.

BRIEF DESCRIPTION OF THE FIGURES

FIG. 1. TRC 1-2 recognition sequence in the human T cell receptor alpha constant region gene. The TRC 1-2 recognition sequence, targeted by engineered meganucleases of the invention, comprises two recognition half-sites. Each recognition half-site comprises 9 base pairs, separated by a 4 base pair central sequence. The TRC 1-2 recognition sequence (SEQ ID NO: 5) comprises two recognition half-sites referred to as TRC1 and TRC2.

FIG. 8. Efficiency of engineered meganucleases for recognizing and cleaving the TRC Off1 and Off2 recognition sequences in a CHO cell reporter assay. The first-generation TRC 1-2x.87EE meganuclease, the intermediate TRC 1-2L.1469 meganuclease, and the second-generation TRC 1-2L.1592, TRC 1-2L.1775, and TRC 1-2L.1843 meganucleases were screened in CHO GFFP reporter cells comprising the TRC Off1 (SEQ ID NO: 16) or Off2 (SEQ ID NO: 17) recognition sequences for efficacy in the CHO cell reporter assay at 2, 5, and 7 days after nucleofection in order to determine toxicity. The results shown provide the percentage of GFP-expressing cells observed over the 7 day period of analysis. A) Cleavage of the Off1 recognition sequence. B) Cleavage of the Off2 recognition sequence.

FIG. 11. Table summarizing in vitro analysis of CAR T cells generated using the first-generation TRC 1-2x.87EE meganuclease, the intermediate TRC 1-2L.1469 meganuclease, or the second-generation TRC 1-2L.1592, TRC 1-2L.1775, and TRC 1-2L.1843 meganucleases. Meganucleases were screened for gene-editing efficiency, post-editing expansion, and differentiation potential. CAR T cells were prepared from cells obtained from three different healthy human donors, and experiments were conducted by three different operators.

FIG. 15. CAR T cell expansion following co-culture with antigen-bearing target cells. Expansion was assessed following co-culture of CAR T cells with the Raji CD19+ tumor line at an E:T ratio of 1:2 for 5 days. A) Total number of CAR-positive cells in culture following co-culture with Raji cells. B) Total number of remaining CD19-positive cells in culture following co-culture of CAR T cells with Raji cells.

BRIEF DESCRIPTION OF THE SEQUENCES

Figure 2:
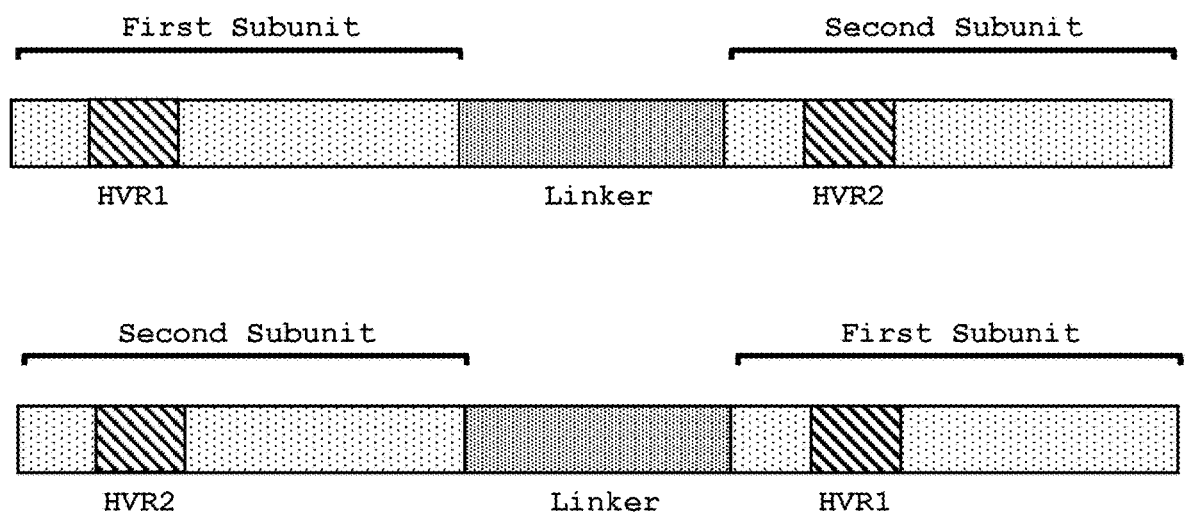
FIG. 2. The engineered meganucleases of the invention comprise two subunits, wherein the first subunit comprising the HVR1 region binds to a first recognition half-site (e.g., TRC1) and the second subunit comprising the HVR2 region binds to a second recognition half-site (e.g., TRC2). In embodiments where the engineered meganuclease is a single-chain meganuclease, the first subunit comprising the HVR1 region can be positioned as either the N-terminal or C-terminal subunit. Likewise, the second subunit comprising the HVR2 region can be positioned as either the N-terminal or C-terminal subunit.

SEQ ID NO: 1 sets forth the amino acid sequence of the wild-type I-CreI meganuclease from Chlamydomonas reinhardtii.

SEQ ID NO: 2 sets forth the amino acid sequence of the LAGLIDADG motif.

SEQ ID NO: 3 sets forth the nucleic acid sequence of the human T cell receptor alpha constant region gene (NCBI Gene ID NO. 28755).

SEQ ID NO: 4 sets forth the amino acid sequence of the polypeptide encoded by the human T cell receptor alpha constant region gene.

SEQ ID NO: 5 sets forth the nucleic acid sequence of the sense strand of the TRC 1-2 recognition sequence.

SEQ ID NO: 6 sets forth the nucleic acid sequence of the antisense strand of the TRC 1-2 recognition sequence.

SEQ ID NO: 7 sets forth the amino acid sequence of the TRC 1-2L.1592 meganuclease.

SEQ ID NO: 8 sets forth the amino acid sequence of the TRC 1-2L.1775 meganuclease.

SEQ ID NO: 9 sets forth the amino acid sequence of the TRC 1-2x.87EE meganuclease.

SEQ ID NO: 10 sets forth the amino acid sequence of the TRC 1-2L.1592 meganuclease TRC1-binding subunit.

SEQ ID NO: 11 sets forth the amino acid sequence of the TRC 1-2L.1775 meganuclease TRC1-binding subunit.

SEQ ID NO: 12 sets forth the amino acid sequence of the TRC 1-2x.87EE meganuclease TRC1-binding subunit.

SEQ ID NO: 13 sets forth the amino acid sequence of the TRC 1-2L.1592 meganuclease TRC2-binding subunit.

SEQ ID NO: 14 sets forth the amino acid sequence of the TRC 1-2L.1775 meganuclease TRC2-binding subunit.

SEQ ID NO: 15 sets forth the amino acid sequence of the TRC 1-2x.87EE meganuclease TRC2-binding subunit.

SEQ ID NO: 16 sets forth the nucleic acid sequence of the Off1 recognition sequence.

SEQ ID NO: 17 sets forth the nucleic acid sequence of the Off2 recognition sequence.

SEQ ID NO: 18 sets forth the amino acid sequence of a polypeptide linker.

DETAILED DESCRIPTION OF THE INVENTION 1.1 References and Definitions

The patent and scientific literature referred to herein establishes knowledge that is available to those of skill in the art. The issued US and non-US patents, allowed applications, published US, non-US, and PCT applications, co-owned and co-pending unpublished US patent applications, published foreign applications, and scientific, technical, and medical references, including GenBank database sequences, public genetic and protein database accession numbers or codes (and the nucleic acid and/or amino acid sequences associated therewith), which are cited herein are hereby incorporated by reference to the same extent as if each was specifically and individually indicated to be incorporated by reference.

The present invention can be embodied in different forms and should not be construed as limited to the embodiments set forth herein. Rather, these embodiments are provided so that this disclosure will be thorough and complete, and will fully convey the scope of the invention to those skilled in the art. For example, features illustrated with respect to one embodiment can be incorporated into other embodiments, and features illustrated with respect to a particular embodiment can be deleted from that embodiment. In addition, numerous variations and additions to the embodiments suggested herein will be apparent to those skilled in the art in light of the instant disclosure, which do not depart from the instant invention.

Unless otherwise defined, all technical and scientific terms used herein have the same meaning as commonly understood as of the priority date by one of ordinary skill in the art to which this invention belongs. The terminology used in the description of the invention herein is for the purpose of describing particular embodiments only and is not intended to be limiting of the invention.

All publications, patent applications, patents, and other references mentioned herein are incorporated by reference herein in their entirety.

As used herein, "a," "an," or "the" can mean one or more than one. For example, "a" cell can mean a single cell or a multiplicity of cells.

As used herein, unless specifically indicated otherwise, the word "or" is used in the inclusive sense of "and/or" and not the exclusive sense of "either/or."

As used herein, the term "endonuclease" refers to enzymes which cleave a phosphodiester bond within a polynucleotide chain.

As used herein, with respect to double-stranded DNA, the terms "cleave" or "cleavage" refer to the endonuclease-mediated hydrolysis of phosphodiester bonds within the backbone of a recognition sequence within a target sequence that results in a double-stranded break within the target sequence, referred to herein as a "cleavage site". Depending upon the endonuclease, cleavage can result in double-stranded fragments with blunt ends or fragments with 5' or 3' base overhangs.

As used herein, the term "meganuclease" refers to an endonuclease that binds double-stranded DNA at a recognition sequence that is greater than 12 base pairs. In some embodiments, the recognition sequence for a meganuclease of the present disclosure is 22 base pairs. A meganuclease can be an endonuclease that is derived from I-CreI, and can refer to an engineered variant of I-CreI that has been modified relative to natural I-CreI with respect to, for example, DNA-binding specificity, DNA cleavage activity, DNA-binding affinity, or dimerization properties. Methods for producing such modified variants of I-CreI are known in the art (e.g. WO 2007/047859, incorporated by reference in its entirety). A meganuclease as used herein binds to double-stranded DNA as a heterodimer. A meganuclease may also be a "single-chain meganuclease" in which a pair of DNA-binding domains is joined into a single polypeptide using a peptide linker. The term "homing endonuclease" is synonymous with the term "meganuclease." Meganucleases of the present disclosure are substantially non-toxic when expressed in the targeted cells as described herein, particularly in human T cells, such that cells can be transfected and maintained at 37oC without observing substantial deleterious effects on overall cell viability or significant reductions in meganuclease cleavage activity when measured using the methods described herein.

As used herein, the term "single-chain meganuclease" refers to a polypeptide comprising a pair of nuclease subunits joined by a linker such that the subunits interact functionally like a heterodimer to cleave a double-stranded recognition site. A single-chain meganuclease has the organization: N-terminal subunit-Linker-C-terminal subunit. The two meganuclease subunits will generally be non-identical in amino acid sequence and will recognize non-identical DNA half-sites within a recognition sequence. Thus, single-chain meganucleases typically cleave pseudo-palindromic or non-palindromic recognition sequences. A single-chain meganuclease may be referred to as a "single-chain heterodimer" or "single-chain heterodimeric meganuclease" although it is not, in fact, dimeric. For clarity, unless otherwise specified, the term "meganuclease" can refer to a dimeric or single-chain meganuclease.

As used herein, the term "linker" refers to an exogenous peptide sequence used to join two meganuclease subunits into a single polypeptide. A linker may have a sequence that is found in natural proteins, or may be an artificial sequence that is not found in any natural protein. A linker may be flexible and lacking in secondary structure or may have a propensity to form a specific three-dimensional structure under physiological conditions. A linker can include, without limitation, any of those encompassed by U.S. Pat. Nos. 8,445,251, 9,340,777, 9,434,931, and 10,041,053, each of which is incorporated by reference in its entirety. In some embodiments, a linker may have at least 80%, at least 85%, at least 90%, at least 91%, at least 92%, at least 93%, at least 94%, at least 95%, at least 96%, at least 97%, at least 98%, at least 99%, or more, sequence identity to SEQ ID NO: 18, which sets forth residues 154-195 of SEQ ID NO: 7 or 8. In some embodiments, a linker may have an amino acid sequence comprising SEQ ID NO:18, which sets forth residues 154-195 of SEQ ID NO: 7 or 8.

As used herein, with respect to a protein, the term "recombinant" or "engineered" means having an altered amino acid sequence as a result of the application of genetic engineering techniques to nucleic acids which encode the protein, and cells or organisms which express the protein. With respect to a nucleic acid, the term "recombinant" or "engineered" means having an altered nucleic acid sequence as a result of the application of genetic engineering techniques. Genetic engineering techniques include, but are not limited to, PCR and DNA cloning technologies; transfection, transformation and other gene transfer technologies; homologous recombination; site-directed mutagenesis; and gene fusion. In accordance with this definition, a protein having an amino acid sequence identical to a naturally-occurring protein, but produced by cloning and expression in a heterologous host, is not considered recombinant.

As used herein, the term "wild-type" refers to the most common naturally occurring allele (i.e., polynucleotide sequence) in the allele population of the same type of gene, wherein a polypeptide encoded by the wild-type allele has its original functions. The term "wild-type" also refers to a polypeptide encoded by a wild-type allele. Wild-type alleles (i.e., polynucleotides) and polypeptides are distinguishable from mutant or variant alleles and polypeptides, which comprise one or more mutations and/or substitutions relative to the wild-type sequence(s). Whereas a wild-type allele or polypeptide can confer a normal phenotype in an organism, a mutant or variant allele or polypeptide can, in some instances, confer an altered phenotype. Wild-type nucleases are distinguishable from recombinant or non-naturally-occurring nucleases. The term "wild-type" can also refer to a cell, an organism, and/or a subject which possesses a wild-type allele of a particular gene, or a cell, an organism, and/or a subject used for comparative purposes.

As used herein, the term "genetically-modified" refers to a cell or organism in which, or in an ancestor of which, a genomic DNA sequence has been deliberately modified by recombinant technology. As used herein, the term "genetically-modified" encompasses the term "transgenic."

As used herein with respect to recombinant proteins, the term "modification" means any insertion, deletion, or substitution of an amino acid residue in the recombinant sequence relative to a reference sequence (e.g., a wild-type or a native sequence).

As used herein, the terms "recognition sequence" or "recognition site" refers to a DNA sequence that is bound and cleaved by an endonuclease. In the case of a meganuclease, a recognition sequence comprises a pair of inverted, 9 basepair "half sites" which are separated by four basepairs. In the case of a single-chain meganuclease, the N-terminal domain of the protein contacts a first half-site and the C-terminal domain of the protein contacts a second half-site. Cleavage by a meganuclease produces four basepair 3' "overhangs". "Overhangs," or "sticky ends" are short, single-stranded DNA segments that can be produced by endonuclease cleavage of a double-stranded DNA sequence. In the case of meganucleases and single-chain meganucleases derived from I-CreI, the overhang comprises bases 10-13 of the 22 basepair recognition sequence.

As used herein, the term "target site" or "target sequence" refers to a region of the chromosomal DNA of a cell comprising a recognition sequence for a nuclease.

As used herein, the term "DNA-binding affinity" or "binding affinity" means the tendency of a meganuclease to non-covalently associate with a reference DNA molecule (e.g., a recognition sequence or an arbitrary sequence). Binding affinity is measured by a dissociation constant, Kd. As used herein, a nuclease has "altered" binding affinity if the Kd of the nuclease for a reference recognition sequence is increased or decreased by a statistically significant percent change, or biologically significant amount (e.g., at least 2×, or 2× to 10×), relative to a reference nuclease.

As used herein, the term "specificity" means the ability of a nuclease to recognize and cleave double-stranded DNA molecules only at a particular sequence of base pairs referred to as the recognition sequence, or only at a particular set of recognition sequences. The set of recognition sequences will share certain conserved positions or sequence motifs, but may be degenerate at one or more positions. A highly-specific nuclease is capable of cleaving only one or a very few recognition sequences. Specificity can be determined by any method known in the art.

As used herein, a nuclease has "altered" specificity if it binds to and cleaves a recognition sequence which is not bound to and cleaved by a reference nuclease (e.g., a wild-type) under physiological conditions, or if the rate of cleavage of a recognition sequence is increased or decreased by a biologically significant amount (e.g., at least 2×, or 2×-10×) relative to a reference nuclease.

In some embodiments, the presently disclosed engineered meganucleases have improved (i.e., increased) specificity for the target recognition sequence that comprises SEQ ID NO: 5 (i.e., TRC 1-2) as compared to the TRC 1-2x.87EE meganuclease (the amino acid sequence of which is set forth as SEQ ID NO: 9). Thus, in certain embodiments, the presently disclosed engineered meganucleases exhibit reduced off-target cleavage as compared to the TRC 1-2x.87EE meganuclease. Off-target cleavage by a meganuclease can be measured using any method known in the art, including for example, oligo capture analysis as described herein, a T7 endonuclease I (T7E) assay, digital PCR, targeted sequencing of particular off-target sites, exome sequencing, whole genome sequencing, direct in situ breaks labeling enrichment on streptavidin and next-generation sequencing (BLESS), genome-wide, unbiased identification of DSBs enabled by sequencing (GUIDE-seq), and linear amplification-mediated high-throughput genome-wide translocation sequencing (LAM-HTGTS) (see, e.g., Zischewski et al. (2017) Biotechnology Advances 35(1):95-104, which is incorporated by reference in its entirety).

As used herein, the term "homologous recombination" or "HR" refers to the natural, cellular process in which a double-stranded DNA-break is repaired using a homologous DNA sequence as the repair template (see, e.g. Cahill et al. (2006), Front. Biosci. 11:1958-1976). The homologous DNA sequence may be an endogenous chromosomal sequence or an exogenous nucleic acid that was delivered to the cell.

As used herein, the term "non-homologous end-joining" or "NHEJ" refers to the natural, cellular process in which a double-stranded DNA-break is repaired by the direct joining of two non-homologous DNA segments (see, e.g. Cahill et al. (2006), Front. Biosci. 11:1958-1976). DNA repair by non-homologous end-joining is error-prone and frequently results in the untemplated addition or deletion of DNA sequences at the site of repair. In some instances, cleavage at a target recognition sequence results in NHEJ at a target recognition site. Nuclease-induced cleavage of a target site in the coding sequence of a gene followed by DNA repair by NHEJ can introduce mutations into the coding sequence, such as frameshift mutations, that disrupt gene function. Thus, engineered nucleases can be used to effectively knock-out a gene in a population of cells. As used herein, "disrupting a target sequence" refers to the introduction of a mutation (e.g., frameshift mutation) that interferes with the gene function and prevents expression and/or function of the polypeptide/expression product encoded thereby.

As used herein, a "homology arm" or "sequences homologous to sequences flanking a meganuclease cleavage site" refer to sequences flanking the 5' and 3' ends of a nucleic acid molecule which promote insertion of the nucleic acid molecule into a cleavage site generated by a meganuclease. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

As used herein, a "chimeric antigen receptor" or "CAR" refers to an engineered receptor that confers or grafts specificity for an antigen onto an immune effector cell (e.g., a human T cell). A chimeric antigen receptor typically comprises at least an extracellular ligand-binding domain or moiety and an intracellular domain that comprises one or more signaling domains and/or co-stimulatory domains.

In some embodiments, the extracellular ligand-binding domain or moiety is in the form of a single-chain variable fragment (scFv) derived from a monoclonal antibody, which provides specificity for a particular epitope or antigen (e.g., an epitope or antigen preferentially present on the surface of a cell, such as a cancer cell or other disease-causing cell or particle). In some embodiments, the scFv is attached via a linker sequence. In various embodiments, the extracellular ligand-binding domain is specific for any antigen or epitope of interest. In some embodiments, the scFv is murine, humanized, or fully human.

The extracellular domain of a chimeric antigen receptor can also comprise an autoantigen (see, Payne et al. (2016), Science 353 (6295): 179-184), that can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs), and their use is encompassed by the invention.

The extracellular domain of a chimeric antigen receptor can also comprise a naturally-occurring ligand for an antigen of interest, or a fragment of a naturally-occurring ligand which retains the ability to bind the antigen of interest.

The intracellular stimulatory domain can include one or more cytoplasmic signaling domains that transmit an activation signal to the immune effector cell following antigen binding. Such cytoplasmic signaling domains can include, without limitation, CD3☐. The intracellular stimulatory domain can also include one or more intracellular co-stimulatory domains that transmit a proliferative and/or cell-survival signal after ligand binding. Such intracellular co-stimulatory domains can be any of those known in the art and can include, without limitation, CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3 and a ligand that specifically binds with CD83, N1, N6, or any combination thereof.

A chimeric antigen receptor can further include additional structural elements, including a transmembrane domain that is attached to the extracellular ligand-binding domain via a hinge or spacer sequence. The transmembrane domain can be derived from any membrane-bound or transmembrane protein. For example, the transmembrane polypeptide can be a subunit of the T-cell receptor (i.e., an α, β, γ or ζ, polypeptide constituting CD3 complex), IL2 receptor p55 (a chain), p75 (β chain) or γ chain, subunit chain of Fc receptors (e.g., Fcγ receptor III) or CD proteins such as the CD8 alpha chain. Alternatively the transmembrane domain can be synthetic and can comprise predominantly hydrophobic residues such as leucine and valine.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In particular examples, a hinge domain can comprise a part of a human CD8 alpha chain, FcγRIIIa receptor or IgG1.

As used herein, an "exogenous T cell receptor" or "exogenous TCR" refers to a TCR whose sequence is introduced into the genome of an immune effector cell (e.g., a human T cell) that may or may not endogenously express the TCR. Expression of an exogenous TCR on an immune effector cell can confer specificity for a specific epitope or antigen (e.g., an epitope or antigen preferentially present on the surface of a cancer cell or other disease-causing cell or particle). Such exogenous T cell receptors can comprise alpha and beta chains or, alternatively, may comprise gamma and delta chains. Exogenous TCRs useful in the invention may have specificity to any antigen or epitope of interest.

As used herein, the term "reduced expression" refers to any reduction in the expression of the endogenous T cell receptor (e.g., an alpha/beta T cell receptor) at the cell surface of a genetically-modified T cell when compared to a control cell. The term reduced can also refer to a reduction in the percentage of cells in a population of cells that express an endogenous polypeptide (i.e., an endogenous T cell receptor) at the cell surface when compared to a population of control cells. Such a reduction may be up to 5%, 10%, 20%, 30%, 40%, 50%, 60%, 70%, 80%, 90%, 95%, 96%, 97%, 98%, 99%, or up to 100%. Accordingly, the term "reduced" encompasses both a partial knockdown and a complete knockdown of the endogenous T cell receptor. A knockout (i.e., a complete knockdown) of cell-surface expression of an endogenous T cell receptor can result from the genetic inactivation of the T cell receptor alpha constant region gene using the engineered meganucleases described herein. The alpha constant domain encoded by the T cell receptor alpha constant region gene is necessary for assembly of the endogenous TCR complex on the cell surface. Thus, knocking out the T cell receptor alpha constant region gene using engineered meganucleases described herein results in a knockout of cell-surface T cell receptor expression.

As used herein with respect to both amino acid sequences and nucleic acid sequences, the terms "percent identity," "sequence identity," "percentage similarity," "sequence similarity" and the like refer to a measure of the degree of similarity of two sequences based upon an alignment of the sequences which maximizes similarity between aligned amino acid residues or nucleotides, and which is a function of the number of identical or similar residues or nucleotides, the number of total residues or nucleotides, and the presence and length of gaps in the sequence alignment. A variety of algorithms and computer programs are available for determining sequence similarity using standard parameters. As used herein, sequence similarity is measured using the BLASTp program for amino acid sequences and the BLASTn program for nucleic acid sequences, both of which are available through the National Center for Biotechnology Information (www.ncbi.nlm.nih.gov/), and are described in, for example, Altschul et al. (1990), J. Mol. Biol. 215:403-410; Gish and States (1993), Nature Genet. 3:266-272; Madden et al. (1996), Meth. Enzymol.266:131-141; Altschul et al. (1997), Nucleic Acids Res. 25:33 89-3402); Zhang et al. (2000), J. Comput. Biol. 7(1-2):203-14. As used herein, percent similarity of two amino acid sequences is the score based upon the following parameters for the BLASTp algorithm: word size=3; gap opening penalty=−11; gap extension penalty=−1; and scoring matrix=BLOSUM62. As used herein, percent similarity of two nucleic acid sequences is the score based upon the following parameters for the BLASTn algorithm: word size=11; gap opening penalty=−5; gap extension penalty=−2; match reward=1; and mismatch penalty=−3.

As used herein with respect to modifications of two proteins or amino acid sequences, the term "corresponding to" is used to indicate that a specified modification in the first protein is a substitution of the same amino acid residue as in the modification in the second protein, and that the amino acid position of the modification in the first protein corresponds to or aligns with the amino acid position of the modification in the second protein when the two proteins are subjected to standard sequence alignments (e.g., using the BLASTp program). Thus, the modification of residue "X" to amino acid "A" in the first protein will correspond to the modification of residue "Y" to amino acid "A" in the second protein if residues X and Y correspond to each other in a sequence alignment, and despite the fact that X and Y may be different numbers.

As used herein, the term "recognition half-site," "recognition sequence half-site," or simply "half-site" means a nucleic acid sequence in a double-stranded DNA molecule which is recognized by a monomer of a homodimeric or heterodimeric meganuclease, or by one subunit of a single-chain meganuclease.

As used herein, the term "hypervariable region" refers to a localized sequence within a meganuclease monomer or subunit that comprises amino acids with relatively high variability. A hypervariable region can comprise about 50-60 contiguous residues, about 53-57 contiguous residues, or preferably about 56 residues. In some embodiments, the residues of a hypervariable region may correspond to positions 24-79 or positions 215-270 of SEQ ID NO: 7 or 8. A hypervariable region can comprise one or more residues that contact DNA bases in a recognition sequence and can be modified to alter base preference of the monomer or subunit. A hypervariable region can also comprise one or more residues that bind to the DNA backbone when the meganuclease associates with a double-stranded DNA recognition sequence. Such residues can be modified to alter the binding affinity of the meganuclease for the DNA backbone and the target recognition sequence. In different embodiments of the invention, a hypervariable region may comprise between 1-20 residues that exhibit variability and can be modified to influence base preference and/or DNA-binding affinity. In particular embodiments, a hypervariable region comprises between about 15-20 residues that exhibit variability and can be modified to influence base preference and/or DNA-binding affinity.

In some embodiments, variable residues within a hypervariable region correspond to one or more of positions 24, 26, 28, 30, 32, 33, 38, 40, 42, 44, 46, 68, 70, 75, and 77 of SEQ ID NO: 7 or 8. In some embodiments, variable residues within a hypervariable region further correspond to one or more of positions 48, 50, 71, 72, and 73 of SEQ ID NO: 7. In some embodiments, variable residues within a hypervariable region further correspond to one or more of positions 48 and 50 of SEQ ID NO: 8. In some embodiments, variable residues within a hypervariable region correspond to one or more of positions 24, 26, 28, 30, 32, 33, 38, 40, 42, 44, 46, 48, 50, 68, 70, 71, 72, 73, 75, and 77 of SEQ ID NO: 7 or 8.

In other embodiments, variable residues within a hypervariable region correspond to one or more of positions 215, 217, 219, 221, 223, 224, 229, 231, 233, 235, 237, 259, 261, 266, and 268 of SEQ ID NO: 7 or 8.

As used herein, the terms "T cell receptor alpha gene" or "TCR alpha gene" are interchangeable and refer to the locus in a T cell which encodes the T cell receptor alpha subunit. The T cell receptor alpha can refer to NCBI gene ID number 6955, before or after rearrangement. Following rearrangement, the T cell receptor alpha gene comprises an endogenous promoter, rearranged V and J segments, the endogenous splice donor site, an intron, the endogenous splice acceptor site, and the T cell receptor alpha constant region locus, which comprises the subunit coding exons.

As used herein, the term "T cell receptor alpha constant region" or "TCR alpha constant region" refers to the coding sequence of the T cell receptor alpha gene. The TCR alpha constant region includes the wild-type sequence, and functional variants thereof, identified by NCBI Gen ID NO. 28755.

The terms "recombinant DNA construct," "recombinant construct," "expression cassette," "expression construct," "chimeric construct," "construct," and "recombinant DNA fragment" are used interchangeably herein and are single or double-stranded polynucleotides. A recombinant construct comprises an artificial combination of nucleic acid fragments, including, without limitation, regulatory and coding sequences that are not found together in nature. For example, a recombinant DNA construct may comprise regulatory sequences and coding sequences that are derived from different sources, or regulatory sequences and coding sequences derived from the same source and arranged in a manner different than that found in nature. Such a construct may be used by itself or may be used in conjunction with a vector.

As used herein, a "vector" or "recombinant DNA vector" may be a construct that includes a replication system and sequences that are capable of transcription and translation of a polypeptide-encoding sequence in a given host cell. If a vector is used then the choice of vector is dependent upon the method that will be used to transform host cells as is well known to those skilled in the art. Vectors can include, without limitation, plasmid vectors and recombinant viral vectors (e.g., AAV vectors), or any other vector known in that art suitable for delivering a gene encoding a meganuclease of the invention to a target cell. The skilled artisan is well aware of the genetic elements that must be present on the vector in order to successfully transform, select and propagate host cells comprising any of the isolated nucleotides or nucleic acid sequences of the invention.

As used herein, a "vector" can also refer to a viral vector. Viral vectors can include, without limitation, retroviral vectors, lentiviral vectors, adenoviral vectors, and adeno-associated viral vectors (AAV).

As used herein, a "polycistronic" mRNA refers to a single messenger RNA that comprises two or more coding sequences (i.e., cistrons) and encodes more than one protein. A polycistronic mRNA can comprise any element known in the art to allow for the translation of two or more genes from the same mRNA molecule including, but not limited to, an IRES element, a T2A element, a P2A element, an E2A element, and an F2A element.

As used herein, a "human T cell" or "T cell" refers to a T cell isolated from a donor, particularly a human donor. T cells, and cells derived therefrom, include isolated T cells that have not been passaged in culture, T cells that have been passaged and maintained under cell culture conditions without immortalization, and T cells that have been immortalized and can be maintained under cell culture conditions indefinitely.

As used herein, a "control" or "control cell" refers to a cell that provides a reference point for measuring changes in genotype or phenotype of a genetically-modified cell. A control cell may comprise, for example: (a) a wild-type cell, i.e., of the same genotype as the starting material for the genetic alteration which resulted in the genetically-modified cell; (b) a cell of the same genotype as the genetically-modified cell but which has been transformed with a null construct (i.e., with a construct which has no known effect on the trait of interest); or, (c) a cell genetically identical to the genetically-modified cell but which is not exposed to conditions or stimuli or further genetic modifications that would induce expression of altered genotype or phenotype.

As used herein, the terms "treatment" or "treating a subject" refers to the administration of a genetically-modified T cell or population of genetically-modified T cells of the invention to a subject having a disease. For example, the subject can have a disease such as cancer, and treatment can represent immunotherapy for the treatment of the disease.

Desirable effects of treatment include, but are not limited to, preventing occurrence or recurrence of disease, alleviation of symptoms, diminishment of any direct or indirect pathological consequences of the disease, decreasing the rate of disease progression, amelioration or palliation of the disease state, and remission or improved prognosis. In some aspects, a genetically-modified eukaryotic cell or population of genetically-modified eukaryotic cells described herein is administered during treatment in the form of a pharmaceutical composition of the invention.

The term "effective amount" or "therapeutically effective amount" refers to an amount sufficient to effect beneficial or desirable biological and/or clinical results. The therapeutically effective amount will vary depending on the formulation or composition used, the disease and its severity and the age, weight, physical condition and responsiveness of the subject to be treated. In specific embodiments, an effective amount of a genetically-modified T cell or population of genetically-modified T cells of the invention, or pharmaceutical compositions disclosed herein, reduces at least one symptom of a disease in a subject. In those embodiments wherein the disease is a cancer, an effective amount of the engineered meganuclease or pharmaceutical compositions disclosed herein reduces the level of proliferation or metastasis of cancer, causes a partial or full response or remission of cancer, or reduces at least one symptom of cancer in a subject.

As used herein, the term "cancer" should be understood to encompass any neoplastic disease (whether invasive or metastatic) which is characterized by abnormal and uncontrolled cell division causing malignant growth or tumor.

As used herein, the term "carcinoma" refers to a malignant growth made up of epithelial cells.

As used herein, the term "leukemia" refers to malignancies of the hematopoietic organs/systems and is generally characterized by an abnormal proliferation and development of leukocytes and their precursors in the blood and bone marrow.

As used herein, the term "sarcoma" refers to a tumor which is made up of a substance like the embryonic connective tissue and is generally composed of closely packed cells embedded in a fibrillary, heterogeneous, or homogeneous substance.

As used herein, the term "melanoma" refers to a tumor arising from the melanocytic system of the skin and other organs.

As used herein, the term "lymphoma" refers to a group of blood cell tumors that develop from lymphocytes.

As used herein, the term "blastoma" refers to a type of cancer that is caused by malignancies in precursor cells or blasts (immature or embryonic tissue).

As used herein, the recitation of a numerical range for a variable is intended to convey that the invention may be practiced with the variable equal to any of the values within that range. Thus, for a variable which is inherently discrete, the variable can be equal to any integer value within the numerical range, including the end-points of the range. Similarly, for a variable which is inherently continuous, the variable can be equal to any real value within the numerical range, including the end-points of the range. As an example, and without limitation, a variable which is described as having values between 0 and 2 can take the values 0, 1 or 2 if the variable is inherently discrete, and can take the values 0.0, 0.1, 0.01, 0.001, or any other real values 0 and 2 if the variable is inherently continuous.

2.1 Principle of the Invention

The present invention is based, in part, on the discovery of optimized, second-generation meganucleases that have improved properties compared to parental, first-generation meganucleases, such as improved (i.e., increased) specificity and reduced off-target cutting, reduced persistence time in cells following expression from mRNA, improved cell characteristics when used in vitro with human T cells, and improved cell characteristics when used in a full-scale CAR T cell manufacturing process.

Like the previously described TRC 1-2x.87EE meganuclease, these optimized, second-generation meganucleases recognize the TRC 1-2 recognition sequence (SEQ ID NO: 5) in exon 1 of the TCR alpha constant region gene. Cleavage at this recognition sequence can allow for NHEJ at the cleavage site and disrupted expression of the human T cell receptor alpha chain subunit, leading to reduced expression and/or function of the T cell receptor at the cell surface. Additionally, cleavage at this recognition sequence can further allow for homologous recombination of exogenous nucleic acid sequences directly into the TCR alpha constant region gene. Such exogenous nucleic acid sequences can comprise a sequence of interest, such as a sequence encoding a chimeric antigen receptor, an exogenous TCR receptor, or any other polypeptide of interest. Thus, the presently disclosed compositions and methods allow for both the knockout of the endogenous T cell receptor (e.g., an alpha/beta T cell receptor) and the expression of an exogenous nucleic acid sequence (e.g., a chimeric antigen receptor or exogenous TCR). Such cells can exhibit reduced or no induction of graft-versus-host-disease (GVHD) when administered to an allogeneic subject.

2.2 Optimized Meganucleases that Recognize and Cleave the TRC 1-2 Recognition Sequence within the T Cell Receptor Alpha Constant Region Gene It is known in the art that it is possible to use a site-specific nuclease to make a DNA break in the genome of a living cell, and that such a DNA break can result in permanent modification of the genome via homologous recombination of the cleaved target site with an identical or highly homologous DNA sequence within the genome. Thus, in some embodiments, the invention can be practiced using engineered recombinant meganucleases.

In particular embodiments, the nucleases used to practice the invention are single-chain meganucleases. A single-chain meganuclease comprises an N-terminal subunit and a C-terminal subunit joined by a linker peptide. Each of the two domains recognizes half of the recognition sequence (i.e., a recognition half-site) and the site of DNA cleavage is at the middle of the recognition sequence near the interface of the two subunits. DNA strand breaks are offset by four base pairs such that DNA cleavage by a meganuclease generates a pair of four base pair, 3' single-strand overhangs.

The recombinant meganucleases of the invention have been engineered to recognize and cleave the TRC 1-2 recognition sequence (SEQ ID NO: 5) within exon 1 of the TCR alpha constant region gene (SEQ ID NO: 3). Engineered meganucleases of the invention comprise a first subunit, comprising a first hypervariable (HVR1) region, and a second subunit, comprising a second hypervariable (HVR2) region. Further, the first subunit binds to a first recognition half-site in the recognition sequence (i.e., the TRC1 half-site), and the second subunit binds to a second recognition half-site in the recognition sequence (i.e., the TRC2 half-site). In embodiments where the recombinant meganuclease is a single-chain meganuclease, the first and second subunits can be oriented such that the first subunit, which comprises the HVR1 region and binds the first half-site, is positioned as the N-terminal subunit, and the second subunit, which comprises the HVR2 region and binds the second half-site, is positioned as the C-terminal subunit. In alternative embodiments, the first and second subunits can be oriented such that the first subunit, which comprises the HVR1 region and binds the first half-site, is positioned as the C-terminal subunit, and the second subunit, which comprises the HVR2 region and binds the second half-site, is positioned as the N-terminal subunit. Exemplary engineered meganucleases that recognize and cleave the TRC 1-2 recognition sequence are provided in Table 1.

TABLE 1

Exemplary engineered meganucleases which recognize and
cleave the TCR 1-2 recognition sequence (SEQ ID NO: 5).

| Meganuclease | AA SEQ ID | TRC1 Subunit Residues | TRC1 Subunit SEQ ID | HVR1 Residues | *HVR1 % | TRC2 Subunit Residues | TRC2 Subunit SEQ ID | HVR2 Residues | *HVR2 % |
|---|---|---|---|---|---|---|---|---|---|
| TRC 1-2L.1592 | 7 | 198-344 | 10 | 215-270 | 96.4 | 7-153 | 13 | 24-79 | 80.3 |
| TRC 1-2L.1775 | 8 | 198-344 | 11 | 215-270 | 100 | 7-153 | 14 | 24-79 | 85.7 |
| TRC 1-2x.87EE | 9 | 198-344 | 12 | 215-270 | 100 | 7-153 | 15 | 24-79 | 100 |

*"HVR1%" and "HVR2%" represent the amino acid sequence identity between the HVR1 and HVR2 regions, respectively, of each meganuclease and the HVR1 and HVR2 regions, respectively, of the TRC 1-2x.87EE meganuclease.

In some embodiments, the presently disclosed engineered meganucleases exhibit at least one optimized characteristic in comparison to the first-generation meganuclease TRC 1-2x.87EE. Such optimized characteristics include improved (i.e., increased) specificity resulting in reduced off-target cutting, reduced persistence time in cells following expression from mRNA, and enhanced (i.e., increased) efficiency of cleavage and modification of the TCR alpha constant region gene. Thus, in particular embodiments, the presently disclosed engineered meganucleases when delivered to a population of eukaryotic cells are able to generate a greater percentage of cells with a cleavage and/or modification in the TCR alpha constant region gene. In some of these embodiments, the population of eukaryotic cells comprises at least 40%, at least 45%, at least 50%, at least 55%, at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, at least 99%, or more of eukaryotic cells comprising a cleavage and/or insertion/deletion ("indel") in the TCR alpha constant region gene. Cleavage and/or modification of the TCR alpha constant region gene by a meganuclease can be measured using any method known in the art, including a T7 endonuclease I assay, digital PCR, mismatch detection assays, mismatch cleavage assay, high-resolution melting analysis (HRMA), heteroduplex mobility assay, sequencing, and fluorescent PCR capillary gel electrophoresis (see, e.g., Zischewski et al. (2017) Biotechnology Advances 35(1):95-104, which is incorporated by reference in its entirety).

In certain embodiments, the presently disclosed engineered meganucleases exhibit a reduced persistence time in cells, particularly when introduced as an mRNA, as compared to the first-generation TRC 1-2x.87EE meganuclease. Persistence of an mRNA or protein within a cell can be measured using any method known in the art, including but not limited to, RT-PCR, Northern blot analysis, nuclease protection assays, in situ hybridization, immunocytochemistry, immunoblotting, and immunoprecipitation.

2.3 Methods for Delivering and Expressing Optimized Meganucleases

The invention provides methods for producing genetically-modified T cells and populations thereof using engineered meganucleases that recognize and cleave recognition sequences found within the human TCR alpha constant region gene (SEQ ID NO: 3). T cells can be obtained from a number of sources, including peripheral blood mononuclear cells, bone marrow, lymph node tissue, cord blood, thymus tissue, tissue from a site of infection, ascites, pleural effusion, spleen tissue, and tumors. In certain embodiments of the present disclosure, any number of T cell lines available in the art may be used. In some embodiments of the present disclosure, T cells are obtained from a unit of blood collected from a subject using any number of techniques known to the skilled artisan. In one embodiment, cells from the circulating blood of an individual are obtained by apheresis.

The modified T cell receptor alpha gene comprises an exogenous sequence of interest inserted into the first exon of the TCR alpha constant region gene (i.e., the targeted exon) via double-stranded cleavage by a presently disclosed engineered meganuclease. Cleavage sites generated by such meganucleases can allow for homologous recombination of the exogenous sequence of interest directly into the targeted exon.

As used herein, the term "exogenous" or "heterologous" in reference to a nucleotide sequence is intended to mean a sequence that is purely synthetic, that originates from a foreign species, or, if from the same species, is substantially modified from its native form in composition and/or genomic locus by deliberate human intervention.

In various embodiments, the exogenous sequence of interest can comprise a coding sequence for a protein of interest. It is envisioned that the coding sequence can be for any protein of interest.

In certain embodiments, the exogenous sequence of interest comprises a nucleic acid sequence encoding a chimeric antigen receptor (CAR). Generally, a CAR of the present disclosure will comprise at least an extracellular domain and an intracellular domain. In some embodiments, the extracellular domain comprises a target-specific binding element otherwise referred to as a ligand-binding domain or moiety. In some embodiments, the intracellular domain, or cytoplasmic domain, comprises at least one co-stimulatory domain and one or more signaling domains such as, for example, CD3ζ.

In some embodiments, a CAR useful in the invention comprises an extracellular, target-specific binding element otherwise referred to as a ligand-binding domain or moiety. The choice of ligand-binding domain depends upon the type and number of ligands that define the surface of a target cell. For example, the ligand-binding domain may be chosen to recognize a ligand that acts as a cell surface marker on target cells associated with a particular disease state. Thus, examples of cell surface markers that may act as ligands for the ligand-binding domain in a CAR can include those associated with viruses, bacterial and parasitic infections, autoimmune disease, and cancer cells. In some embodiments, a CAR is engineered to target a tumor-specific antigen of interest by way of engineering a desired ligand-binding moiety that specifically binds to an antigen on a tumor cell. In the context of the present disclosure, "tumor antigen" or "tumor-specific antigen" refer to antigens that are common to specific hyperproliferative disorders such as cancer.

In some embodiments, the extracellular ligand-binding domain of the CAR is specific for any antigen or epitope of interest, particularly any tumor antigen or epitope of interest. As non-limiting examples, in some embodiments the antigen of the target is a tumor-associated surface antigen, such as ErbB2 (HER2/neu), carcinoembryonic antigen (CEA), epithelial cell adhesion molecule (EpCAM), epidermal growth factor receptor (EGFR), EGFR variant III (EGFRvIII), CD19, CD20, CD22, CD30, CD40, CLL-1, disialoganglioside GD2, ductal-epithelial mucine, gp36, TAG-72, glycosphingolipids, glioma-associated antigen, B-human chorionic gonadotropin, alphafetoprotein (AFP), lectin-reactive AFP, thyroglobulin, RAGE-1, MN-CA IX, human telomerase reverse transcriptase, RU1, RU2 (AS), intestinal carboxyl esterase, mut hsp70-2, M-CSF, prostase, prostase specific antigen (PSA), PAP, NY-ESO-1, LAGA-1a, p53, prostein, PSMA, surviving and telomerase, prostate-carcinoma tumor antigen-1 (PCTA-1), MAGE, ELF2M, neutrophil elastase, ephrin B2, insulin growth factor (IGF1)-1, IGF-II, IGFI receptor, mesothelin, a major histocompatibility complex (MHC) molecule presenting a tumor-specific peptide epitope, 5T4, ROR1, Nkp30, NKG2D, tumor stromal antigens, the extra domain A (EDA) and extra domain B (EDB) of fibronectin and the Al domain of tenascin-C (TnC Al) and fibroblast associated protein (fap); a lineage-specific or tissue specific antigen such as CD3, CD4, CD8, CD24, CD25, CD33, CD34, CD38, CD123, CD133, CD138, CTLA-4, B7-1 (CD80), B7-2 (CD86), endoglin, a major histocompatibility complex (MHC) molecule, BCMA (CD269, TNFRSF 17), CS1, or a virus-specific surface antigen such as an HIV-specific antigen (such as HIV gp120); an EBV-specific antigen, a CMV-specific antigen, a HPV-specific antigen such as the E6 or E7 oncoproteins, a Lasse Virus-specific antigen, an Influenza Virus-specific antigen, as well as any derivate or variant of these surface markers. In a particular embodiment of the present disclosure, the ligand-binding domain is specific for CD19.

In some embodiments, the extracellular domain of a chimeric antigen receptor further comprises an autoantigen (see, Payne et al. (2016) Science, Vol. 353 (6295): 179-184), which can be recognized by autoantigen-specific B cell receptors on B lymphocytes, thus directing T cells to specifically target and kill autoreactive B lymphocytes in antibody-mediated autoimmune diseases. Such CARs can be referred to as chimeric autoantibody receptors (CAARs).

In some embodiments, the extracellular domain of a chimeric antigen receptor can comprise a naturally-occurring ligand for an antigen of interest, or a fragment of a naturally-occurring ligand which retains the ability to bind the antigen of interest.

In some embodiments, a CAR comprises a transmembrane domain which links the extracellular ligand-binding domain or autoantigen with the intracellular signaling and co-stimulatory domains via a hinge or spacer sequence. The transmembrane domain can be derived from any membrane-bound or transmembrane protein. For example, the transmembrane polypeptide can be a subunit of the T-cell receptor (i.e., an α, β, γ or ζ, polypeptide constituting CD3 complex), IL2 receptor p55 (a chain), p75 (β chain) or γ chain, subunit chain of Fc receptors (e.g., Fcγ receptor III) or CD proteins such as the CD8 alpha chain. Alternatively the transmembrane domain can be synthetic and can comprise predominantly hydrophobic residues such as leucine and valine. In particular examples, the transmembrane domain is a CD8α transmembrane polypeptide.

The hinge region refers to any oligo- or polypeptide that functions to link the transmembrane domain to the extracellular ligand-binding domain. For example, a hinge region may comprise up to 300 amino acids, preferably 10 to 100 amino acids and most preferably 25 to 50 amino acids. Hinge regions may be derived from all or part of naturally occurring molecules, such as from all or part of the extracellular region of CD8, CD4 or CD28, or from all or part of an antibody constant region. Alternatively, the hinge region may be a synthetic sequence that corresponds to a naturally occurring hinge sequence, or may be an entirely synthetic hinge sequence. In particular examples, a hinge domain can comprise a part of a human CD8 alpha chain, FcγRllla receptor or IgG1.

Intracellular signaling domains of a CAR are responsible for activation of at least one of the normal effector functions of the cell in which the CAR has been placed and/or activation of proliferative and cell survival pathways. The term "effector function" refers to a specialized function of a cell. Effector function of a T cell, for example, may be cytolytic activity or helper activity including the secretion of cytokines. An intracellular signaling domain, such as CD3ζ, can provide an activation signal to the cell in response to binding of the extracellular domain. As discussed, the activation signal can induce an effector function of the cell such as, for example, cytolytic activity or cytokine secretion.

The intracellular domain of the CAR can include one or more intracellular co-stimulatory domains which transmit a co-stimulatory signal to promote cell proliferation, cell survival, and/or cytokine secretion after binding of the extracellular domain. Such intracellular co-stimulatory domains include those known in the art such as, without limitation, N1, N6, CD27, CD28, CD8, 4-1BB (CD137), OX40, CD30, CD40, PD-1, ICOS, lymphocyte function-associated antigen-1 (LFA-1), CD2, CD7, LIGHT, NKG2C, B7-H3, and a ligand that specifically binds with CD83.

The CAR can be specific for any type of cancer cell. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyosarcoma, leukemia, and Hodgkin's lymphoma. In certain embodiments, cancers of B cell origin include, without limitation, B lineage acute lymphoblastic leukemia, B cell chronic lymphocytic leukemia, B cell non-Hodgkin's lymphoma, and multiple myeloma.

The sequence of interest can further encode an exogenous T cell receptor (TCR). Such exogenous T cell receptors can comprise alpha and beta chains or, alternatively, may comprise gamma and delta chains. Exogenous TCRs useful in the invention may have specificity to any antigen or epitope of interest.

In other embodiments, the sequence of interest can encode the wild-type or modified version of an endogenous gene of interest.

The sequence of interest can comprise an element or peptide known in the art to allow for the translation of two more genes from the same promoter, including but not limited to IRES elements and 2A elements, such as, a T2A element, a P2A element, an E2A element, and an F2A element. In specific embodiments, such elements in the exogenous sequence of interest can be located 5' upstream, or 3' downstream of a nucleic acid sequence encoding a protein of interest (e.g. a CAR).

The exogenous sequence of interest described herein can further comprise additional control sequences. For example, the sequences of interest can include homologous recombination enhancer sequences, Kozak sequences, polyadenylation sequences, transcriptional termination sequences, selectable marker sequences (e.g., antibiotic resistance genes), origins of replication, and the like. Sequences of interest described herein can also include at least one nuclear localization signal. Examples of nuclear localization signals are known in the art (see, e.g., Lange et al., J. Biol. Chem., 2007, 282:5101-5105).

Engineered meganucleases of the invention can be delivered into a cell in the form of protein or, preferably, as a nucleic acid encoding the engineered meganuclease. Such nucleic acid can be DNA (e.g., circular or linearized plasmid DNA or PCR products) or RNA (e.g., mRNA). For embodiments in which the engineered meganuclease coding sequence is delivered in DNA form, it should be operably linked to a promoter to facilitate transcription of the meganuclease gene. Mammalian promoters suitable for the invention include constitutive promoters such as the cytomegalovirus early (CMV) promoter (Thomsen et al. (1984), Proc Natl Acad Sci USA. 81(3):659-63) or the SV40 early promoter (Benoist and Chambon (1981), Nature. 290(5804): 304-10) as well as inducible promoters such as the tetracycline-inducible promoter (Dingermann et al. (1992), Mol Cell Biol. 12(9):4038-45). An engineered meganuclease of the invention can also be operably linked to a synthetic promoter. Synthetic promoters can include, without limitation, the JeT promoter (WO 2002/012514).

In some embodiments, mRNA encoding the engineered meganuclease is delivered to the cell because this reduces the likelihood that the gene encoding the engineered meganuclease will integrate into the genome of the cell. Such mRNA encoding an engineered meganuclease can be produced using methods known in the art such as in vitro transcription. In some embodiments, the mRNA is 5' capped using 7-methyl-guanosine, anti-reverse cap analogs (ARCA) (U.S. Pat. No. 7,074,596), CleanCap® analogs such as Cap 1 analogs (Trilink, San Diego, Calif.), or enzymatically capped using vaccinia capping enzyme or similar. In some embodiments, the mRNA may be polyadenylated. The mRNA may contain various 5' and 3' untranslated sequence elements to enhance expression the encoded engineered meganuclease and/or stability of the mRNA itself. Such elements can include, for example, posttranslational regulatory elements such as a woodchuck hepatitis virus posttranslational regulatory element. The mRNA may contain nucleoside analogs or naturally-occurring nucleosides, such as pseudouridine, 5-methylcytidine, N6-methyladenosine, 5-methyluridine, or 2-thiouridine. Additional nucleoside analogs include, for example, those described in U.S. Pat. No. 8,278,036.

In particular embodiments, an mRNA encoding an engineered meganuclease of the invention can be a polycistronic mRNA encoding two or more meganucleases that are simultaneously expressed in the cell. A polycistronic mRNA can encode two or more meganucleases that target different recognition sequences in the same target gene. Alternatively, a polycistronic mRNA can encode at least one meganuclease described herein and at least one additional nuclease targeting a separate recognition sequence positioned in the same gene, or targeting a second recognition sequence positioned in a second gene such that cleavage sites are produced in both genes. A polycistronic mRNA can comprise any element known in the art to allow for the translation of two or more genes (i.e., cistrons) from the same mRNA molecule including, but not limited to, an IRES element, a T2A element, a P2A element, an E2A element, and an F2A element.

In another particular embodiment, a nucleic acid encoding an engineered meganuclease of the invention can be introduced into the cell using a single-stranded DNA template. The single-stranded DNA can further comprise a 5' and/or a 3' AAV inverted terminal repeat (ITR) upstream and/or downstream of the sequence encoding the engineered meganuclease. In other embodiments, the single-stranded DNA can further comprise a 5' and/or a 3' homology arm upstream and/or downstream of the sequence encoding the engineered meganuclease.

In another particular embodiment, genes encoding a meganuclease of the invention can be introduced into a cell using a linearized DNA template. In some examples, a plasmid DNA encoding a meganuclease can be digested by one or more restriction enzymes such that the circular plasmid DNA is linearized prior to being introduced into a cell.

Purified meganuclease proteins can be delivered into cells to cleave genomic DNA, which allows for homologous recombination or non-homologous end-joining at the cleavage site with a sequence of interest, by a variety of different mechanisms known in the art, including those further detailed herein below.

In some embodiments, meganuclease proteins, or DNA/mRNA encoding the meganuclease, are coupled to a cell penetrating peptide or targeting ligand to facilitate cellular uptake. Examples of cell penetrating peptides known in the art include poly-arginine (Jearawiriyapaisarn, et al. (2008) Mol Ther. 16:1624-9), TAT peptide from the HIV virus (Hudecz et al. (2005), Med. Res. Rev. 25: 679-736), MPG (Simeoni, et al. (2003) Nucleic Acids Res. 31:2717-2724), Pep-1 (Deshayes et al. (2004) Biochemistry 43: 7698-7706), and HSV-1 VP-22 (Deshayes et al. (2005) Cell Mol Life Sci. 62:1839-49). In an alternative embodiment, meganuclease proteins, or DNA/mRNA encoding meganucleases, are coupled covalently or non-covalently to an antibody that recognizes a specific cell-surface receptor expressed on target cells such that the meganuclease protein/DNA/mRNA binds to and is internalized by the target cells. Alternatively, meganuclease protein/DNA/mRNA can be coupled covalently or non-covalently to the natural ligand (or a portion of the natural ligand) for such a cell-surface receptor. (McCall, et al. (2014) Tissue Barriers. 2(4):e944449; Dinda, et al. (2013) Curr Pharm Biotechnol. 14:1264-74; Kang, et al. (2014) Curr Pharm Biotechnol. 15(3):220-30; Qian et al. (2014) Expert Opin Drug Metab Toxicol. 10(11):1491-508).

In some embodiments, meganuclease proteins, or DNA/mRNA encoding meganucleases, are coupled covalently or non-covalently to a nanoparticle or encapsulated within such a nanoparticle using methods known in the art (Sharma, et al. (2014) Biomed Res Int. 2014). A nanoparticle is a nanoscale delivery system whose length scale is <1 □m, preferably <100 nm. Such nanoparticles may be designed using a core composed of metal, lipid, polymer, or biological macromolecule, and multiple copies of the recombinant meganuclease proteins, mRNA, or DNA can be attached to or encapsulated with the nanoparticle core. This increases the copy number of the protein/mRNA/DNA that is delivered to each cell and, so, increases the intracellular expression of each engineered meganuclease to maximize the likelihood that the target recognition sequences will be cut. The surface of such nanoparticles may be further modified with polymers or lipids (e.g., chitosan, cationic polymers, or cationic lipids) to form a core-shell nanoparticle whose surface confers additional functionalities to enhance cellular delivery and uptake of the payload (Jian et al. (2012) Biomaterials. 33(30): 7621-30). Nanoparticles may additionally be advantageously coupled to targeting molecules to direct the nanoparticle to the appropriate cell type and/or increase the likelihood of cellular uptake. Examples of such targeting molecules include antibodies specific for cell surface receptors and the natural ligands (or portions of the natural ligands) for cell surface receptors.

In some embodiments, the meganuclease proteins or DNA/mRNA encoding the meganucleases are encapsulated within liposomes or complexed using cationic lipids (see, e.g., Lipofectamine™, Life Technologies Corp., Carlsbad, Calif.; Zuris et al. (2015) Nat Biotechnol. 33: 73-80; Mishra et al. (2011) J Drug Deliv. 2011:863734). The liposome and lipoplex formulations can protect the payload from degradation, and facilitate cellular uptake and delivery efficiency through fusion with and/or disruption of the cellular membranes of the target cells.

In some embodiments, meganuclease proteins, or DNA/mRNA encoding meganucleases, are encapsulated within polymeric scaffolds (e.g., PLGA) or complexed using cationic polymers (e.g., PEI, PLL) (Tamboli et al. (2011) Ther Deliv. 2(4): 523-536). Polymeric carriers can be designed to provide tunable drug release rates through control of polymer erosion and drug diffusion, and high drug encapsulation efficiencies can offer protection of the therapeutic payload until intracellular delivery to the desired target cell population.

In some embodiments, meganuclease proteins, or DNA/mRNA encoding recombinant meganucleases, are combined with amphiphilic molecules that self-assemble into micelles (Tong et al. (2007) J Gene Med. 9(11): 956-66). Polymeric micelles may include a micellar shell formed with a hydrophilic polymer (e.g., polyethyleneglycol) that can prevent aggregation, mask charge interactions, and reduce nonspecific interactions.

In some embodiments, meganuclease proteins, or DNA/mRNA encoding meganucleases, are formulated into an emulsion or a nanoemulsion (i.e., having an average particle diameter of <1 nm) for administration and/or delivery to the target cell. The term "emulsion" refers to, without limitation, any oil-in-water, water-in-oil, water-in-oil-in-water, or oil-in-water-in-oil dispersions or droplets, including lipid structures that can form as a result of hydrophobic forces that drive apolar residues (e.g., long hydrocarbon chains) away from water and polar head groups toward water, when a water immiscible phase is mixed with an aqueous phase. These other lipid structures include, but are not limited to, unilamellar, paucilamellar, and multilamellar lipid vesicles, micelles, and lamellar phases. Emulsions are composed of an aqueous phase and a lipophilic phase (typically containing an oil and an organic solvent). Emulsions also frequently contain one or more surfactants. Nanoemulsion formulations are well known, e.g., as described in US Patent Application Nos. 2002/0045667 and 2004/0043041, and U.S. Pat. Nos. 6,015,832, 6,506,803, 6,635,676, and 6,559,189, each of which is incorporated herein by reference in its entirety.

In some embodiments, meganuclease proteins, or DNA/mRNA encoding meganucleases, are covalently attached to, or non-covalently associated with, multifunctional polymer conjugates, DNA dendrimers, and polymeric dendrimers (Mastorakos et al. (2015) Nanoscale. 7(9): 3845-56; Cheng et al. (2008) J Pharm Sci. 97(1): 123-43). The dendrimer generation can control the payload capacity and size, and can provide a high drug payload capacity. Moreover, display of multiple surface groups can be leveraged to improve stability, reduce nonspecific interactions, and enhance cell-specific targeting and drug release.

In some embodiments, genes encoding a meganuclease are delivered using a viral vector. Such vectors are known in the art and include retroviral vectors, lentiviral vectors, adenoviral vectors, and adeno-associated virus (AAV) vectors (reviewed in Vannucci, et al. (2013 New Microbiol. 36:1-22). Recombinant AAV vectors useful in the invention can have any serotype that allows for transduction of the virus into the cell and insertion of the nuclease gene into the cell genome. In particular embodiments, recombinant AAV vectors have a serotype of AAV2 or AAV6. AAV vectors can also be self-complementary such that they do not require second-strand DNA synthesis in the host cell (McCarty, et al. (2001) Gene Ther. 8:1248-54).

If the meganuclease genes are delivered in DNA form (e.g. plasmid) and/or via a viral vector (e.g. AAV) they must be operably linked to a promoter. In some embodiments, this can be a viral promoter such as endogenous promoters from the viral vector (e.g. the LTR of a lentiviral vector) or the well-known cytomegalovirus- or SV40 virus-early promoters. In a preferred embodiment, meganuclease genes are operably linked to a promoter that drives gene expression preferentially in the target cell (e.g., a T cell).

The invention further provides for the introduction of an exogenous sequence of interest into the T cell receptor alpha constant region gene at the TRC 1-2 recognition sequence. In some embodiments, the exogenous sequence of interest comprises a 5' homology arm and a 3' homology arm flanking the elements of the insert. Such homology arms have sequence homology to corresponding sequences 5' upstream and 3' downstream of the nuclease recognition sequence where a cleavage site is produced. In general, homology arms can have a length of at least 50 base pairs, preferably at least 100 base pairs, and up to 2000 base pairs or more, and can have at least 90%, preferably at least 95%, or more, sequence homology to their corresponding sequences in the genome.

The exogenous sequence of interest of the invention may be introduced into the cell by any of the means previously discussed. In a particular embodiment, the exogenous sequence of interest is introduced by way of a viral vector, such as a lentivirus, retrovirus, adenovirus, or preferably a recombinant AAV vector. Recombinant AAV vectors useful for introducing an exogenous nucleic acid can have any serotype that allows for transduction of the virus into the cell and insertion of the exogenous nucleic acid sequence into the cell genome. In particular embodiments, the recombinant AAV vectors have a serotype of AAV2 or AAV6. The recombinant AAV vectors can also be self-complementary such that they do not require second-strand DNA synthesis in the host cell.

In another particular embodiment, the exogenous sequence of interest can be introduced into the cell using a single-stranded DNA template. The single-stranded DNA can comprise the exogenous sequence of interest and, in preferred embodiments, can comprise 5' and 3' homology arms to promote insertion of the nucleic acid sequence into the meganuclease cleavage site by homologous recombination. The single-stranded DNA can further comprise a 5' AAV inverted terminal repeat (ITR) sequence 5' upstream of the 5' homology arm, and a 3' AAV ITR sequence 3' downstream of the 3' homology arm.

In another particular embodiment, genes encoding an engineered nuclease of the invention and/or an exogenous sequence of interest of the invention can be introduced into the cell by transfection with a linearized DNA template. In some examples, a plasmid DNA can be digested by one or more restriction enzymes such that the circular plasmid DNA is linearized prior to transfection into the cell.

T cells modified by the present invention may require activation prior to introduction of a meganuclease and/or an exogenous sequence of interest. For example, T cells can be contacted with anti-CD3 and anti-CD28 antibodies that are soluble or conjugated to a support (i.e., beads) for a period of time sufficient to activate the cells.

Genetically-modified cells of the invention can be further modified to express one or more inducible suicide genes, the induction of which provokes cell death and allows for selective destruction of the cells in vitro or in vivo. In some examples, a suicide gene can encode a cytotoxic polypeptide, a polypeptide that has the ability to convert a non-toxic pro-drug into a cytotoxic drug, and/or a polypeptide that activates a cytotoxic gene pathway within the cell. That is, a suicide gene is a nucleic acid that encodes a product that causes cell death by itself or in the presence of other compounds. A representative example of such a suicide gene is one that encodes thymidine kinase of herpes simplex virus. Additional examples are genes that encode thymidine kinase of varicella zoster virus and the bacterial gene cytosine deaminase that can convert 5-fluorocytosine to the highly toxic compound 5-fluorouracil. Suicide genes also include as non-limiting examples genes that encode caspase-9, caspase-8, or cytosine deaminase. In some examples, caspase-9 can be activated using a specific chemical inducer of dimerization (CID). A suicide gene can also encode a polypeptide that is expressed at the surface of the cell that makes the cells sensitive to therapeutic and/or cytotoxic monoclonal antibodies. In further examples, a suicide gene can encode recombinant antigenic polypeptide comprising an antigenic motif recognized by the anti-CD20 mAb Rituximab and an epitope that allows for selection of cells expressing the suicide gene. See, for example, the RQR8 polypeptide described in WO2013153391, which comprises two Rituximab-binding epitopes and a QBEnd10-binding epitope. For such a gene, Rituximab can be administered to a subject to induce cell depletion when needed. In further examples, a suicide gene may include a QBEnd10-binding epitope expressed in combination with a truncated EGFR polypeptide.

Eukaryotic cells modified by the methods and compositions described herein can have reduced expression of an endogenous T cell receptor (i.e., an alpha/beta T cell receptor) and, optionally, can further express a protein of interest (e.g., a CAR). Thus, the invention further provides a population of eukaryotic cells that express the protein of interest and do not express the endogenous T cell receptor (e.g., an alpha/beta T cell receptor). For example, the population can include a plurality of genetically-modified eukaryotic cells of the invention which express a CAR (i.e., are CAR+), or an exogenous T cell receptor (i.e., exoTCR+), and have reduced expression of an endogenous T cell receptor (i.e., are TCR−). In various embodiments of the invention, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified eukaryotic cell as described herein. In a particular example, the population can comprise at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, cells that are both TCR− and CAR+.

In some embodiments, when introduced into a population of cells, the presently disclosed engineered meganucleases result in a greater percentage of the population of cells that are both TCR− and CAR+ than when the first-generation TCR 1-2x.87EE meganuclease is introduced into a population of cells.

Further, cells that have been genetically-modified with the presently disclosed engineered meganucleases exhibit improved characteristics, including reduced off-target cutting and effects thereof, reduced persistence time of the meganuclease in the cell, enhanced (i.e., increased) CAR T expansion, and are less differentiated as compared to cells that have been genetically-modified with the TRC1-2x.87EE meganuclease. In addition, populations of cells in which the presently disclosed meganucleases (or a nucleic acid encoding the same) have been introduced have a greater percentage of modified cells and a larger percentage of less differentiated cells when compared to those populations of cells in which the TRC1-2x.87EE meganuclease (or a nucleic acid encoding the same) has been introduced. In particular embodiments, populations of cells in which the presently disclosed engineered meganucleases have been introduced exhibit a greater percentage of central memory T cells (e.g., those that express CD45RO, CCR7, and CD62L) than those populations of cells in which the first-generation TRC1-2x.87EE meganuclease was introduced.

2.4 Pharmaceutical Compositions

In some embodiments, the invention provides a pharmaceutical composition comprising a genetically-modified eukaryotic cell of the invention, or a population of genetically-modified eukaryotic cells of the invention, and a pharmaceutically-acceptable carrier. Such pharmaceutical compositions can be prepared in accordance with known techniques. See, e.g., Remington, The Science And Practice of Pharmacy (21st ed., Philadelphia, Lippincott, Williams & Wilkins, 2005). In the manufacture of a pharmaceutical formulation according to the invention, cells are typically admixed with a pharmaceutically acceptable carrier and the resulting composition is administered to a subject. The carrier must, of course, be acceptable in the sense of being compatible with any other ingredients in the formulation and must not be deleterious to the subject. In some embodiments, pharmaceutical compositions of the invention can further comprise one or more additional agents useful in the treatment of a disease in the subject. In additional embodiments, pharmaceutical compositions of the invention can further include biological molecules, such as cytokines (e.g., IL-2, IL-7, IL-15, and/or IL-21), which promote in vivo cell proliferation and engraftment of genetically-modified T cells. Pharmaceutical compositions comprising genetically-modified eukaryotic cells of the invention can be administered in the same composition as an additional agent or biological molecule or, alternatively, can be co-administered in separate compositions.

The present disclosure also provides genetically-modified cells, or populations thereof, described herein for use as a medicament. The present disclosure further provides the use of genetically-modified cells or populations thereof described herein in the manufacture of a medicament for treating a disease in a subject in need thereof. In one such aspect, the medicament is useful for cancer immunotherapy in subjects in need thereof.

Given that cells in which the presently disclosed meganucleases are introduced can have reduced off-target cutting, reduced persistence time of the meganuclease in the cell, greater efficiency of disruption of the TCR alpha constant region gene, enhanced (i.e., increased) CAR T expansion, and the cells can be less differentiated as compared to cells that have been genetically-modified with the TRC1-2x.87EE meganuclease, in some embodiments, the presently disclosed pharmaceutical compositions comprising genetically-modified cells also have improved efficacy in treating diseases (e.g., cancer) when administered to a subject in need thereof, when compared to the administration of pharmaceutical compositions comprising cells that have been genetically-modified by the TRC1-2x.87EE meganuclease.

In some embodiments, when introduced into a population of cells, the presently disclosed engineered meganucleases result in a greater percentage of the population of cells that are both TCR− and CAR+ than when the first-generation TCR 1-2x.87EE meganuclease is introduced into a population of cells.

Further, cells that have been genetically-modified with the presently disclosed engineered meganucleases exhibit improved characteristics, including reduced off-target cutting and effects thereof, reduced persistence time of the meganuclease in the cell, enhanced (i.e., increased) CAR T expansion, and are less differentiated as compared to cells that have been genetically-modified with the TRC1-2x.87EE meganuclease. In addition, populations of cells in which the presently disclosed meganucleases (or a nucleic acid encoding the same) have been introduced have a greater percentage of modified cells and a larger percentage of less differentiated cells when compared to those populations of cells in which the TRC1-2x.87EE meganuclease (or a nucleic acid encoding the same) has been introduced. In particular embodiments, populations of cells in which the presently disclosed engineered meganucleases have been introduced exhibit a greater percentage of central memory T cells (e.g., those that express CD45RO, CCR7, and CD62L) than those populations of cells that have been introduced the parent TRC1-2x.87EE meganuclease.

Pharmaceutical compositions of the invention can be useful for treating any disease state that can be targeted by T cell adoptive immunotherapy. In a particular embodiment, the pharmaceutical compositions and medicaments of the invention are useful in the treatment of cancer. Non-limiting examples of cancer which may be treated with the pharmaceutical compositions and medicaments of the present disclosure are carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, multiple myeloma, and B-cell non-Hodgkin's lymphoma.

In some of these embodiments wherein cancer is treated with the presently disclosed genetically-modified cells or populations thereof, the subject administered the genetically-modified cells or populations thereof is further administered an additional therapeutic, such as radiation, surgery, or a chemotherapeutic agent.

The invention further provides a population of genetically-modified cells comprising a plurality of genetically-modified cells described herein, which comprise in their genome an exogenous nucleic acid molecule encoding a sequence of interest, wherein the exogenous nucleic acid molecule is inserted into the T cell receptor alpha constant region gene, and wherein cell-surface expression of the endogenous TCR is reduced. Thus, in various embodiments of the invention, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified cell described herein. In further embodiments of the invention, a population of genetically-modified cells is provided wherein at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, at least 99%, or up to 100%, of cells in the population are a genetically-modified cell described herein which further express a chimeric antigen receptor.

2.5. Methods of Administering Genetically-Modified Cells

Another aspect disclosed herein is the administration of an effective amount of the genetically-modified eukaryotic cells or populations thereof of the present disclosure to a subject in need thereof. In particular embodiments, the pharmaceutical compositions described herein are administered to a subject in need thereof. For example, an effective amount of a population of cells can be administered to a subject having a disease. In particular embodiments, the disease can be cancer, and administration of the genetically-modified eukaryotic cells of the invention represent an immunotherapy. The administered cells are able to reduce the proliferation, reduce the number, or kill target cells in the recipient. Unlike antibody therapies, genetically-modified eukaryotic cells of the present disclosure are able to replicate and expand in vivo, resulting in long-term persistence that can lead to sustained control of a disease.

Examples of possible routes of administration include parenteral, (e.g., intravenous (IV), intramuscular (IM), intradermal, subcutaneous (SC), or infusion) administration. Moreover, the administration may be by continuous infusion or by single or multiple boluses. In specific embodiments, the agent is infused over a period of less than about 12 hours, 6 hours, 4 hours, 3 hours, 2 hours, or 1 hour. In still other embodiments, the infusion occurs slowly at first and then is increased over time.

In some embodiments, a genetically-modified eukaryotic cell or population thereof of the present disclosure targets a tumor antigen for the purposes of treating cancer. Such cancers can include, without limitation, carcinoma, lymphoma, sarcoma, blastomas, leukemia, cancers of B cell origin, breast cancer, gastric cancer, neuroblastoma, osteosarcoma, lung cancer, melanoma, prostate cancer, colon cancer, renal cell carcinoma, ovarian cancer, rhabdomyo sarcoma, leukemia, and Hodgkin's lymphoma. In specific embodiments, cancers and disorders include but are not limited to pre-B ALL (pediatric indication), adult ALL, mantle cell lymphoma, diffuse large B cell lymphoma, salvage post allogenic bone marrow transplantation, and the like. These cancers can be treated using a combination of CARs that target, for example, CD19, CD20, CD22, and/or ROR1. In some non-limiting examples, a genetically-modified eukaryotic cell or population thereof of the present disclosure targets carcinomas, lymphomas, sarcomas, melanomas, blastomas, leukemias, and germ cell tumors, including but not limited to cancers of B-cell origin, neuroblastoma, osteosarcoma, prostate cancer, renal cell carcinoma, rhabdomyosarcoma, liver cancer, gastric cancer, bone cancer, pancreatic cancer, skin cancer, cancer of the head or neck, breast cancer, lung cancer, cutaneous or intraocular malignant melanoma, renal cancer, uterine cancer, ovarian cancer, colorectal cancer, colon cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, environmentally induced cancers including those induced by asbestos, multiple myeloma, Hodgkin lymphoma, non-Hodgkin's lymphomas, acute myeloid lymphoma, chronic myelogenous leukemia, chronic lymphoid leukemia, immunoblastic large cell lymphoma, acute lymphoblastic leukemia, mycosis fungoides, anaplastic large cell lymphoma, and T-cell lymphoma, and any combinations of said cancers. In certain embodiments, cancers of B-cell origin include, without limitation, B-lineage acute lymphoblastic leukemia, B-cell chronic lymphocytic leukemia, B-cell lymphoma, diffuse large B cell lymphoma, pre-B ALL (pediatric indication), mantle cell lymphoma, follicular lymphoma, marginal zone lymphoma, Burkitt's lymphoma, multiple myeloma, and B-cell non-Hodgkin's lymphoma.

When an "effective amount" or "therapeutic amount" is indicated, the precise amount to be administered can be determined by a physician with consideration of individual differences in age, weight, tumor size (if present), extent of infection or metastasis, and condition of the patient (subject). In some embodiments, a pharmaceutical composition comprising the genetically-modified cells or populations thereof described herein is administered at a dosage of $10^4$ to $10^9$ cells/kg body weight, including all integer values within those ranges. In further embodiments, the dosage is $10^5$ to $10^6$ cells/kg body weight, including all integer values within those ranges. In some embodiments, cell compositions are administered multiple times at these dosages. The cells can be administered by using infusion techniques that are commonly known in immunotherapy (see, e.g., Rosenberg et al., New Eng. J. of Med. 319:1676, 1988). The optimal dosage and treatment regime for a particular patient can readily be determined by one skilled in the art of medicine by monitoring the patient for signs of disease and adjusting the treatment accordingly.

In some embodiments, administration of genetically-modified eukaryotic cells or populations thereof of the present disclosure reduce at least one symptom of a target disease or condition. For example, administration of genetically-modified T cells or populations thereof of the present disclosure can reduce at least one symptom of a cancer. Symptoms of cancers are well known in the art and can be determined by known techniques.

2.6 Methods for Producing Recombinant Viral Vectors

In some embodiments, the invention provides viral vectors (e.g., recombinant AAV vectors) for use in the methods of the invention. Recombinant AAV vectors are typically produced in mammalian cell lines such as HEK-293. Because the viral cap and rep genes are removed from the vector to prevent its self-replication to make room for the therapeutic gene(s) to be delivered (e.g. the meganuclease gene), it is necessary to provide these in trans in the packaging cell line. In addition, it is necessary to provide the "helper" (e.g. adenoviral) components necessary to support replication (Cots et al. (2013), Curr. Gene Ther. 13(5): 370-81). Frequently, recombinant AAV vectors are produced using a triple-transfection in which a cell line is transfected with a first plasmid encoding the "helper" components, a second plasmid comprising the cap and rep genes, and a third plasmid comprising the viral ITRs containing the intervening DNA sequence to be packaged into the virus. Viral particles comprising a genome (ITRs and intervening gene(s) of interest) encased in a capsid are then isolated from cells by freeze-thaw cycles, sonication, detergent, or other means known in the art. Particles are then purified using cesium-chloride density gradient centrifugation or affinity chromatography and subsequently delivered to the gene(s) of interest to cells, tissues, or an organism such as a human patient.

Because recombinant AAV particles are typically produced (manufactured) in cells, precautions must be taken in practicing the current invention to ensure that the engineered meganuclease is not expressed in the packaging cells. Because the viral genomes of the invention may comprise a recognition sequence for the meganuclease, any meganuclease expressed in the packaging cell line may be capable of cleaving the viral genome before it can be packaged into viral particles. This will result in reduced packaging efficiency and/or the packaging of fragmented genomes. Several approaches can be used to prevent meganuclease expression in the packaging cells, including:

The meganuclease can be placed under the control of a tissue-specific promoter that is not active in the packaging cells. For example, if a viral vector is developed for delivery of (a) meganuclease gene(s) to muscle tissue, a muscle-specific promoter can be used. Examples of muscle-specific promoters include C5-12 (Liu, et al. (2004) Hum Gene Ther. 15:783-92), the muscle-specific creatine kinase (MCK) promoter (Yuasa, et al. (2002) Gene Ther. 9:1576-88), or the smooth muscle 22 (SM22) promoter (Haase, et al. (2013) BMC Biotechnol. 13:49-54). Examples of CNS (neuron)-specific promoters include the NSE, Synapsin, and MeCP2 promoters (Lentz, et al. (2012) Neurobiol Dis. 48:179-88). Examples of liver-specific promoters include albumin promoters (such as Palb), human al-antitrypsin (such as PalAT), and hemopexin (such as Phpx) (Kramer et al., (2003) Mol. Therapy 7:375-85), hybrid liver-specific promoter (hepatic locus control region from ApoE gene (ApoE-HCR) and a liver-specific alphal-antitrypsin promoter), human thyroxine binding globulin (TBG) promoter, and apolipoprotein A-II promoter. Examples of eye-specific promoters include opsin, and corneal epithelium-specific K12 promoters (Martin et al. (2002) Methods (28): 267-75) (Tong et al., (2007) J Gene Med, 9:956-66). These promoters, or other tissue-specific promoters known in the art, are not highly-active in HEK-293 cells and, thus, will not be expected to yield significant levels of meganuclease gene expression in packaging cells when incorporated into viral vectors of the present invention. Similarly, the viral vectors of the present invention contemplate the use of other cell lines with the use of incompatible tissue specific promoters (i.e., the well-known HeLa cell line (human epithelial cell) and using the liver-specific hemopexin promoter). Other examples of tissue specific promoters include: synovial sarcomas PDZD4 (cerebellum), C6 (liver), ASBS (muscle), PPP1R12B (heart), SLC5Al2 (kidney), cholesterol regulation APOM (liver), ADPRHL1 (heart), and monogenic malformation syndromes TP73L (muscle). (Jacox et al., (2010), PLoS One v.5(8):e12274).

Alternatively, the vector can be packaged in cells from a different species in which the meganuclease is not likely to be expressed. For example, viral particles can be produced in microbial, insect, or plant cells using mammalian promoters, such as the well-known cytomegalovirus- or SV40 virus-early promoters, which are not active in the non-mammalian packaging cells. In a preferred embodiment, viral particles are produced in insect cells using the baculovirus system as described by Gao, et al. (Gao et al. (2007), J. Biotechnol. 131(2):138-43). A meganuclease under the control of a mammalian promoter is unlikely to be expressed in these cells (Airenne et al. (2013), Mol. Ther. 21(4):739-49). Moreover, insect cells utilize different mRNA splicing motifs than mammalian cells. Thus, it is possible to incorporate a mammalian intron, such as the human growth hormone (HGH) intron or the SV40 large T antigen intron, into the coding sequence of a meganuclease. Because these introns are not spliced efficiently from pre-mRNA transcripts in insect cells, insect cells will not express a functional meganuclease and will package the full-length genome. In contrast, mammalian cells to which the resulting recombinant AAV particles are delivered will properly splice the pre-mRNA and will express functional meganuclease protein. Haifeng Chen has reported the use of the HGH and SV40 large T antigen introns to attenuate expression of the toxic proteins barnase and diphtheria toxin fragment A in insect packaging cells, enabling the production of recombinant AAV vectors carrying these toxin genes (Chen (2012), Mol Ther Nucleic Acids. 1(11): e57).

The meganuclease gene can be operably linked to an inducible promoter such that a small-molecule inducer is required for meganuclease expression. Examples of inducible promoters include the Tet-On system (Clontech; Chen et al. (2015), BMC Biotechnol. 15(1):4)) and the RheoSwitch system (Intrexon; Sowa et al. (2011), Spine, 36(10): E623-8). Both systems, as well as similar systems known in the art, rely on ligand-inducible transcription factors (variants of the Tet Repressor and Ecdysone receptor, respectively) that activate transcription in response to a small-molecule activator (Doxycycline or Ecdysone, respectively). Practicing the current invention using such ligand-inducible transcription activators includes: 1) placing the meganuclease gene under the control of a promoter that responds to the corresponding transcription factor, the meganuclease gene having (a) binding site(s) for the transcription factor; and 2) including the gene encoding the transcription factor in the packaged viral genome The latter step is necessary because the meganuclease will not be expressed in the target cells or tissues following recombinant AAV delivery if the transcription activator is not also provided to the same cells. The transcription activator then induces meganuclease gene expression only in cells or tissues that are treated with the cognate small-molecule activator. This approach is advantageous because it enables meganuclease gene expression to be regulated in a spatio-temporal manner by selecting when and to which tissues the small-molecule inducer is delivered. However, the requirement to include the inducer in the viral genome, which has significantly limited carrying capacity, creates a drawback to this approach.

In another preferred embodiment, recombinant AAV particles are produced in a mammalian cell line that expresses a transcription repressor that prevents expression of the meganuclease. Transcription repressors are known in the art and include the Tet-Repressor, the Lac-Repressor, the Cro repressor, and the Lambda-repressor. Many nuclear hormone receptors such as the ecdysone receptor also act as transcription repressors in the absence of their cognate hormone ligand. To practice the current invention, packaging cells are transfected/transduced with a vector encoding a transcription repressor and the meganuclease gene in the viral genome (packaging vector) is operably linked to a promoter that is modified to comprise binding sites for the repressor such that the repressor silences the promoter. The gene encoding the transcription repressor can be placed in a variety of positions. It can be encoded on a separate vector; it can be incorporated into the packaging vector outside of the ITR sequences; it can be incorporated into the cap/rep vector or the adenoviral helper vector; or it can be stably integrated into the genome of the packaging cell such that it is expressed constitutively. Methods to modify common mammalian promoters to incorporate transcription repressor sites are known in the art. For example, Chang and Roninson modified the strong, constitutive CMV and RSV promoters to comprise operators for the Lac repressor and showed that gene expression from the modified promoters was greatly attenuated in cells expressing the repressor (Chang and Roninson (1996), Gene 183:137-42). The use of a non-human transcription repressor ensures that transcription of the meganuclease gene will be repressed only in the packaging cells expressing the repressor and not in target cells or tissues transduced with the resulting recombinant AAV vector.

2.7 Engineered Nuclease Variants

Embodiments of the invention encompass the engineered nucleases described herein, and variants thereof. Further embodiments of the invention encompass polynucleotides comprising a nucleic acid sequence encoding the nucleases described herein, and variants of such polynucleotides.

As used herein, "variants" is intended to mean substantially similar sequences. A "variant" polypeptide is intended to mean a polypeptide derived from the "native" polypeptide by deletion or addition of one or more amino acids at one or more internal sites in the native protein and/or substitution of one or more amino acids at one or more sites in the native polypeptide. As used herein, a "native" polynucleotide or polypeptide comprises a parental sequence from which variants are derived. Variant polypeptides encompassed by the embodiments are biologically active. That is, they continue to possess the desired biological activity of the native protein; i.e., the ability to recognize and cleave the TRC 1-2 recognition sequence (SEQ ID NO: 5) found in the human T cell receptor alpha constant region (SEQ ID NO: 3), and in some embodiments, exhibit at least one improved property over the first-generation TRC 1-2 meganucleases selected from the group consisting of improved (i.e., increased) specificity and off-target cutting, reduced persistence time in cells, and enhanced (i.e., increased) efficiency of modification of TCR alpha constant region gene. Such variants may result, for example, from human manipulation. Biologically active variants of a native polypeptide of the embodiments (e.g., SEQ ID NOs: 7 and 8), or biologically active variants of the recognition half-site binding subunits described herein, will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, or about 99%, sequence identity to the amino acid sequence of the native polypeptide or native subunit, as determined by sequence alignment programs and parameters described elsewhere herein. A biologically active variant of a polypeptide or subunit of the embodiments may differ from that polypeptide or subunit by as few as about 1-40 amino acid residues, as few as about 1-20, as few as about 1-10, as few as about 5, as few as 4, 3, 2, or even 1 amino acid residue.

The polypeptides of the embodiments may be altered in various ways including amino acid substitutions, deletions, truncations, and insertions. Methods for such manipulations are generally known in the art. For example, amino acid sequence variants can be prepared by mutations in the DNA. Methods for mutagenesis and polynucleotide alterations are well known in the art. See, for example, Kunkel (1985) Proc. Natl. Acad. Sci. USA 82:488-492; Kunkel et al. (1987) Methods in Enzymol. 154:367-382; U.S. Pat. No. 4,873,192; Walker and Gaastra, eds. (1983) Techniques in Molecular Biology (MacMillan Publishing Company, New York) and the references cited therein. Guidance as to appropriate amino acid substitutions that do not affect biological activity of the protein of interest may be found in the model of Dayhoff et al. (1978) Atlas of Protein Sequence and Structure (Natl. Biomed. Res. Found., Washington, D.C.), herein incorporated by reference. Conservative substitutions, such as exchanging one amino acid with another having similar properties, may be optimal.

In some embodiments, engineered meganucleases of the invention can comprise variants of the HVR1 and HVR2 regions disclosed herein. Parental HVR regions can comprise, for example, residues 24-79 or residues 215-270 of the exemplified engineered meganucleases. Thus, variant HVRs can comprise an amino acid sequence having at least 80%, at least 85%, at least 90%, at least 91%, at least 92%, at least 93%, at least 94%, at least 95%, at least 96%, at least 97%, at least 98%, at least 99%, or more, sequence identity to an amino acid sequence corresponding to residues 24-79 or residues 215-270 of the engineered meganucleases exemplified herein, such that the variant HVR regions maintain the biological activity of the engineered meganuclease (i.e., binding to and cleaving the recognition sequence). Further, in some embodiments of the invention, a variant HVR1 region or variant HVR2 region can comprise residues corresponding to the amino acid residues found at specific positions within the parental HVR. In this context, "corresponding to" means that an amino acid residue in the variant HVR is the same amino acid residue (i.e., a separate identical residue) present in the parental HVR sequence in the same relative position (i.e., in relation to the remaining amino acids in the parent sequence). By way of example, if a parental HVR sequence comprises a serine residue at position 26, a variant HVR that "comprises a residue corresponding to" residue 26 will also comprise a serine at a position that is relative (i.e., corresponding) to parental position 26.

In particular embodiments, engineered meganucleases of the invention comprise an HVR1 region that has at least 90%, at least 91%, at least 92%, at least 93%, at least 94%, at least 95%, at least 96%, at least 97%, at least 98%, at least 99%, or more sequence identity to an amino acid sequence corresponding to residues 215-270 of SEQ ID NO: 7.

In certain embodiments, engineered meganucleases of the invention comprise an HVR2 region that has at least at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of SEQ ID NO: 7.

In some embodiments, engineered meganucleases of the invention comprise an HVR2 region that has at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or more sequence identity to an amino acid sequence corresponding to residues 24-79 of SEQ ID NO: 8.

In particular embodiments, engineered meganucleases of the invention comprise an HVR1 region that has at least 97% sequence identity to an amino acid sequence corresponding to residues 215-270 of SEQ ID NO: 7 and an HVR2 region that has at least 81% sequence identity to an amino acid sequence corresponding to residues 24-79 of SEQ ID NO: 7.

In other particular embodiments, engineered meganucleases of the invention comprise an HVR1 region having an amino acid sequence that corresponds to residues 215-270 of SEQ ID NO: 8 and an HVR2 region that has at least 86% sequence identity to an amino acid sequence corresponding to residues 24-79 of SEQ ID NO: 8.

A substantial number of amino acid modifications to the DNA recognition domain of the wild-type I-CreI meganuclease have previously been identified (e.g., U.S. Pat. No. 8,021,867) which, singly or in combination, result in recombinant meganucleases with specificities altered at individual bases within the DNA recognition sequence half-site, such that the resulting rationally-designed meganucleases have half-site specificities different from the wild-type enzyme. Table 2 provides potential substitutions that can be made in an engineered meganuclease monomer or subunit to enhance specificity based on the base present at each half-site position (−1 through −9) of a recognition half-site.

TABLE 2

| | Favored Sense-Strand Base | | | | | | | | | | |
|---|---|---|---|---|---|---|---|---|---|---|---|
| Posn. | A | C | G | T | A/T | A/C | A/G | C/T | G/T | A/G/T | A/C/G/T |
| −1 | Y75 | R70* | K70 | Q70* | | | | T46* | | | G70 |
| | L75* | H75* | E70* | C70 | | | | | | | A70 |
| | C75* | R75* | E75* | L70 | | | | | | | S70 |
| | Y139* | H46* | E46* | Y75* | | | | | | | G46* |
| | C46* | K46* | D46* | Q75* | | | | | | | |
| | A46* | R46* | | H75* | | | | | | | |
| | | | | H139 | | | | | | | |
| | | | | Q46* | | | | | | | |
| | | | | H46* | | | | | | | |
| −2 | Q70 | E70 | H70 | Q44* | C44* | | | | | | |
| | T44* | D70 | D44* | | | | | | | | |
| | A44* | K44* | E44* | | | | | | | | |
| | V44* | R44* | | | | | | | | | |
| | I44* | | | | | | | | | | |
| | L44* | | | | | | | | | | |
| | N44* | | | | | | | | | | |
| −3 | Q68 | E68 | R68 | M68 | | H68 | | Y68 | K68 | | |
| | C24* | F68 | | C68 | | | | | | | |
| | I24* | K24* | | L68 | | | | | | | |
| | | R24* | | F68 | | | | | | | |
| −4 | A26* | E77 | R77 | | | | | S77 | | S26* | |
| | Q77 | K26* | E26* | | | | | Q26* | | | |
| −5 | | E42 | R42 | | | K28* | C28* | | | M66 | |
| | | | | | | | Q42 | | | K66 | |
| −6 | Q40 | E40 | R40 | C40 | A40 | | | | | S40 | |
| | C28* | R28* | | I40 | A79 | | | | | S28* | |
| | | | | V40 | A28* | | | | | | |
| | | | | C79 | H28* | | | | | | |
| | | | | I79 | | | | | | | |
| | | | | V79 | | | | | | | |
| | | | | Q28* | | | | | | | |
| −7 | N30* | E38 | K38 | I38 | | C38 | | | | H38 | |
| | Q38 | K30* | R38 | L38 | | | | | | N38 | |
| | | R30* | E30* | | | | | | | Q30* | |
| −8 | F33 | E33 | F33 | L33 | | R32* | R33 | | | | |
| | Y33 | D33 | H33 | V33 | | | | | | | |
| | | | | I33 | | | | | | | |
| | | | | F33 | | | | | | | |
| | | | | C33 | | | | | | | |
| −9 | | E32 | R32 | L32 | | | | | D32 | S32 | |
| | | | K32 | V32 | | | | | I32 | N32 | |
| | | | | A32 | | | | | | H32 | |
| | | | | C32 | | | | | | Q32 | |
| | | | | | | | | | | T32 | |

Bold entries are wild-type contact residues and do not constitute "modifications" as used herein. An asterisk indicates that the residue contacts the base on the antisense strand.

Certain modifications can be made in an engineered meganuclease monomer or subunit to modulate DNA-binding affinity and/or activity. For example, an engineered meganuclease monomer or subunit described herein can comprise a G, S, or A at a residue corresponding to position 19 of I-CreI or SEQ ID NO: 7 or 8 (WO 2009001159), a Y, R, K, or D at a residue corresponding to position 66 of I-CreI or SEQ ID NO: 7 or 8, and/or an E, Q, or K at a residue corresponding to position 80 of I-CreI or SEQ ID NO: 7 or 8 (U.S. Pat. No. 8,021,867).

For polynucleotides, a "variant" comprises a deletion and/or addition of one or more nucleotides at one or more sites within the native polynucleotide. One of skill in the art will recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Variant polynucleotides include synthetically derived polynucleotides, such as those generated, for example, by using site-directed mutagenesis but which still encode a recombinant nuclease of the embodiments. Generally, variants of a particular polynucleotide of the embodiments will have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs and parameters described elsewhere herein. Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide.

The deletions, insertions, and substitutions of the variant protein sequences encompassed herein are not expected to produce radical changes in the characteristics of the polypeptide. However, when it is difficult to predict the exact effect of the substitution, deletion, or insertion in advance of doing so, one skilled in the art will appreciate that the effect will be evaluated by screening the polypeptide for its ability to preferentially recognize and cleave the TRC 1-2 recognition sequence (SEQ ID NO: 5) found within exon 1 of the human T cell receptor alpha constant region gene (SEQ ID NO: 3).

EXAMPLES

This invention is further illustrated by the following examples, which should not be construed as limiting. Those skilled in the art will recognize, or be able to ascertain, using no more than routine experimentation, numerous equivalents to the specific substances and procedures described herein. Such equivalents are intended to be encompassed in the scope of the claims that follow the examples below.

Example 1

Characterization of Meganucleases Having Specificity for the TRC 1-2 Recognition Sequence 1. Meganucleases that Recognize and Cleave the TRC 1-2 Recognition Sequence The second-generation TRC 1-2 meganucleases, referred to as TRC 1-2L.1592 (SEQ ID NO: 7) and TRC 1-2L.1775 (SEQ ID NO: 8), were engineered to recognize and cleave the TRC 1-2 recognition sequence (SEQ ID NO: 5), which is present in the human T cell receptor alpha constant region. Each of these second-generation meganucleases comprises an N-terminal nuclease-localization signal derived from SV40, a first meganuclease subunit, a linker sequence, and a second meganuclease subunit. A first subunit in each TRC 1-2 meganuclease binds to the TRC1 recognition half-site of SEQ ID NO: 5, while a second subunit binds to the TRC2 recognition half-site (see, FIG. 1). TRC1-binding subunits and TRC2-binding subunits each comprise a 56 base pair hypervariable region, referred to as HVR1 and HVR2, respectively.

The HVR1 region of each TRC1-binding subunit consists of residues 215-270 of SEQ ID NOs: 7 and 8. TRC1-binding subunits of TRC 1-2L.1592 and TRC 1-2L.1775 are identical to one another outside of the HVR1 region. The HVR1 region of each TRC 1-2 meganuclease comprises modifications relative to the wild-type I-CreI sequence (SEQ ID NO: 1) at positions 215, 217, 219, 221, 223, 224, 229, 231, 233, 235, 237, 259, 266, and 268. Although not modified relative to wild-type I-CreI, the arginine residue at position 261 of SEQ ID NOs: 7 and 8 is believed to contribute, in combination with the modified HVR1 residues, to specificity of the nuclease. The HVR1 region of TRC 1-2L.1592 shares 96.43% sequence identity to the HVR1 region of TRC 1-2x.87EE meganuclease. The HVR1 region of TRC 1-2L.1775 shares 100% sequence identity to the HVR1 region of the TRC 1-2x.87EE meganuclease.

The HVR2 region of each TRC2-binding subunit consists of residues 24-79 of SEQ ID NOs: 7 and 8. TRC2-binding subunits of TRC 1-2L.1592 and TRC 1-2L.1775 are identical to one another outside of the HVR2 region, except at position 80 of SEQ ID NOs: 7 and 8 which can be E (TRC 1-2L.1592) or Q (TRC 1-2L.1775). The HVR2 region of each TRC 1-2 meganuclease comprises modifications relative to the wild-type I-CreI sequence (SEQ ID NO: 1) at positions 24, 26, 28, 30, 32, 33, 38, 40, 42, 44, 46, 48, 50, 68, 70, 75, and 77. The TRC 1-2L.1592 meganuclease further contains modifications at positions 71, 72, and 73 relative to wild-type I-CreI. It is also notable that the arginine residue at position 139 of SEQ ID NOs: 7 and 8 is modified relative to the wild-type I-CreI sequence, and is believed to contribute, in combination with the modified HVR2 residues, to specificity of the nuclease. The HVR2 region of TRC 1-2L.1592 shares only 80.36% sequence identity to the HVR2 region of the first-generation TRC 1-2x.87EE meganuclease. The HVR2 region of TRC 1-2L.1775 shares only 85.71% sequence identity to the HVR2 region of the TRC 1-2x.87EE meganuclease.

2. Optimization of First-Generation TRC 1-2 Nucleases

The previously reported TRC 1-2x.87EE meganuclease was evaluated for recognition site specificity using a method very similar to GUIDE-seq (Tsai et al. (2015), Nat Biotechnology 33:187-197) but adjusted to find potential off-target sites for meganucleases. In general, potential off-target sites are identified by capturing a probe oligonucleotide in the double strand DNA break. The TRC 1-2 meganucleases generate a four base pair 3' overhang, so the probe oligo also contains randomized four base pair overhangs to improve ligation efficiency at sites more likely created by the nuclease cleavage.

Specificity analysis of TRC 1-2x.87EE found a variety of potential off-target sites in human T cells. These off-targets could be grouped into two concerning categories: unique targets that were hit at high frequency and repeating targets that were hit at low frequency. Key amino acids that are involved in recognition of these off-targets were re-randomized. Subsequently, simultaneous selection was run for cutting the intended site and counter selection to not cut an off-target site. The off-target site was alternated between successive rounds of selection to isolate answers (i.e., nucleases) that would discriminate against both off targets. The two off-targets used were Off1: 5'-TGGCCTG-GAGaAACAgtgtaaa-3' (SEQ ID NO: 16), which is a low frequency cut but highly repeated site in the genome, and Off2: 5'-cGGCCTGtAGtAcaggAcCTGA-3' (SEQ ID NO: 17), which is a frequently hit, unique off-target (lowercase letters represent mismatches from intended site). A variety of nuclease libraries were used.

After selection, 96 well plates of isolated clones from each successful library were prepared to isolate plasmid DNA. Each plasmid DNA was individually transfected into CHO cells containing an integrated target site in an interruption between two direct repeats in a GFP gene. Cleaving the target site results in repair of the GFP gene by single strand annealing and the frequency of cutting the target site can be counted by counting the number of GFP positive cells on a flow cytometer. We assayed the nuclease plasmids against cells with the intended site and the Off1 target sites. In this way, we could evaluate which nucleases were still cutting the intended site but discriminating against the off-target best. We identified five candidates. Three candidates were re-isolated from the original library for TRC 1-2: L.1462, L.1466, and L.1469. All three answers were unique but related to each other. Two candidates were isolated from TRC-library 2: L.1108 and L.1118. Each of these candidates represent intermediate nucleases in the development of the second-generation nucleases of the invention.

To further improve the nucleases, key amino acids involved in recognition site specificity were randomized. L.1462, L.1466, and L.1469 were collected into one library and L.1108 and L.1118 into a second library. New randomization by PCR was introduced into both. A similar selection strategy was followed with the new libraries; simultaneously selecting for the intended site and against Off1 or Off2. The off-targets were alternated between rounds of selection. 96 well plates of individual answers were generated from the selections and tested in the CHO iGFFP assay to determine cutting of the intended site and both Off1 and Off2. Several new nucleases were identified from this additional round of optimization. Answers from libraries based on L.1462, L.1466, and L.1469 included: L.1775 and L.1843. One answer from the library based on L.1108 and L.1118: L.1592. All of the new nucleases demonstrated strong activity towards the intended target and strong discrimination against both off-targets (as further described below). The new nucleases were run through an oligo capture assay (described further below) to determine the potential off-target sites and demonstrated that in general, the number of potential off-targets were reduced and in particular, L.1592 had very few potentially legitimate off-target sites. L.1108, L.1469, L.1592, L.1775, and L.1843 were further evaluated in the iGFFP assay over a seven day period to assay stability of the GFP signal over time which is a general measurement for toxicity. L.1469, L.1592, L.1775, and L.1843 were further tested in primary T cells for function.

3. Evaluation of TRC 1-2 Recognition Sequence Cleavage and Off-Target Cutting

Figure 3:
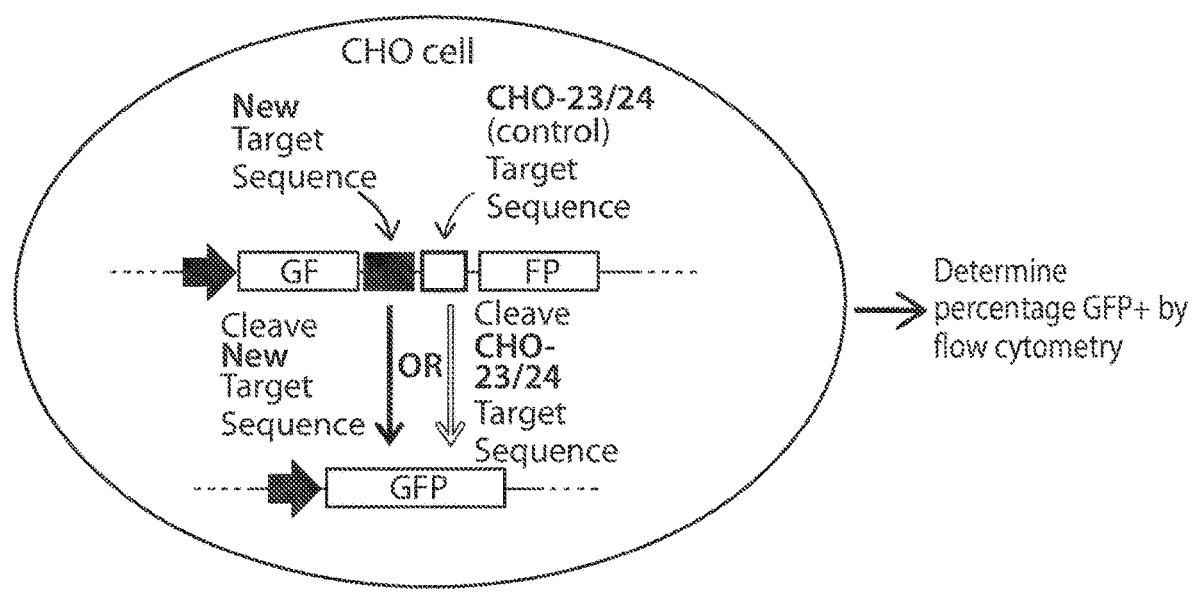
FIG. 3. Schematic of reporter assay in CHO cells for evaluating engineered meganucleases of the invention. A CHO cell line was produced in which a reporter cassette was integrated stably into the genome of the cell. The reporter cassette comprised, in 5' to 3' order: an SV40 Early Promoter; the 5'⅔ of the GFP gene; the recognition sequence for an engineered meganuclease of the invention (e.g., the TRC 1-2 recognition sequence); the recognition sequence for the CHO 23/24 meganuclease (WO/2012/167192); and the 3'⅔ of the GFP gene. Cells stably transfected with this cassette did not express GFP in the absence of a DNA break-inducing agent. Meganucleases were introduced by transduction of plasmid DNA or mRNA encoding each meganuclease. When a DNA break was induced at either of the meganuclease recognition sequences, the duplicated regions of the GFP gene recombined with one another to produce a functional GFP gene. The percentage of GFP-expressing cells could then be determined by flow cytometry as an indirect measure of the frequency of genome cleavage by the meganucleases.

To determine whether TRC 1-2 meganucleases could recognize and cleave the TRC 1-2 recognition sequence (SEQ ID NO: 5), each TRC 1-2 meganuclease was evaluated using the CHO cell reporter assay previously described (see WO/2012/167192, FIG. 3). To perform the assay, a pair of CHO cell reporter cell lines were produced which carried a non-functional Green Fluorescent Protein (GFP) gene expression cassette integrated into the genome of the cell. The GFP gene in each cell line was interrupted by a pair of recognition sequences such that intracellular cleavage of either recognition sequence by a meganuclease would stimulate a homologous recombination event resulting in a functional GFP gene. In both cell lines, one of the recognition sequences was derived from the TRC 1-2 gene and the second recognition sequence was specifically recognized by a control meganuclease called "CHO 23/24". CHO reporter cells comprising the TRC 1-2 recognition sequence (SEQ ID NO: 5) and the CHO 23/24 recognition sequence are referred to herein as "TRC 1-2 cells."

Figure 4:
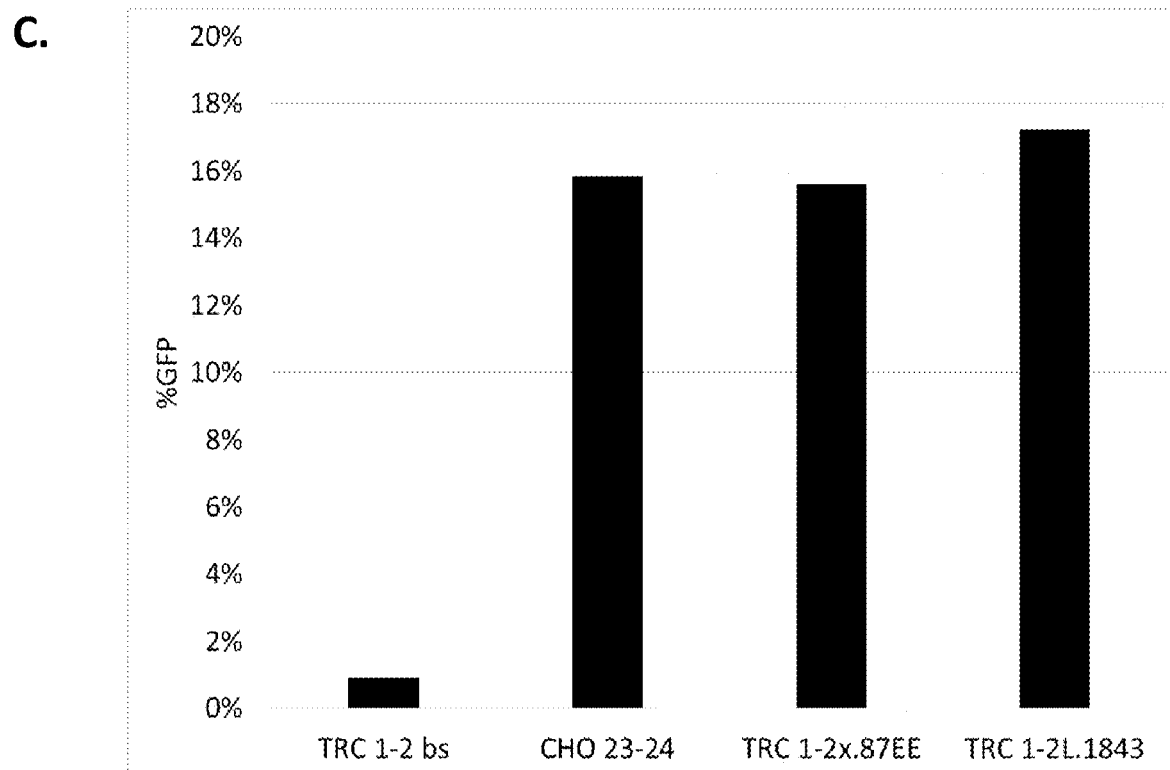
FIG. 4. Efficiency of engineered meganucleases for recognizing and cleaving the TRC 1-2 recognition sequence in a CHO cell reporter assay. The TRC 1-2L.1592, TRC 1-2L.1775, and TRC 1-2L.1843 meganucleases were engineered to target the TRC 1-2 recognition sequence (SEQ ID NO: 5), and were screened for efficacy in the CHO cell reporter assay. The results shown provide the percentage of GFP-expressing cells observed, which indicates the efficacy of each meganuclease for cleaving the target recognition sequence or the CHO 23/24 recognition sequence. A negative control (bs) and the first-generation TRC 1-2x.87EE were further included in the assay for comparison. A) CHO reporter assay evaluating TRC 1-2L.1592. B) CHO reporter assay evaluating TRC 1-2L.1775. C) CHO reporter assay evaluating TRC 1-2L.1843.

TRC 1-2 cells were transfected with plasmid DNA encoding one of the TRC 1-2 meganucleases (e.g., TRC 1-2x.87EE, TRC 1-2L.1592, TRC 1-2L.1775, or TRC 1-2L.1843) or encoding the CHO 23/34 meganuclease. 4e5 CHO cells were transfected with 50 ng of plasmid DNA in a 96-well plate using Lipofectamine 2000 (ThermoFisher) according to the manufacturer's instructions. At 48 hours post-transfection, cells were evaluated by flow cytometry to determine the percentage of GFP-positive cells compared to an untransfected negative control (1-2 bs). All TRC 1-2 meganucleases were found to produce GFP-positive cells in cell lines comprising the TRC 1-2 recognition sequence at frequencies significantly exceeding the negative control and comparable to or exceeding the CHO 23/24 positive control, indicating that each TRC 1-2 meganuclease was able to efficiently recognize and cleave the intended TRC 1-2 recognition sequence in a cell (FIG. 4A-4C).

Figure 5:
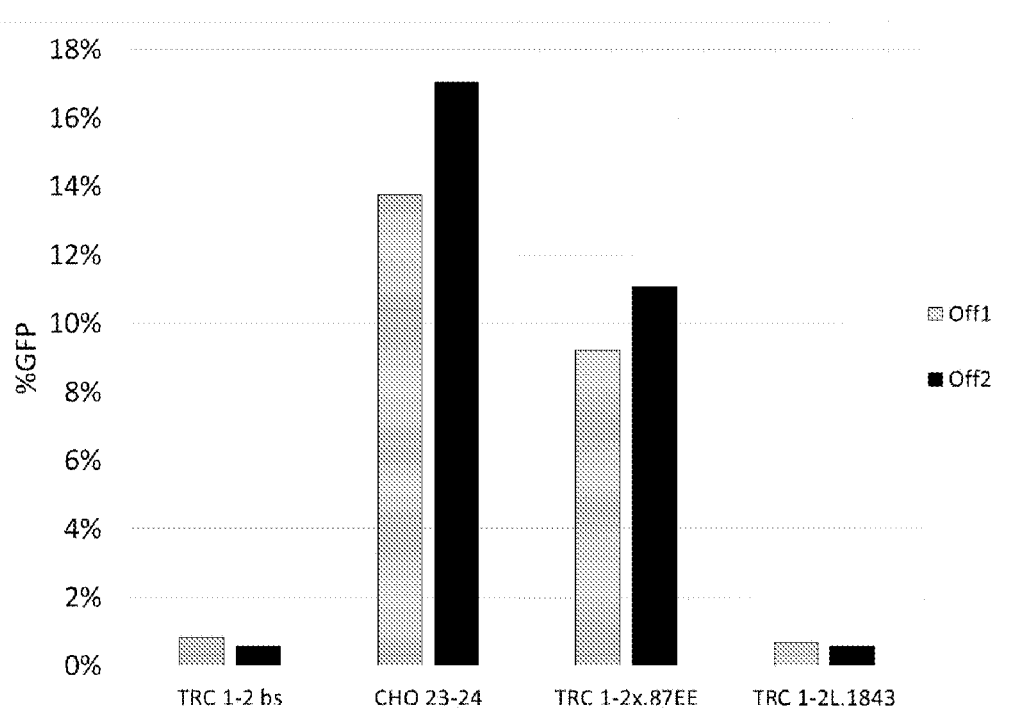
FIG. 5. Efficiency of engineered meganucleases for recognizing and cleaving the TRC Off1 recognition sequence (SEQ ID NO: 16) and the TRC Off2 recognition sequence (SEQ ID NO: 17) in a CHO cell reporter assay. mRNA encoding TRC 1-2 meganucleases of the invention were transfected into CHO reporter cells which contain the counter selected Off1 recognition sequence or the Off2 recognition sequence between the GFP direct repeats, as well as a CHO 23-24 recognition sequence. The second-generation meganucleases were compared in each assay against the first-generation TRC 1-2x.87EE meganuclease. A) Cleavage of the off-target recognition sequences by TRC 1-2L.1592 and TRC 1-2x.87EE. B) Cleavage of the off-target recognition sequences by TRC 1-2L.1775 and TRC 1-2x.87EE. C) Cleavage of the off-target recognition sequences by TRC 1-2L.1843 and TRC 1-2x.87EE.

Alternatively, the TRC 1-2 meganucleases were also transfected into TRC Off1 and TRC Off2 cells which contain the counter selected off-target sequences between the GFP direct repeats. Unlike the intended target site TRC 1-2 CHO cells, a desirable nuclease in TRC Off1 and TRC Off2 CHO cells has only background level GFP positive cells because it is able to discriminate against cutting the off-target sequence. The CHO 23-24 target site acts as a positive control in these experiments, demonstrating that the GFP can still be produced if the target site is cut by the CHO 23-24 nuclease. The new nucleases demonstrated a significantly improved (i.e., increased) discrimination against the Off1 and Off2 target sites compared to TRC 1-2 x.87EE, with % GFP at levels comparable to the TRC 1-2 bs negative control (FIG. 5A-5C).

Figure 6:
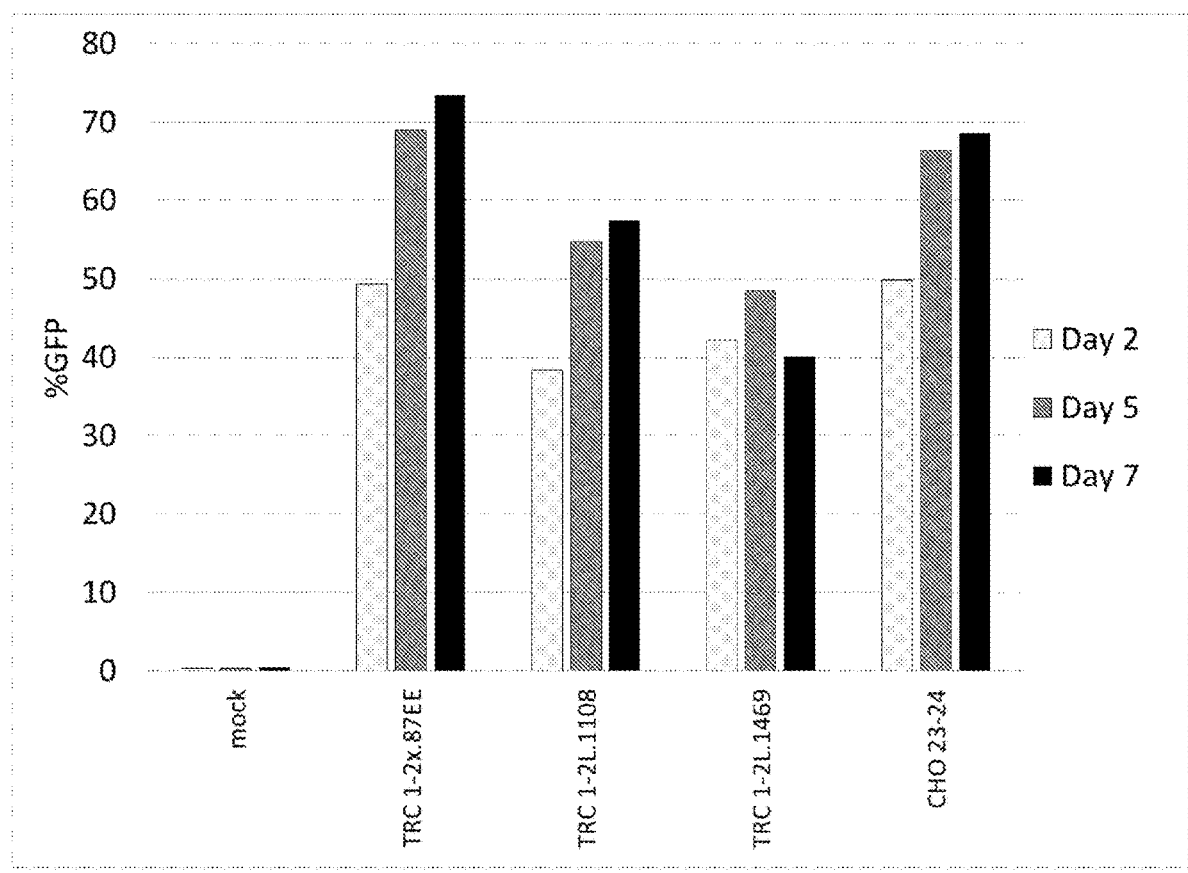
FIG. 6. Efficiency of engineered meganucleases for recognizing and cleaving the TRC 1-2 recognition sequence in a CHO cell reporter assay. The TRC 1-2x.87EE (first-generation), TRC 1-2L.1108 (intermediate), and TRC 1-2L.1469 (intermediate) meganucleases were engineered to target the TRC 1-2 recognition sequence (SEQ ID NO: 5), and were screened for efficacy in the CHO cell reporter assay at 2, 5, and 7 days after nucleofection in order to determine toxicity. The results shown provide the percentage of GFP-expressing cells observed over the 7 day period of analysis, which indicates the efficacy of each meganuclease for cleaving a target recognition sequence or the CHO 23/24 recognition sequence as a function of time.
Figure 7:
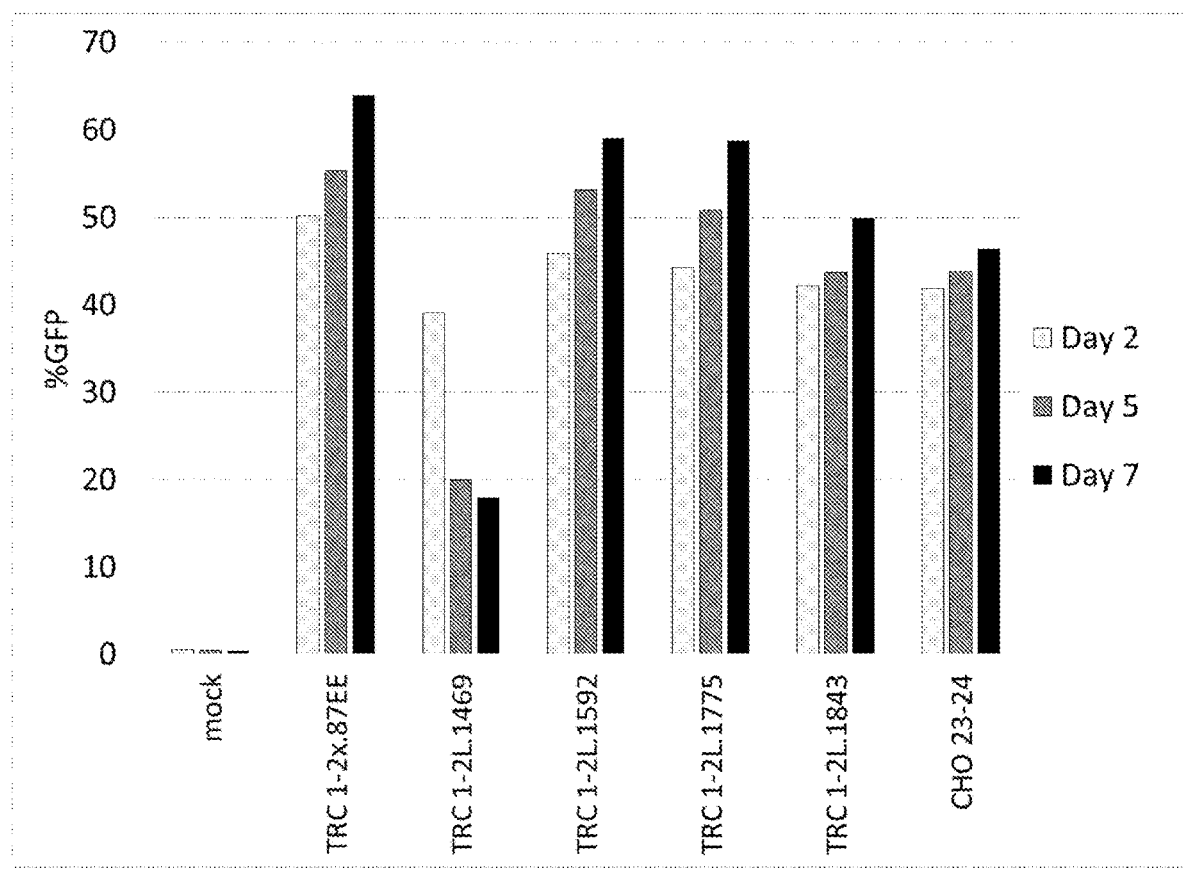
FIG. 7. Efficiency of engineered meganucleases for recognizing and cleaving the TRC 1-2 recognition sequence in a CHO cell reporter assay. The second-generation TRC 1-2L.1592, TRC 1-2L.1775, and TRC 1-2L.1843 meganucleases were optimized for targeting the TRC 1-2 recognition sequence (SEQ ID NO: 5), and were screened for efficacy in the CHO cell reporter assay at 2, 5, and 7 days after nucleofection in order to determine toxicity. The first-generation TRC 1-2x.87EE meganuclease, and the intermediate TRC 1-2L.1469 meganuclease, were also included in this assay for comparison. The results shown provide the percentage of GFP-expressing cells observed over the 7 day period of analysis, which indicates the efficacy of each meganuclease for cleaving a target recognition sequence or the CHO 23/24 recognition sequence as a function of time.

The efficacy of the TRC 1-2.L1469, L.1592, L.1775, and L.1843 engineered meganucleases was also determined in a time-dependent manner 2, 5, and 7 days after introduction of the meganucleases mRNA into TRC 1-2 cells. In this study, TRC 1-2 cells (1.0×106) were electroporated with 1×106 copies of meganuclease mRNA per cell using a BioRad Gene Pulser Xcell according to the manufacturer's instructions. At 48 hours post-transfection, cells were evaluated by flow cytometry to determine the percentage of GFP-positive cells. A CHO 23/24 meganuclease was also included at each time point as a positive control. Each of the meganucleases showed a comparable GFP-positive percentage relative to CHO 23-24 (FIG. 6 and FIG. 7). Only L.1469 demonstrated a decreasing trend in GFP-positive cells over time, indicating that it had some unresolved toxicity issues that were improved in the subsequent optimization. The remaining nucleases exhibited stable or increasing GFP-positive cells over time at levels equivalent to, or higher than, the CHO 23-24 control.

The extended iGFFP assay was also used to evaluate the same group of meganucleases for discrimination against the two off targets, Off1 and Off2, over a 7 day period. In this case, cells containing either Off1 or Off2 and CHO 23-24 were electroporated with 1×106 copies of meganuclease mRNA per cell using a BioRad Gene Pulser Xcell according to the manufacturer's instructions. At 2 days, 5 days, and 7 days post-transfection, cells were evaluated by flow cytometry to determine the percentage of GFP-positive cells. A CHO 23-24 meganuclease was also included at each time point as a positive control. Each of the nucleases showed improved discrimination against the off-target compared to TRC 1-2x.87EE (FIGS. 8A and 8B). L.1592 exhibited minimal cutting of either Off1 or Off2, comparable to mock control cells. L.1469 showed some detectable cutting of Off1 and Off2, though it was dramatically lower than that observed by TRC 1-2x.87EE. L.1775 and L.1843 show improvement over their parent, L.1469, in discrimination against the off-targets.

4. Oligo Capture Assay and Analysis of Off-Target Cutting

In these studies, an oligo capture assay was used to identify off target cutting induced by the TRC 1-2 meganucleases. Similar to GUIDE-seq, the oligo capture assay identifies potential off-target sites produced by the TRC 1-2 meganucleases by capturing an oligonucleotide at break sites within the cell's genomic DNA. GUIDE-seq was developed for CRISPR-Cas9 generated DNA breaks and there are a few key modifications to the chemistry and analysis in order to apply this technique to the present nucleases. Unlike CRISPR-cas9, the engineered meganucleases of the invention generate a four base pair 3' overhang. To accommodate for this difference, the oligonucleotides used in oligo capture have randomized four base pair overhangs that could be compatible with the overhangs generated with the TRC 1-2 meganuclease. A higher frequency of insertion is observed due to the greater efficiency of ligating sticky ends rather than blunt ends. Cells were transfected with mRNA encoding the nuclease and the double stranded DNA oligonucleotides. After two days, the genomic DNA from these cells was isolated and sonicated to shear the DNA to smaller sizes. An oligonucleotide adapter was ligated to the sheared DNA and PCR was used to amplify any DNA pieces that contain an adapter at one end and the captured oligonucleotide at the other end. The amplified DNA was purified and sequencing libraries were prepared using standard commercial kits.

Sequencing libraries were run on an Illumina MiSeq using V2 2×150 kits. The data was filtered and analyzed for valid sites that captured an oligonucleotide and a potential off-target site is predicted. Here again, the protocol needed to be adjusted from the PAM search used for CRISPR-cas9 to the TRC 1-2 meganuclease search. The software developed checks each sequence to make sure there is adapter and captured oligo flanking the sequence to verify that it is a valid read. The software also checks for PCR duplicates and removes reads that are identical to help reduce PCR bias. The sequence reads are aligned to a reference genome and grouped sequences within thousand base pair windows are scanned for a potential TRC 1-2 meganuclease site.

Each TRC 1-2 meganuclease is a linked dimer. Each monomer recognizes a nine base pair half site with a four base pair spacer in the center between the two half sites. The software looks for the closest sequence match for each half site with no allowed gaps. The middle four base pairs are not considered in the off-target selection because the TRC 1-2 meganucleases can generally tolerate a higher amount of degeneracy at these positions in the target site. The software outputs a list of potential off-target sites with the number of base mismatches in the combined half sites but not counting the middle four base pair mismatches. The software does not eliminate any off-targets based on an arbitrary mismatch filter, unlike CRISPR-Cas9 which eliminates any off-target identified with more than six base pairs mismatched. Instead, background noise generated from random capture of the oligo at fragile spots or hot spots within the genome can be reduced in two ways. First, an untreated mock sample is also run though oligo capture and windows of integration sites without the nuclease present can be subtracted from the nuclease containing samples. We have also found that running the assay in triplicate and eliminating any sites that do not repeat in at least two of the three repeats is a good way to empirically remove random integration noise.

Figure 9:
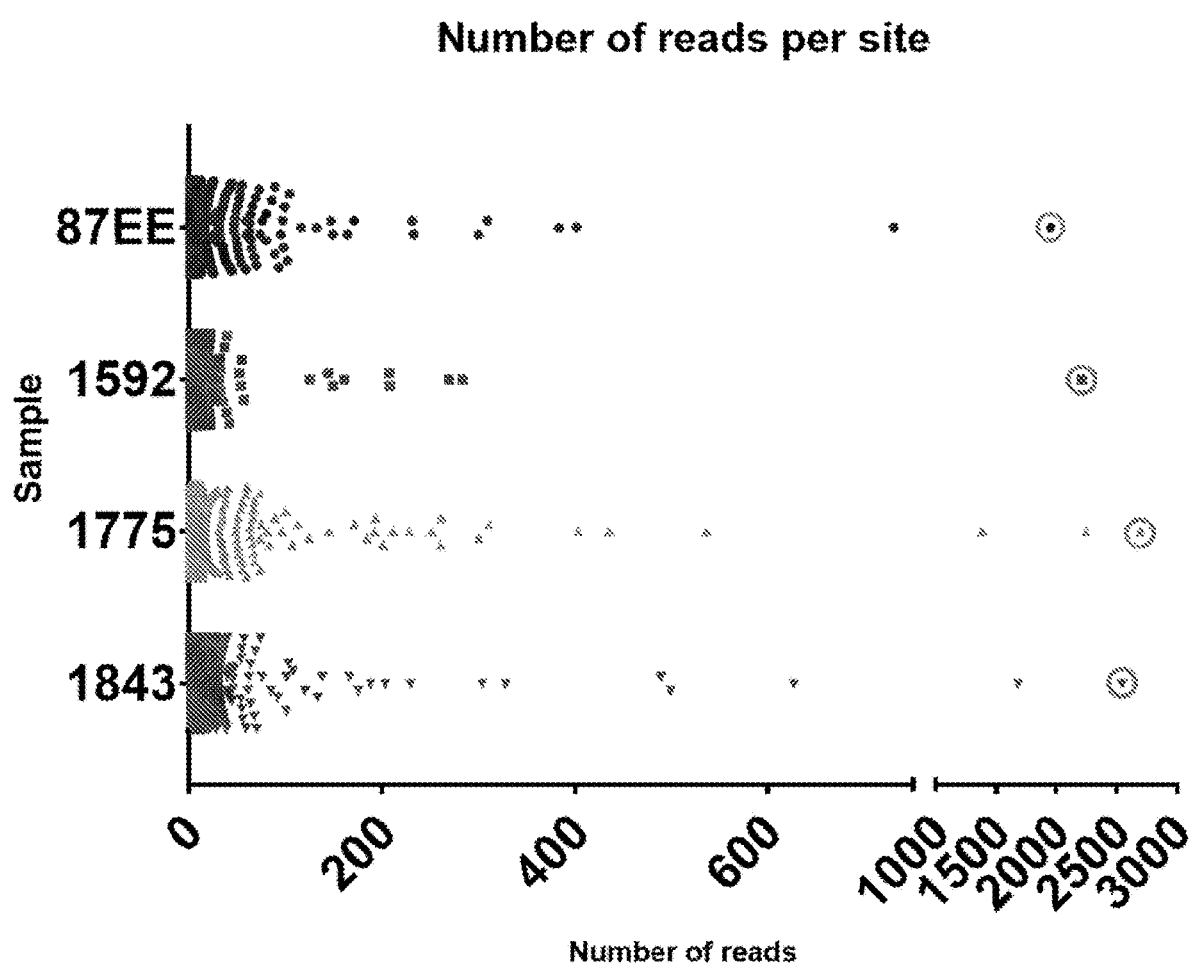
FIG. 9. Graphical visualization of oligo capture data as a measure of number of potentially valid off-target sites. Each off-target cut generated by a particular nuclease is plotted based on the number of unique sequence reads for a probe oligo being captured at that site. The intended site (i.e., the TRC 1-2 recognition sequence) has the highest read count for each meganuclease tested (circled).

Although read count does not directly correlate with cutting frequency at a particular site, it can generally highlight off-targets that are potentially more concerning or more valid because they occur more often. One way to graphically visualize the oligo capture data as a measure of number of potentially valid off-target sites is shown in FIG. 9. Each off-target generated by a particular nuclease is plotted based on the number of unique sequence reads for a probe oligo being captured at that site. The intended site should have the highest read count, which is the case for all the TRC 1-2 meganucleases tested. Better nucleases remove the higher count sites and have fewer dots above background noise at the far left of the plot. Using this plot, it is clear, for example, that TRC 1-2L.1592 removes more of the higher read count sites than the first-generation TRC 1-2x.87EE.

Figure 10:
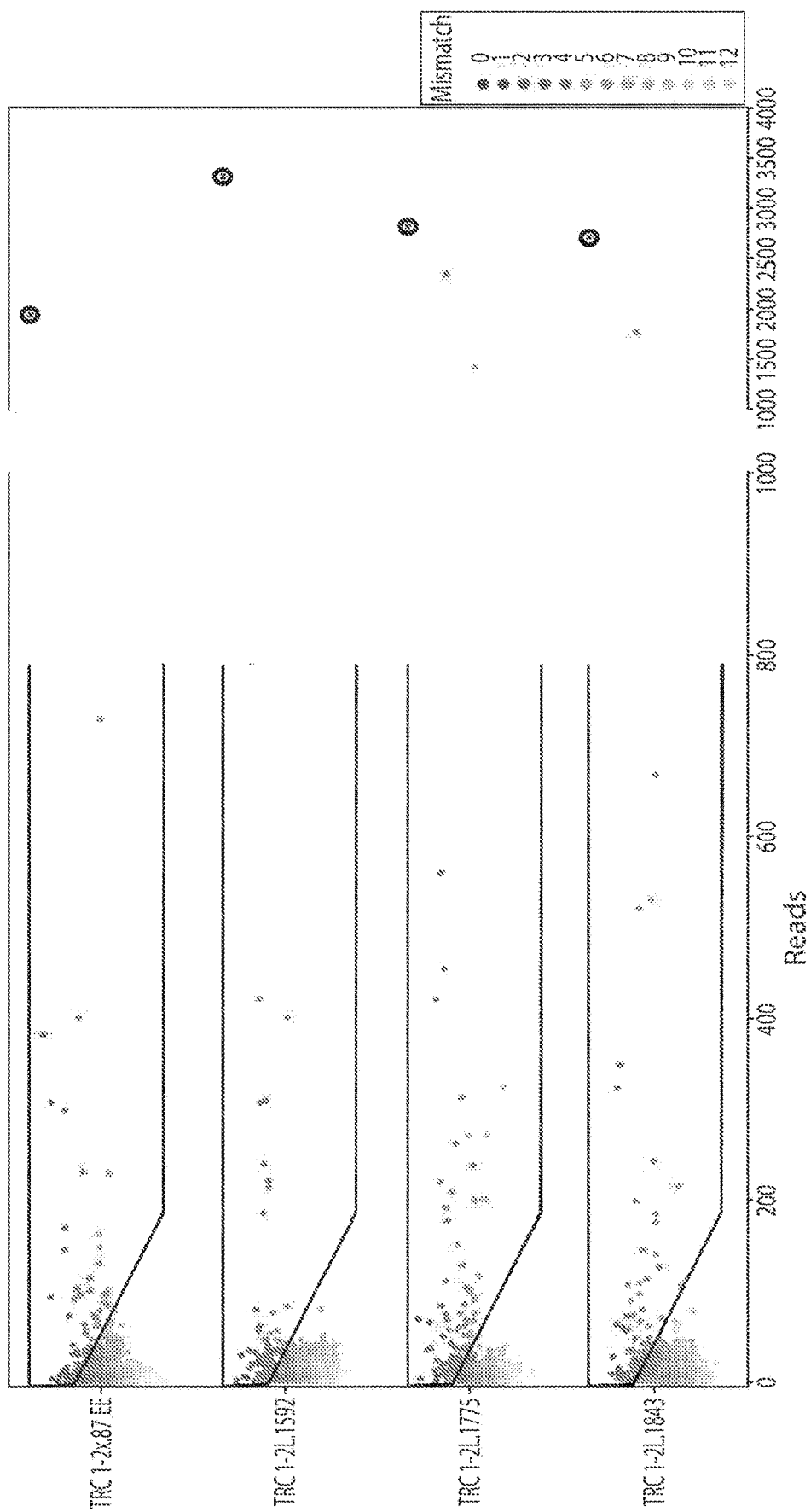
FIG. 10. Graphical visualization of oligo capture data wherein off target sites are plotted according to their number of aligned reads on the X axis, and the number of mismatched base pairs compared to the intended site are indicated by color, with darker colors indicating closer overall matches between off-targets and the intended binding site. The boxes indicate the zones of highest confidence.

Additional visualization methods enable us to look at the oligo capture data not only in terms of number of reads recovered at a particular site, but also by number of mismatches between a putative off-target site and the intended site. This allows for a more accurate determination of real oligo integrations sites as compared to random integration or sequencing noise. In FIG. 10, off target sites are plotted according to their number of aligned reads on the X axis, and the number of mismatched base pairs compared to the intended site are indicated by color, with darker colors indicating closer overall matches between off-targets and the intended binding site. The boxes indicate the zones of highest confidence. Off-targets within these boxes have either high aligned read counts or very high similarities to the intended site, either of which decrease the probability of the site being background noise. Comparing the sites in the confidence zone, FIG. 10 demonstrates the increased specificity of the optimized meganucleases, and particularly TRC 1-2L.1592, compared to TRC 1-2x.87 EE. TRC 1-2L.1592 shows a decrease in the number of higher read-count sites as well as a decrease in sites more similar to the intended.

Example 2

In Vitro Analysis of Optimized TRC 1-2 Meganuclease

1. Evaluation of Gene-Editing Efficiency, Post-Editing Expansion, and Differentiation In a first series of experiments, four optimized, second-generation TRC 1-2 meganucleases were screened for their gene-editing efficiencies, and for post-editing expansion and differentiation potential. Three different operators each evaluated all nuclease variants in T cells obtained from a different healthy human T cell donor. Apheresis material was sourced from donors K708, K799, and K6784 from Key Biologics (Memphis, Tenn.). K708 and K6784 T cells were processed according to the following protocol: T cell enrichment using human CD3 positive selection reagents (Stem-Cell Technologies), stimulation using ImmunoCult anti-CD2/CD3/CD28 (StemCell Technologies) and nuclease RNA delivery using the 4D NucleoFEctor (Lonza). T cells from K799 were processed according to the following protocol: T cell enrichment using CD4 and CD8 microbeads and the CliniMACS cell isolator (Miltenyi Biotec), stimulation using TransAct (Miltenyi), and nuclease RNA delivery using the MaxCyte-GT.

Editing efficiencies, expansion, and differentiation of four optimized nuclease variants (TRC 1-2L.1496, L.1592, L.1775, and L.1843) were compared against the progenitor nuclease TRC 1-2x.87EE and against T cells that were mock electroporated. Three days after initial stimulation with ImmunoCult/TransAct, T cells were harvested, electroporated with RNA encoding one of the nucleases, and immediately transduced with an AAV6 vector encoding a CAR gene to be inserted into the TRC 1-2 cleavage site. Control cultures receiving no AAV were assembled in parallel.

At days 4 and 8 post-editing, total culture cellularity was determined with the NucleoCounter NC-200 (ChemoMetec). Editing efficiency was determined by staining culture samples with antibodies directed against human CD3-PE (BioLegend clone UCHT1) and anti-FMC63scFv-AlexaFluor647 (novel clone produced and conjugated in-house). Differentiation was evaluated by comparing frequencies of central memory, transitional memory, and effector memory cells in both the CD4 and CD8 compartments using CD4-BV786 (clone OKT4 BioLegend), CD8-BV711 (clone RPA-T8, BioLegend), CD62L-BB515 (clone SK11 BD Biosciences), and CD45RO-PE/Cy7 (clone UCHL1, BioLegend).

The results of these experiments are summarized in FIG. 11. The knockout frequency of the endogenous T cell receptor (measured by T cells converting form a CD3-positive to a CD3-negative phenotype) was determined for each nuclease in 3 different donors. For all 3 donors tested (and using both cell preparation methods), both TRC 1-2L.1592 and L.1775 generated knockout cells at a similar or higher efficiency than TRC 1-2x.87EE. By comparison, L.1469 and L.1843 generated lower knockout frequencies. This was true for all 3 donors tested. L.1775 demonstrated slightly higher editing efficiencies than L.1592. Increased editing of the TRC 1-2 recognition sequence was associated with an increased insertion rate of the CAR gene. In all three donors, L.1592 and L.1775 supported equivalent or superior editing and insertion frequency.

At day 8 post-editing, cell counting data were used to calculate CAR T cell fold expansion. Across all three donors, L.1592, L.1775, and L.1843 promoted greater expansion following electroporation than x.87EE. By contrast, L.1469 promoted less expansion than x.87EE. In two of the three donors, L.1843 allowed the most extensive expansion of the three optimized nucleases. L.1775 supported a degree of expansion that varied from donor to donor.

The CD4:CD8 ratio and memory subset data were also captured on day 8 post-editing. Compared to x.87EE, no major perturbations to CD4:CD8 ratio was observed from any of the optimized nucleases, although L.1592, L.1775, and L.1843 typically resulted in a greater frequency of CD4+ cells. Compared to x.87EE, a greater degree of differentiation away from central memory and into transitional and effector memory populations was observed in cells edited with L.1469. In contrast, an equivalent or greater frequency of cells maintained a central memory phenotype when edited with L.1592, L.1775, or L.1843.

These studies show that three of the four optimized nucleases outperformed TRC 1-2 x.87EE in terms of editing efficiency, cell expansion, and differentiation characteristics. One nuclease, L.1469, did not perform as well as x.87EE. Of the three variants with improved in vitro function, variant L.1775 supports the highest frequency of edited cells in culture, but supports the lowest amount of post-editing expansion and accelerates the differentiation of T cells in culture. Variant L.1843 allows the greatest amount of post-editing expansion, and preserves a favorable central memory frequency, but is the less efficient than either L.1775 or L.1592 in terms of knockout frequency. Surprisingly, L.1592 represents an improvement over the first-generation x.87EE using all three of these criteria.

2. Oligo Capture Assay and Analysis of Off-Target Cutting

Figure 12:
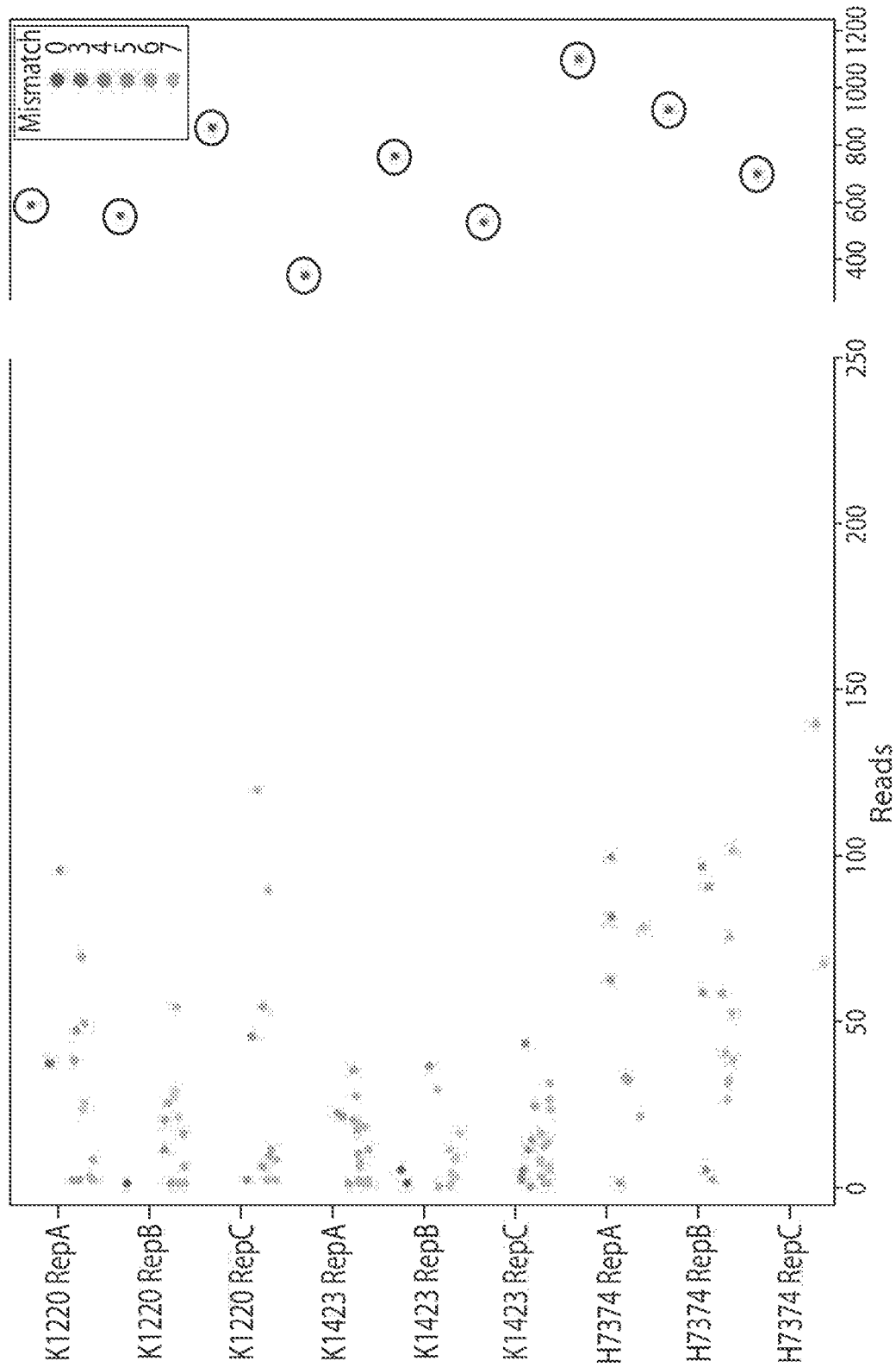
FIG. 12. Graphical visualization of oligo capture data generated in T cell populations obtained from three different healthy human donors.

Oligo capture was performed for three replicates of T cells obtained from each of the three donors using methods as previously described in Example 1. Results of oligo capture are shown in FIG. 12. Dots represent the number of sequencing reads recovered at each putative off-target site as well as the intended target site. Putative sites with more than 7 mismatches to the intended target were removed as no sites with more than 7 mismatches was shown to be cleaved by TRC 1-2L.1592 in previous studies. The intended target site for each sample is highlighted with a circle. The number of mismatches compared to the intended target is indicated by the darkness of each circle with fewer mismatches having darker colors. The plot represents the oligo capture data without mock background removed and with read counts normalized to the number of unique reads per sample to account for differences in total number of reads recovered. As shown, TRC 1-2L.1592 shows a low number of higher read-count sites, as well as a low number of sites more similar to the intended when used for editing and targeted insertion in CAR T cell populations.

3. In Vitro Studies of Editing Efficiency, Expansion, and Cytokine Secretion

In a second series of in vitro studies, second-generation optimized TRC 1-2 meganucleases were evaluated for their efficiency in editing T cells, the ability of edited T cells to expand after editing, and the ability of CAR T cells generated with the nuclease variants to respond to encounter with antigen-bearing target cells.

Apheresis material was sourced from donor K708 from Key Biologics (Memphis, Tenn.) and T cells were enriched using human CD3 positive selection reagents (StemCell Technologies), stimulated using ImmunoCult anti-CD2/CD3/CD28 (StemCell Technologies) and nuclease RNA was delivered using the 4D NucleoFector (Lonza). Triplicate samples were run in parallel.

Editing efficiencies, expansion, and differentiation of three optimized meganucleases (TRC 1-2L.1592, L.1775, and L.1843) were compared against the progenitor nuclease TRC 1-2x.87EE and against T cells that were mock electroporated. Three days after initial stimulation with ImmunoCult/TransAct, T cells were harvested, electroporated with RNA encoding one of the nucleases, and immediately transduced with an AAV6 vector encoding a CAR gene to be inserted into the TRC 1-2 cleavage site. At days 4 and 8 post-editing, cultures were sampled to determine editing efficiency and expansion using a Beckman-Coulter Cyto-FLEX-LX flow cytometer. Endogenous T cell receptor knockout efficiency was assessed using anti-CD3-PE (BioLegend clone UCHT1) and CAR knock-in was measured using anti-FMC62scFv-AlexaFluor647 (novel clone produced and conjugated in-house).

Proliferation, cytotoxicity, and cytokine production were assessed by co-culturing CART cells with the CD19+ tumor lines Raji or Nalm6 at E:T ratios of 1:1 and 1:2. CD19-negative K562 myelogenous leukemia cells were used as controls. Culture supernatants were collected and analyzed for secreted cytokine using the Luminex MAGPIX instrument and the MilliPlex MAP 15-plex bead set (Millipore). Proliferation and target killing were assessed by staining culture cell samples with anti-CD4-APC (BioLegend clone OKT4), anti-CD8-FITC (BioLegend clone RPA-T8), and anti-CD19-PE (BioLegend clone HIB19) and acquiring fluorescence data along with cell counts using the Cyto-FLEX-LX.

Figure 13:
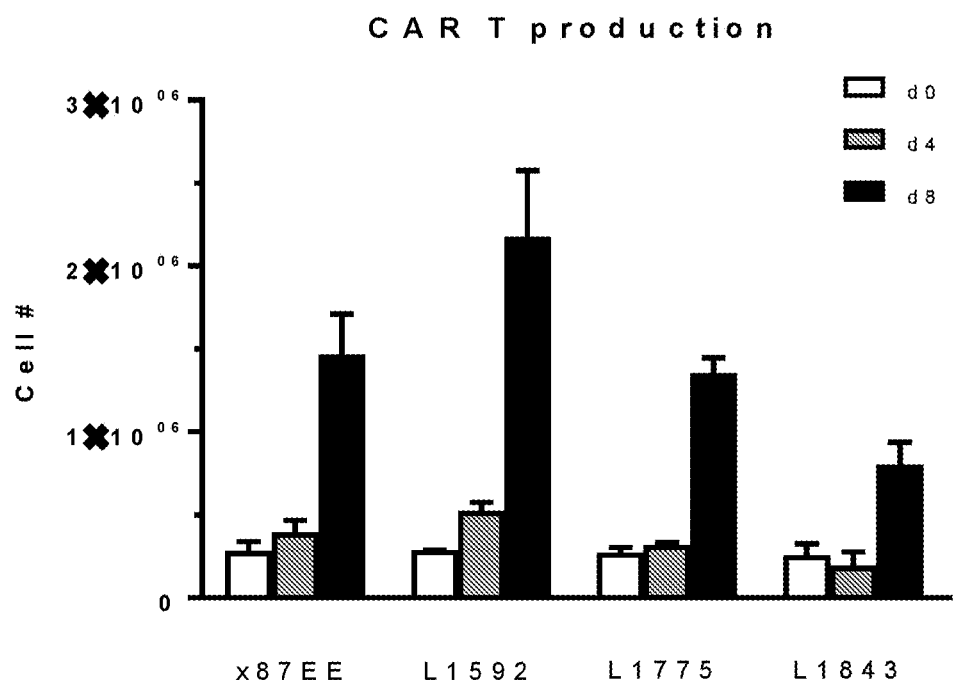
FIG. 13. In vitro analysis of CAR T cells generated using the first-generation TRC 1-2x.87EE meganuclease, or the second-generation TRC 1-2L.1592, TRC 1-2L.1775, and TRC 1-2L.1843 meganucleases. A) Total number of cells on day 0, 4, and 8 post-editing. B) Total number of edited cells (i.e. TCR-negative) on day 0, 4, and 8 post-editing. C) Total number of TCR-negative/CAR-positive cells on day 0, 4, and 8 post-editing.

Compared to T cells electroporated with no RNA (mock control), total culture cellularity at day 8 was approximately 50% reduced for T cells edited with the TRC 1-2 meganucleases x.87EE and L.1775 (FIG. 13A). Cultures edited with L.1592 or L.1843 did not display reductions in total culture cellularity to this extent. When taking editing efficiency into consideration, and calculating the total number of edited cells generated in the process, L.1592 generated the most TCR knockout cells (FIG. 13B). Variants x.87EE and L.1775 generated nearly equivalent numbers of edited cells while L.1843 generated the fewest. This pattern was also observed when measuring the number of CAR+/TCR− cells in culture (FIG. 13C).

Figure 14:
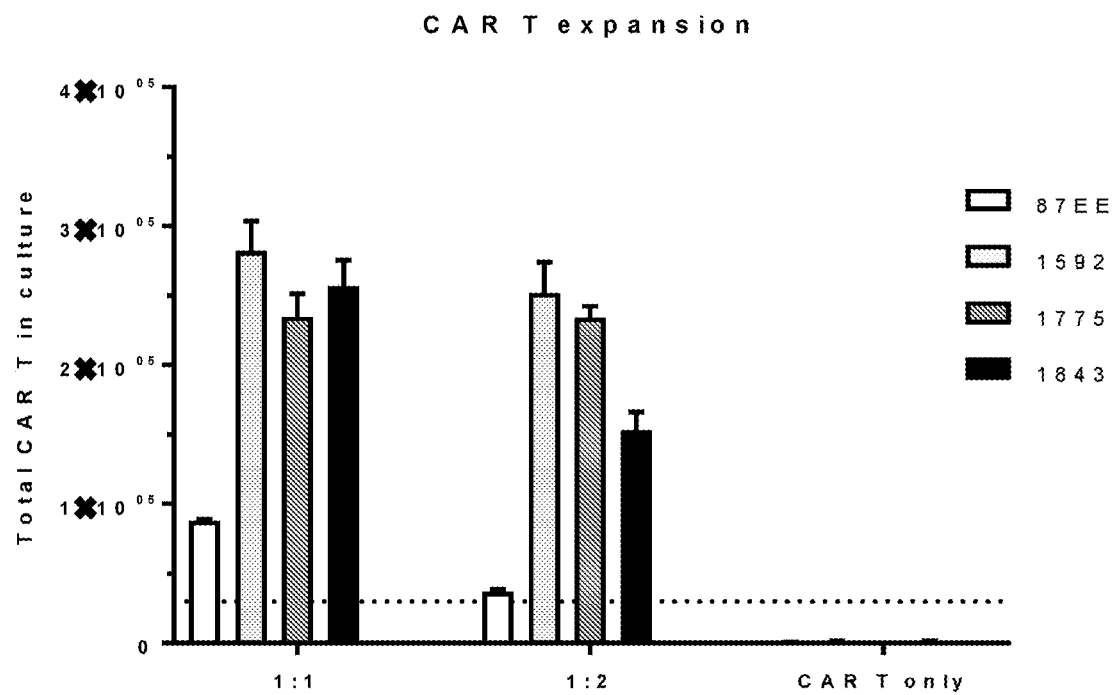
FIG. 14. CAR T cell expansion following co-culture with antigen-bearing target cells. Expansion was assessed following co-culture of CAR T cells with the CD19+ tumor lines Raji or Nalm6 at E:T ratios of 1:1 and 1:2 for 5 days. The cell input number is identified by the dashed line.

When CAR T cells were co-cultured with antigen-bearing target cells, CAR T cells produced with TRC 1-2 x.87EE expanded nearly three-fold over the input number (defined by horizontal dashed line—FIG. 14). Surprisingly, CAR T cells produced with optimized nucleases proliferated much more avidly than x.87EE, approaching a 10-fold expansion after 5 days. When the E:T ratio was increased to 1:2, proliferation of x.87EE and L.1843-edited CAR T cells was reduced by approximately ½ relative to the 1:1 ratio. This was not observed in CAR T cells produced using L.1775 or L.1592, which were found to perform significantly better ($p<0.0001$, FIG. 15A) than the other TRC 1-2 nucleases. When the remaining number of CD19+ Raji cells were measured (at a 1:2 E:T ratio FIG. 15B), all 4 CAR T products demonstrated reductions in Raji numbers of 90% or more compared to a control culture receiving no CAR T cells.

CAR T cells produced using optimized nucleases eliminated Raji cells significantly better than cells produced using x.87EE.

Analyses of co-culture supernatants showed that higher levels of effector cytokines were produced when CAR T cells were made using optimized nucleases rather than x.87EE. L.1592-edited CAR T cells secreted the highest levels of IL-2, TNFα, IFNγ, and granzyme B (FIG. 16A-16D), and the second-highest levels of perforin (FIG. 16E). In the cases of IL-2 and TNFα, the differences between the cytokine production of x.87EE-edited CAR T cells and L.1592-edited CAR T cells were 2-3 fold, whereas all other differences were minor.

Figure 16:
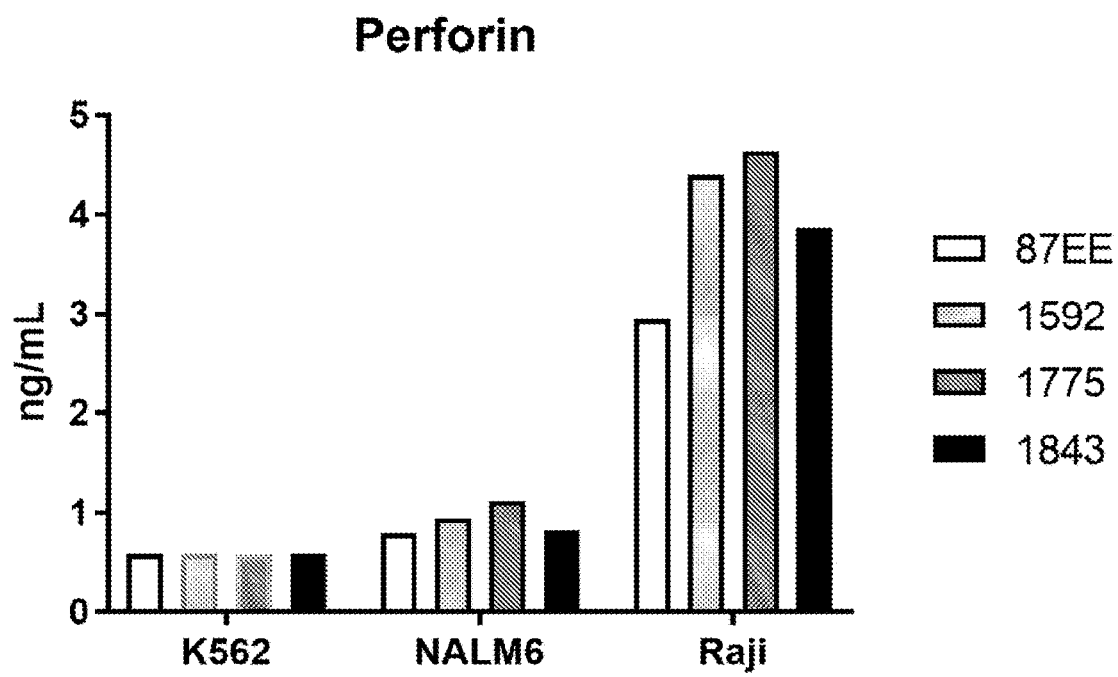
FIG. 16. CAR T cell cytokine secretion into culture supernatants following co-culture with antigen-bearing target cells for 2 days. Cytokine secretion was assessed following co-culture of CAR T cells with the CD19+ tumor lines Raji or Nalm6 at E:T ratios of 1:1 and 1:2. CD19-negative K562 myelogenous leukemia cells were used as controls. A) IL-2 secretion. B) TNF-alpha secretion. C) INF-gamma secretion. D) Granzyme B secretion. E) Perforin secretion.

Overall, the optimized TRC 1-2 meganucleases L.1775, L.1592, and L.1843 were functionally superior to x.87EE. This was true in terms of the nucleases' relative abilities to support the manufacture of CAR T cells (FIG. 13) as well as the ability of CAR T cells to respond to encounter with their target antigen (FIGS. 14-16). Drawing from multiple experiments, it appears that while L.1775 generally supported the highest editing efficiency (knockout frequency), and L.1843 allowed the greatest expansion of T cells after editing, L.1592 combined the second-highest editing efficiency with the highest or second-highest expansion to produce the highest overall number of CAR T cells. Importantly, CAR T cells produced with L.1592 displayed functional advantages (proliferation, target cell killing, and cytokine production) over the other optimized meganucleases.

4. Residence Time of Optimized TRC 1-2 Meganuclease In Vitro

Studies were further conducted to determine if the optimized second-generation TRC 1-2 meganucleases had a shorter residence time in vitro than the first-generation TRC 1-2x.87EE. A shorter residence time can be advantageous in the context of gene editing and a potential reduction in off target cutting.

In these studies, T cells were obtained from an apheresis product (Key Biologics) by magnetic enrichment of CD4+ and CD8+ cells using CD4 and CD8 microbeads and an LD column (Miltenyi). Cells were activated for three days with anti-CD3/anti-CD28 TransAct reagent (Miltenyi) in Xuri medium (GE) containing 5% FBS (GE Hyclone), 10 ng/ml IL-2 (Cellgenix), and 1% antibiotic/antimycotic solution (Gibco). Cells were then electroporated with in vitro transcribed mRNA encoding TRC 1-2x.87EE or TRC 1-2L.1592 nucleases (Trilink), 1 ug of mRNA per 1e6 cells, using the MaxCyte electroporation system. Cells were subsequently transduced with a recombinant AAV6 vector carrying a donor template encoding an anti-CD19 chimeric antigen receptor designed for insertion at the TRC 1-2 site by homologous recombination (SAB Tech) in serum-free Xuri medium containing 30 ng/ml IL-2 and 1% antibiotic/antimycotic solution. At 6 hours post-electroporation, samples were quantified and resuspended in Xuri medium containing 5% FBS, 30 ng/ml IL-2 and 1% antibiotic/antimycotic solution. At the 96 hour time point, residual unedited CD3+ T cells were removed from the TRC electroporated group by magnetic depletion using LD columns, CliniMACS buffer, and CD3 Microbeads (Miltenyi). Cells were then cultured in Xuri media+5% FBS/1% anti-anti+10 ng/ml IL-15 and IL-21 at 37 degrees C. for the remainder of the experiment.

At 6 hours, 24 hours, 48 hours, 96 hours, and 168 hours post-electroporation, T cell samples were quantified, and equal amount of viable cells were pelleted and resuspended in RIPA buffer (EMD Millipore) with protease inhibitors (Roche) added, mixed well, and either cryopreserved or incubated on ice for 30 minutes prior to further processing as described below for the Western blots.

Mock cells from the same donor were activated and cultured in the same medium as the nuclease treatment groups and harvested at 24 hours after the nuclease treatment groups had been electroporated.

For Western blot analysis, lysates were centrifuged and the supernatants were transferred to a new tube and placed on ice. Protein concentrations were determined by the BCA assay (Pierce), and 15 μg total protein for each sample was sample buffer+DTT (NuPage), and incubated at 90o C for 10 min. 5 μg of each sample was loaded in each well of the gels. A single mock sample from the 24 hour post-electroporation time point was used as a control. After electrophoresis, samples were transferred (NuPage electrophoresis system and reagents) to PVDF membranes (Novex). Membranes were blocked with 5% nonfat-dried milk in TBS-T, and stained with primary antibodies:

Blots Primary Antibodies

A Rabbit polyclonal anti nuclease, (Precision BioSciences proprietary, used at 1:6500)

B Mouse anti B-actin (Sigma, used at 1:15000)

Membranes were washed 6 times, then incubated with appropriate secondary antibodies:

Blots Secondary Antibodies

A Goat anti Rabbit HRP (Invitrogen, used at 1:50000)

B Goat anti Mouse HRP (Invitrogen, used at 1:75000)

After wash steps, membranes were exposed to ECL Prime (Amersham), wrapped in Saran wrap, and images captured using the UVP ChemiDoc-It 815 Imager.

Figure 17:
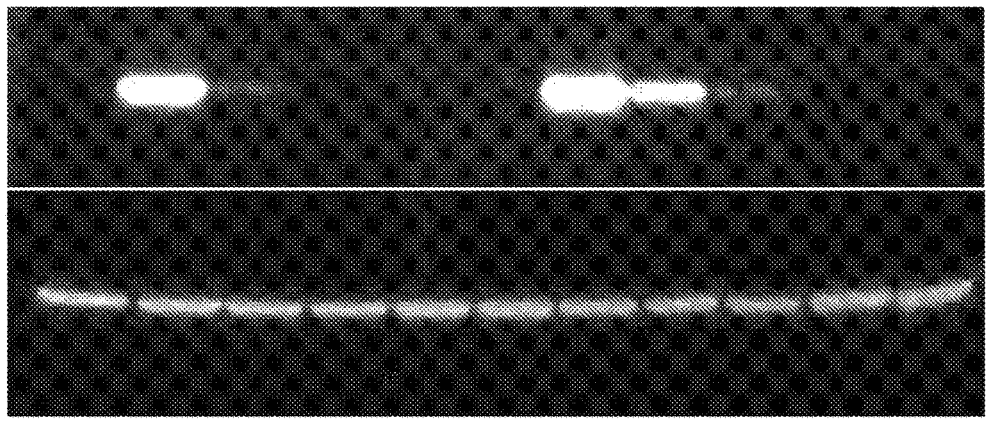
FIG. 17. Western blot analysis of meganuclease expression in CAR T cells. Cells were electroporated with mRNA encoding the TRC 1-2x.87EE or TRC 1-2L.1592 meganucleases and were subsequently transduced with a recombinant AAV6 vector carrying a donor template encoding an anti-CD19 CAR designed for insertion at the TRC 1-2 site. At 6 hours, 24 hours, 48 hours, 96 hours, and 168 hours post-electroporation, meganuclease protein expression was determined by Western blot analysis. Mock cells from the same donor were activated and cultured in the same medium as the nuclease treatment groups and harvested at 24 hours after the nuclease treatment groups had been electroporated.

As shown in FIG. 17, no nuclease expression was detectable in the Mock sample, as anticipated. In samples electroporated with mRNA encoding the TRC1-2x.87EE or TRC1-2L.1592 nucleases, the nuclease protein was highly expressed at the earliest time point analyzed, 6 hours post-electroporation. At 24 hours post-electroporation, the protein remains detectable; however, expression was observed to be substantially lower than at 6 hours post-electroporation for both nucleases, and markedly lower for TRC 1-2L.1592 than TRC 1-2x.87EE at this time point. In the TRC 1-2L.1592 mRNA treated sample, no nuclease protein is detectable at 48 hours post-electroporation or at subsequent time points, whereas TRC 1-2x.87EE protein expression is still detectable at this time point. Actin expression is consistent across all samples and time points, indicating that equivalent quantities of protein were added for each sample.

These studies demonstrated that TRC1-2x.87EE and TRC1-2L.1592 nucleases were expressed at high levels at 6 hours post-electroporation of mRNA. However, expression of TRC 1-2L.1592 in T cells decreased more rapidly than TRC 1-2x.87EE. As demonstrated in FIG. 11, TRC 1-2L.1592 does not exhibit decreased gene-editing efficiency compared to TRC 1-2x.87EE, although it is expressed for a shorter period of time. Retention of high gene-editing activity while reducing duration of expression are desirable characteristics of TRC 1-2L.1592 and represent an unexpected and advantageous improvement over TRC 1-2x.87EE, as these properties correlate with enhanced (i.e., increased) tolerability and greater proliferative capacity of the T cells, and lower off-target activity with TRC 1-2L.1592 compared to TRC 1-2x.87EE.

Example 3

Evaluation of Optimized TRC 1-2 Meganucleases in CAR T Production

The TRC 1-2L.1592 meganuclease was further evaluated in a large-scale process run to determine if the production of CAR T cells at scale was improved versus the first-generation TRC 1-2x.87EE meganuclease.

The large-scale process used to generate allogeneic CAR T cells with TRC 1-2x.87EE started with a fresh Leukopak from a healthy, prequalified donor. The Leukopak product was washed to remove platelets before undergoing immunomagnetic enrichment of the target T cells. The enriched T cells were then washed into growth media and activated using an activation reagent. After a 3 day activation period, the cells were washed and concentrated in electroporation buffer. mRNA encoding TRC 1-2x.87EE was added and the mixture of cells and mRNA was processed through an electroporation device. The electroporated cells were diluted with growth media containing an AAV vector encoding the CAR insert gene. After an expansion period, the cells were collected on day 8 and an immunomagnetic depletion of the CD3-positive population was performed. After depletion, the target CD3-negative cells were expanded in growth media for an additional period. Finally, the cells were collected on day 13, washed, and concentrated into a cryoprotectant solution and frozen. The large-scale process used to generate allogeneic CAR T cells with TRC 1-2L.1592 was performed essentially the same as described for TRC 1-2x.87EE, except that the growth media formulation in the TRC 1-2L.1592 run was animal origin free (AOF).

Figure 18:
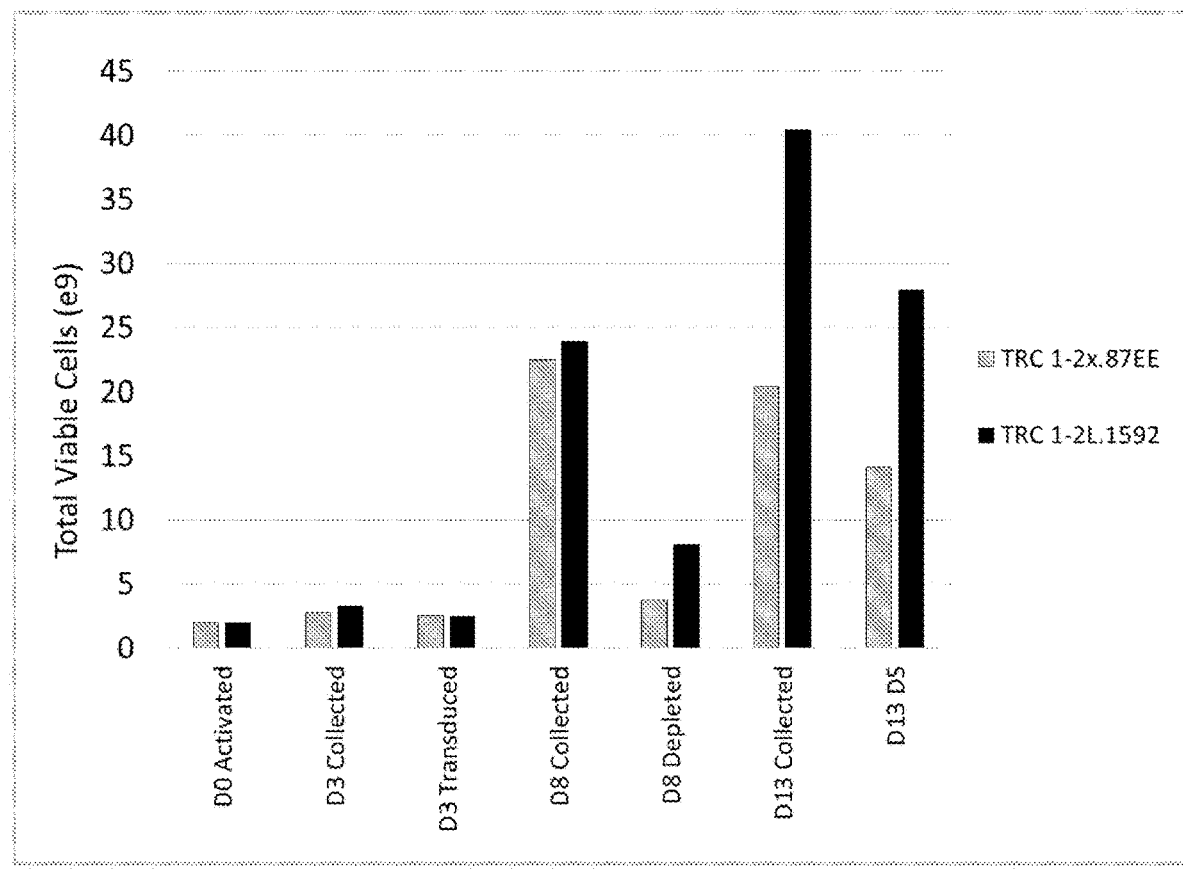
FIG. 18. Total number of viable cells at days 0, 3, 8 (before and after CD3-positive cell depletion), and 13 of large-scale CAR T manufacturing process runs using TRC 1-2x.87EE or TRC 1-2L.1592.

The total number of viable cells was determined at key time points in the production processes (FIG. 18). The cell number is comparable from day 0 up to the day 8 depletion step. However, due to significantly higher T cell receptor knockout efficiency with TRC 1-2L.1592, the depletion step in the TRC 1-2L.1592 process advantageously recovered more than twice the cell number as recovered in the TRC 1-2x.87EE process run. Expansion rates are similar between day 8 and 13, leading to approximately two-fold greater total viable cells on day 13.

Figure 19:
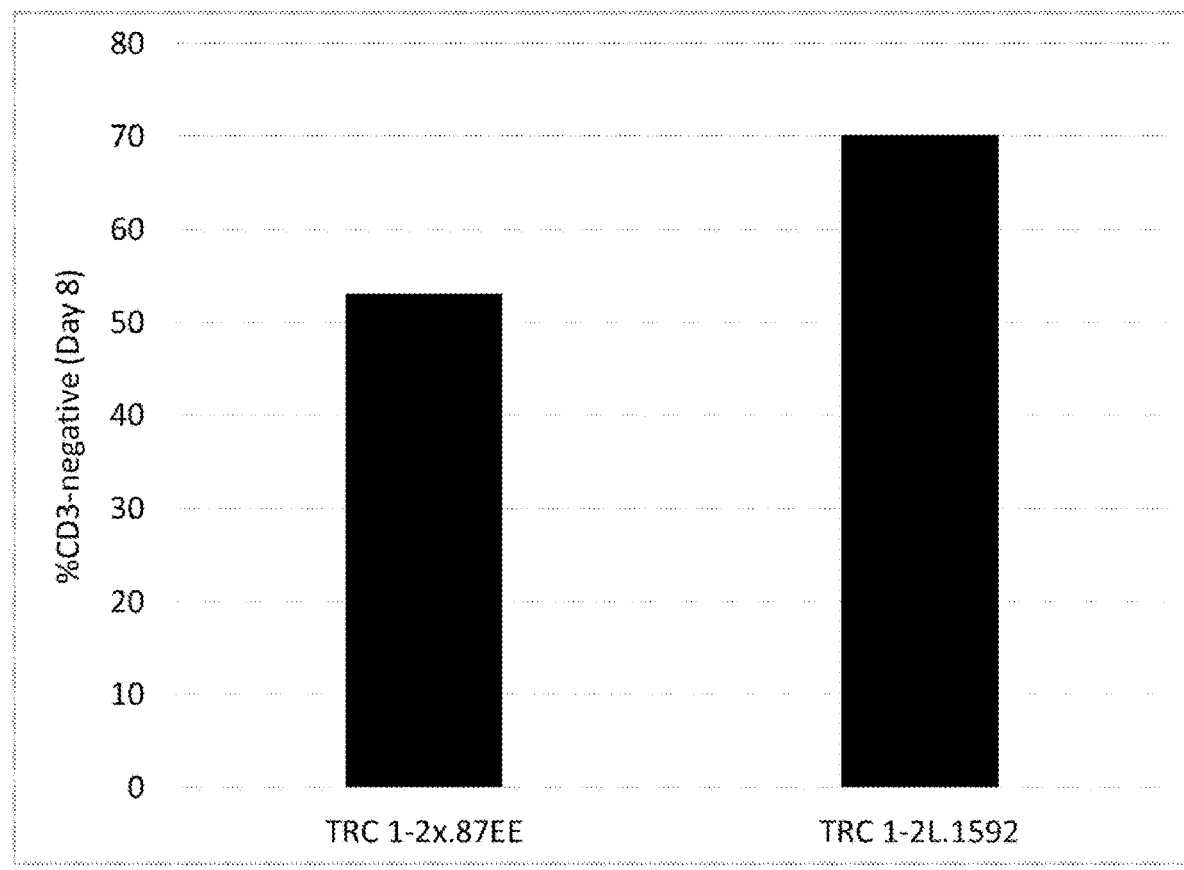
FIG. 19. Total number of viable CD3-negative cells at day 8 of large-scale CAR T manufacturing process runs using TRC 1-2x.87EE or TRC 1-2L.1592.

The CD3 knockout efficiency (i.e., an indicator of knockout of the endogenous T cell receptor) was determined by flow cytometry on day 8 of each production run (FIG. 19). Surprisingly, the percentage of CD3-negative, gene-edited cells (of total live cells) was nearly 20% higher in the TRC 1-2L.1592 process run than the TRC 1-2x.87EE process run.

Figure 20:
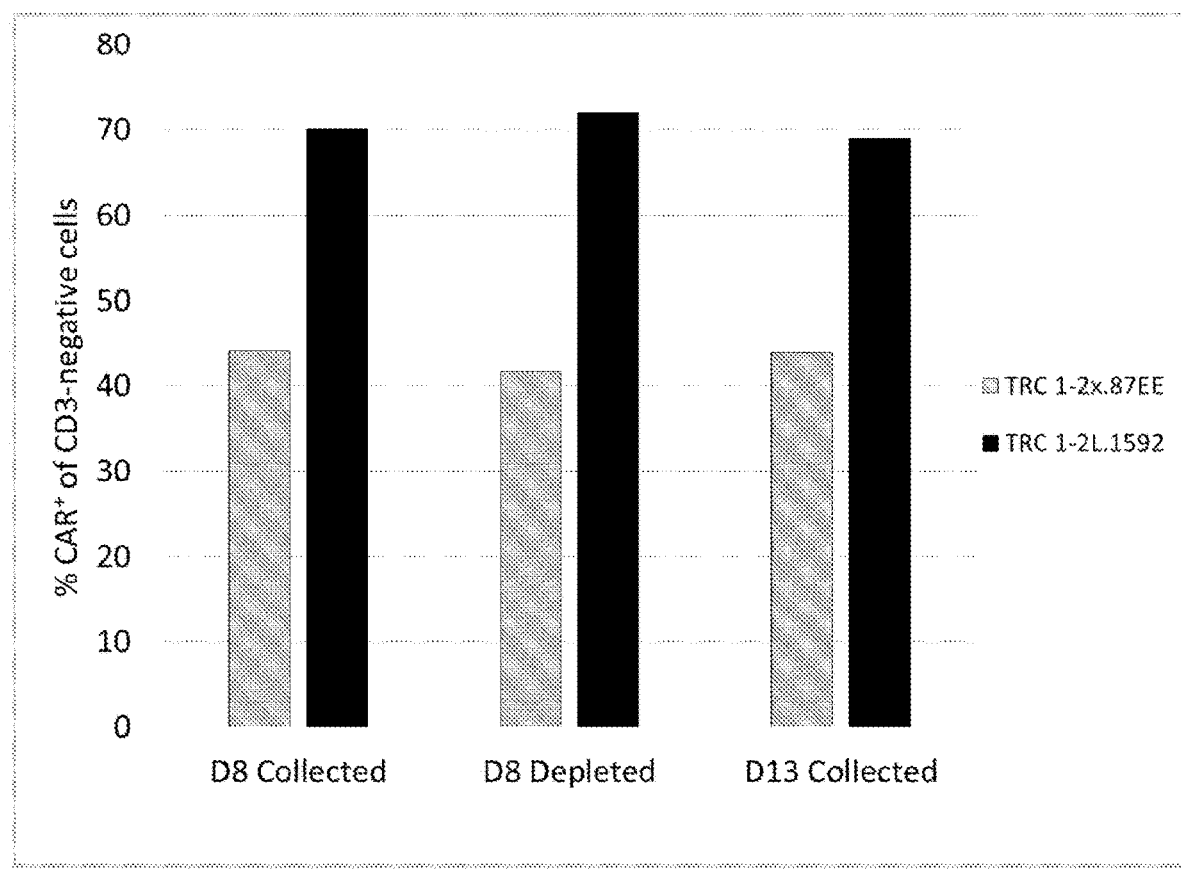
FIG. 20. Percentage of CD3-negative cells that are CAR-positive at day 8 (before and after CD3-positive cell depletion) and day 13 of large-scale CAR T manufacturing process runs using TRC 1-2x.87EE or TRC 1-2L.1592.

Finally, CAR knock-in efficiency was measured by flow cytometry at 3 key time points in each production process (FIG. 20). Unexpectedly, the percentage of CAR-positive, transduced cells (of CD3-negative cells) is approximately 25% higher in the TRC 1-2L.1592 process run than in the TRC 1-2x.87EE process run. The CAR knock-in percentages are stable for both processes between day 8 and the end of the process on day 13, resulting in a similarly higher percentage of CAR-positive cells at the conclusion of the TRC 1-2L.1592 process run.

In conclusion, these studies surprisingly showed that the TRC 1-2L.1592 nuclease significantly improved the quantity, as well as the quality of the final allogeneic cell therapy product. TRC 1-2L.1592 more efficiently knocked out the endogenous T cell receptor, resulting in a larger population of gene edited CD3-negative cells, improving the overall production process yield by approximately two-fold. Additionally, TRC 1-2L.1592 potentially provides an improved environment for homologous recombination with the CAR gene insert at the targeted double-strand break, as evidenced by the improved CAR knock-in efficiency. The increase in the CAR-positive percentage results in significantly higher drug product purity with fewer CAR-negative cells.

The invention claimed is:

1. An engineered meganuclease that binds and cleaves a recognition sequence consisting of SEQ ID NO: 5 within a human T cell receptor (TCR) alpha constant region gene, wherein said engineered meganuclease comprises an amino acid sequence of SEQ ID NO: 7.

2. A polynucleotide comprising a nucleic acid sequence encoding said engineered meganuclease of claim 1.

3. The polynucleotide of claim 2, wherein said polynucleotide is an mRNA.

4. A recombinant DNA construct comprising said polynucleotide of claim 2.

5. A viral vector comprising said polynucleotide of claim 2, wherein said viral vector is a recombinant adeno-associated viral (AAV) vector.

* * * * *